(12) United States Patent
Hosono et al.

(10) Patent No.: US 7,888,024 B2
(45) Date of Patent: Feb. 15, 2011

(54) METHOD OF DETECTING GENETIC POLYMORPHISM

(75) Inventors: Naoya Hosono, Yokohama (JP); Mitsuaki Kubo, Yokohama (JP); Yusuke Nakamura, Yokohama (JP)

(73) Assignee: Riken, Wako-shi (JP)

( * ) Notice: Subject to any disclaimer, the term of this patent is extended or adjusted under 35 U.S.C. 154(b) by 355 days.

(21) Appl. No.: 12/058,318

(22) Filed: Mar. 28, 2008

(65) Prior Publication Data

US 2008/0286783 A1    Nov. 20, 2008

(30) Foreign Application Priority Data

Mar. 28, 2007    (JP) .............................. 2007-086067

(51) Int. Cl.
*C12Q 1/68* (2006.01)
*C12P 19/34* (2006.01)
*C07H 21/02* (2006.01)

(52) U.S. Cl. .......................... 435/6; 435/91.2; 536/23.1

(58) Field of Classification Search ....................... None
See application file for complete search history.

(56) References Cited

PUBLICATIONS

Hosono et al. Multiplex PCR-based real-time invader assay (mPCR-RETINA): a novel SNP-based method for detecting allelic asymmetries within copy number variation regions. Human Mutation 29(1):182-189 (2008).*
Locke et al., *American Journal of Human Genetics*, 79: 275-290 (Aug. 2006).
Lyamichev, et al., *Nature Biotechnology*, 17: 292-296 (Mar. 1999).
Ohnishi et al., *J. Hum. Genet.*, 46: 471-477 (2001).
Wang et al., *Nucleic Acids Research*, 33(21): e183 (1-14) (2005).
Beckman, et al., Nature Reviews/Genetics, 8: 639-646 (Aug. 2007).
Hersberger et al., *Clinical Chemistry*, 46(8): 1072-1077 (2000).
Ishida et al., *Drug Metabol. Pharmacokin.*, 17(2): 157-160 (2002).
Heller et al., *Ther. Drug Monit.*, 28(5): 673-677 (Oct. 2006).
Zackrisson, et al., *Eur. J. Clin. Pharmacol.*, 59: 521-526 (2003).
Bender, *Methods in Molecular Biology*, 297: 243-252 (2005).
Schaeffeler et al., *Human Mutation*, 22: 476-485 (2003).
Bodin, et al., *Journal of Biomedicine and Biotechnology*, 3: 248-253 (2005).
Yu et al., *BMC Genomics*, 7: 143 (2006).
Ruiz-Ponte, *Clinical Chemistry*, 46(10): 1574-1582 (2000).
Tsui, et al., *Clinical Chemistry*, 51(12): 2358-2362 (2005).

* cited by examiner

*Primary Examiner*—Samuel C Woolwine
(74) *Attorney, Agent, or Firm*—Leydig, Voit & Mayer, Ltd.

(57) ABSTRACT

The present invention provides a novel polymorphism detecting method suitable for the detection and identification of copy number variation.

Provided is a method of determining the genotype of a subject in a genomic region comprising an SNP site, comprising a step for performing typing of the SNP site by the invader assay with a DNA-containing sample comprising the genomic region from the subject as the template, wherein fluorescence is measured on a real time basis. The copy number ratio of both alleles is determined using the fluorescence intensity ratio of each allele at a time before saturation of fluorescence intensity. Preferably, the present method further comprises a step for amplifying the genomic region comprising an SNP site prior to the invader step. In this step of amplification, a plurality of regions comprising a plurality of SNP sites can be simultaneously amplified. Furthermore, the present method enables the determination of the copy number of each allele when combined with quantitative PCR.

8 Claims, 19 Drawing Sheets

(d)

(c)

CYP2D6-Assay Map

SEQUENCE LISTING

```
<160> NUMBER OF SEQ ID NOS: 307

<210> SEQ ID NO 1
<211> LENGTH: 80
<212> TYPE: DNA
<213> ORGANISM: Artificial
<220> FEATURE:
<223> OTHER INFORMATION: Synthetic

<400> SEQUENCE: 1
ggcctgcgcc tccacaggtg gctgatgacg gggctctcca gcctaaaacg ctggaaggct      60
tagtgcctgg agtgccctcc                                                  80

<210> SEQ ID NO 2
<211> LENGTH: 80
<212> TYPE: DNA
<213> ORGANISM: Artificial
<220> FEATURE:
<223> OTHER INFORMATION: Synthetic

<400> SEQUENCE: 2
ggcctgcgcc tccacaggtg gctgatgacg gggctctcca gcctcaaacg ctggaaggct      60
tagtgcctgg agtgccctcc                                                  80

<210> SEQ ID NO 3
<211> LENGTH: 18
<212> TYPE: DNA
<213> ORGANISM: Artificial
<220> FEATURE:
<223> OTHER INFORMATION: Forward Primer

<400> SEQUENCE: 3
ggctgatgac ggggctct                                                    18

<210> SEQ ID NO 4
<211> LENGTH: 20
<212> TYPE: DNA
<213> ORGANISM: Artificial
<220> FEATURE:
<223> OTHER INFORMATION: Reverse Primer

<400> SEQUENCE: 4
ccaggcacta agccttccag                                                  20

<210> SEQ ID NO 5
<211> LENGTH: 30
<212> TYPE: DNA
<213> ORGANISM: Artificial
<220> FEATURE:
<223> OTHER INFORMATION: Invader Probe

<400> SEQUENCE: 5
cactccaggc actaagcctt ccagcgtttc                                       30
```

```
<210> SEQ ID NO 6
<211> LENGTH: 28
<212> TYPE: DNA
<213> ORGANISM: Artificial
<220> FEATURE:
<223> OTHER INFORMATION: Allele Probe 1

<400> SEQUENCE: 6
atgacgtggc agactaggct ggagagcc                                          28

<210> SEQ ID NO 7
<211> LENGTH: 24
<212> TYPE: DNA
<213> ORGANISM: Artificial
<220> FEATURE:
<223> OTHER INFORMATION: Allele Probe 2

<400> SEQUENCE: 7
cgcgccgagg gaggctggag agcc                                              24

<210> SEQ ID NO 8
<211> LENGTH: 19
<212> TYPE: DNA
<213> ORGANISM: Artificial
<220> FEATURE:
<223> OTHER INFORMATION: Forward Primer

<400> SEQUENCE: 8
ctgggctggg agcagcctc                                                    19

<210> SEQ ID NO 9
<211> LENGTH: 23
<212> TYPE: DNA
<213> ORGANISM: Artificial
<220> FEATURE:
<223> OTHER INFORMATION: Reverse Primer

<400> SEQUENCE: 9
cactcgctgg cctgtttcat gtc                                               23

<210> SEQ ID NO 10
<211> LENGTH: 22
<212> TYPE: DNA
<213> ORGANISM: Artificial
<220> FEATURE:
<223> OTHER INFORMATION: Forward Primer

<400> SEQUENCE: 10
ctggaatccg gtgtcgaagt gg                                                22

<210> SEQ ID NO 11
<211> LENGTH: 20
<212> TYPE: DNA
<213> ORGANISM: Artificial
<220> FEATURE:
<223> OTHER INFORMATION: Reverse Primer

<400> SEQUENCE: 11
ctcggcccct gcactgtttc                                                   20

<210> SEQ ID NO 12
<211> LENGTH: 22
<212> TYPE: DNA
<213> ORGANISM: Artificial
<220> FEATURE:
```

<223> OTHER INFORMATION: Invader Probe

<400> SEQUENCE: 12
gcagtggcag ggggcctggt gt                                          22

<210> SEQ ID NO 13
<211> LENGTH: 27
<212> TYPE: DNA
<213> ORGANISM: Artificial
<220> FEATURE:
<223> OTHER INFORMATION: Allele Probe 1

<400> SEQUENCE: 13
atgacgtggc agacggtagc gtgcagc                                     27

<210> SEQ ID NO 14
<211> LENGTH: 24
<212> TYPE: DNA
<213> ORGANISM: Artificial
<220> FEATURE:
<223> OTHER INFORMATION: Allele Probe 2

<400> SEQUENCE: 14
cgcgccgagg agtagcgtgc agcc                                        24

<210> SEQ ID NO 15
<211> LENGTH: 25
<212> TYPE: DNA
<213> ORGANISM: Artificial
<220> FEATURE:
<223> OTHER INFORMATION: Invader Probe

<400> SEQUENCE: 15
ccttacccgc atctcccacc cccat                                       25

<210> SEQ ID NO 16
<211> LENGTH: 24
<212> TYPE: DNA
<213> ORGANISM: Artificial
<220> FEATURE:
<223> OTHER INFORMATION: Allele Probe 1

<400> SEQUENCE: 16
cgcgccgagg agacgcccct ttcg                                        24

<210> SEQ ID NO 17
<211> LENGTH: 28
<212> TYPE: DNA
<213> ORGANISM: Artificial
<220> FEATURE:
<223> OTHER INFORMATION: Allele Probe 2

<400> SEQUENCE: 17
atgacgtggc agacggacgc ccctttcg                                    28

<210> SEQ ID NO 18
<211> LENGTH: 30
<212> TYPE: DNA
<213> ORGANISM: Artificial
<220> FEATURE:
<223> OTHER INFORMATION: Invader Probe

<400> SEQUENCE: 18
ggcagagaac aggtcagcca ccactatgct                                  30

<210> SEQ ID NO 19
<211> LENGTH: 33
<212> TYPE: DNA
<213> ORGANISM: Artificial
<220> FEATURE:
<223> OTHER INFORMATION: Allele Probe 1

<400> SEQUENCE: 19
atgacgtggc agacgcaggt tctcatcatt gaa                33

<210> SEQ ID NO 20
<211> LENGTH: 30
<212> TYPE: DNA
<213> ORGANISM: Artificial
<220> FEATURE:
<223> OTHER INFORMATION: Allele Probe 2

<400> SEQUENCE: 20
cgcgccgagg acaggttctc atcattgaag                   30

<210> SEQ ID NO 21
<211> LENGTH: 21
<212> TYPE: DNA
<213> ORGANISM: Artificial
<220> FEATURE:
<223> OTHER INFORMATION: Forward Primer

<400> SEQUENCE: 21
ggtgtcccag caaagttcat g                            21

<210> SEQ ID NO 22
<211> LENGTH: 23
<212> TYPE: DNA
<213> ORGANISM: Artificial
<220> FEATURE:
<223> OTHER INFORMATION: Reverse Primer

<400> SEQUENCE: 22
cctcctgctc atgatcctac atc                          23

<210> SEQ ID NO 23
<211> LENGTH: 14
<212> TYPE: DNA
<213> ORGANISM: Artificial
<220> FEATURE:
<223> OTHER INFORMATION: TaqMan Probe

<400> SEQUENCE: 23
cccccgcctg tacc                                    14

<210> SEQ ID NO 24
<211> LENGTH: 20
<212> TYPE: DNA
<213> ORGANISM: Artificial
<220> FEATURE:
<223> OTHER INFORMATION: Reverse Primer

<400> SEQUENCE: 24
acttcgacac cggattccag                              20

<210> SEQ ID NO 25
<211> LENGTH: 28
<212> TYPE: DNA
<213> ORGANISM: Artificial
<220> FEATURE:
<223> OTHER INFORMATION: Forward Primer

```
<400> SEQUENCE: 25
gttatcccag aaggctttgc aggcttca                                28

<210> SEQ ID NO 26
<211> LENGTH: 26
<212> TYPE: DNA
<213> ORGANISM: Artificial
<220> FEATURE:
<223> OTHER INFORMATION: Reverse Primer

<400> SEQUENCE: 26
gccgactgag ccctgggagg taggta                                  26

<210> SEQ ID NO 27
<211> LENGTH: 18
<212> TYPE: DNA
<213> ORGANISM: Artificial
<220> FEATURE:
<223> OTHER INFORMATION: Sequence Primer

<400> SEQUENCE: 27
tgttctctgc cgggatgg                                           18

<210> SEQ ID NO 28
<211> LENGTH: 20
<212> TYPE: DNA
<213> ORGANISM: Artificial
<220> FEATURE:
<223> OTHER INFORMATION: Sequence Primer

<400> SEQUENCE: 28
gccctatcac gtcgtcgatc                                         20

<210> SEQ ID NO 29
<211> LENGTH: 22
<212> TYPE: DNA
<213> ORGANISM: Artificial
<220> FEATURE:
<223> OTHER INFORMATION: Forward Primer

<400> SEQUENCE: 29
gtgtcacaac cacctctttg ca                                      22

<210> SEQ ID NO 30
<211> LENGTH: 21
<212> TYPE: DNA
<213> ORGANISM: Artificial
<220> FEATURE:
<223> OTHER INFORMATION: Reverse Primer

<400> SEQUENCE: 30
tccaaggttg agatggttgg a                                       21

<210> SEQ ID NO 31
<211> LENGTH: 35
<212> TYPE: DNA
<213> ORGANISM: Artificial
<220> FEATURE:
<223> OTHER INFORMATION: Invader Probe

<400> SEQUENCE: 31
gggtcctcaa atccagtttg aaatccagtt cttga                        35

<210> SEQ ID NO 32
<211> LENGTH: 28
```

```
<212> TYPE: DNA
<213> ORGANISM: Artificial
<220> FEATURE:
<223> OTHER INFORMATION: Allele Probe 1

<400> SEQUENCE: 32
cgcgccgagg ttgactctga agcctgac                                              28

<210> SEQ ID NO 33
<211> LENGTH: 31
<212> TYPE: DNA
<213> ORGANISM: Artificial
<220> FEATURE:
<223> OTHER INFORMATION: Allele Probe 2

<400> SEQUENCE: 33
atgacgtggc agacctgact ctgaagcctg a                                          31

<210> SEQ ID NO 34
<211> LENGTH: 27
<212> TYPE: DNA
<213> ORGANISM: Artificial
<220> FEATURE:
<223> OTHER INFORMATION: Forward Primer

<400> SEQUENCE: 34
tggatccata aaataggaa aaactga                                                27

<210> SEQ ID NO 35
<211> LENGTH: 21
<212> TYPE: DNA
<213> ORGANISM: Artificial
<220> FEATURE:
<223> OTHER INFORMATION: Reverse Primer

<400> SEQUENCE: 35
tcagatttca tcacagtcgc g                                                     21

<210> SEQ ID NO 36
<211> LENGTH: 31
<212> TYPE: DNA
<213> ORGANISM: Artificial
<220> FEATURE:
<223> OTHER INFORMATION: Invader Probe

<400> SEQUENCE: 36
ggatccacag agaatcctga tcagcaggac a                                          31

<210> SEQ ID NO 37
<211> LENGTH: 26
<212> TYPE: DNA
<213> ORGANISM: Artificial
<220> FEATURE:
<223> OTHER INFORMATION: Allele Probe 1

<400> SEQUENCE: 37
cgcgccgagg taggctggac ccacag                                                26

<210> SEQ ID NO 38
<211> LENGTH: 28
<212> TYPE: DNA
<213> ORGANISM: Artificial
<220> FEATURE:
<223> OTHER INFORMATION: Allele Probe 2

<400> SEQUENCE: 38
```
atgacgtggc agaccaggct ggacccac                                             28

<210> SEQ ID NO 39
<211> LENGTH: 26
<212> TYPE: DNA
<213> ORGANISM: Artificial
<220> FEATURE:
<223> OTHER INFORMATION: Forward Primer

<400> SEQUENCE: 39
ggccttggtt tctagtaaag acaact                                               26

<210> SEQ ID NO 40
<211> LENGTH: 20
<212> TYPE: DNA
<213> ORGANISM: Artificial
<220> FEATURE:
<223> OTHER INFORMATION: Reverse Primer

<400> SEQUENCE: 40
gccaaaatag aactggggca                                                      20

<210> SEQ ID NO 41
<211> LENGTH: 37
<212> TYPE: DNA
<213> ORGANISM: Artificial
<220> FEATURE:
<223> OTHER INFORMATION: Invader Probe

<400> SEQUENCE: 41
actggtccat tagtccagga agagctaaat aagcaca                                   37

<210> SEQ ID NO 42
<211> LENGTH: 31
<212> TYPE: DNA
<213> ORGANISM: Artificial
<220> FEATURE:
<223> OTHER INFORMATION: Allele Probe 1

<400> SEQUENCE: 42
cgcgccgagg ttaaaagttc tcaaggggaa g                                         31

<210> SEQ ID NO 43
<211> LENGTH: 34
<212> TYPE: DNA
<213> ORGANISM: Artificial
<220> FEATURE:
<223> OTHER INFORMATION: Allele Probe 2

<400> SEQUENCE: 43
atgacgtggc agacgtaaaa gttctcaagg ggaa                                      34

<210> SEQ ID NO 44
<211> LENGTH: 23
<212> TYPE: DNA
<213> ORGANISM: Artificial
<220> FEATURE:
<223> OTHER INFORMATION: Forward Primer

<400> SEQUENCE: 44
ttaagcttca tcagtatccc cca                                                  23

<210> SEQ ID NO 45
<211> LENGTH: 26
<212> TYPE: DNA
<213> ORGANISM: Artificial

```
<220> FEATURE:
<223> OTHER INFORMATION: Reverse Primer

<400> SEQUENCE: 45
caaagtagga aaacatcatc acagga                                              26

<210> SEQ ID NO 46
<211> LENGTH: 17
<212> TYPE: DNA
<213> ORGANISM: Artificial
<220> FEATURE:
<223> OTHER INFORMATION: TaqMan Probe

<400> SEQUENCE: 46
accatctcta aaatcct                                                        17

<210> SEQ ID NO 47
<211> LENGTH: 31
<212> TYPE: DNA
<213> ORGANISM: Artificial
<220> FEATURE:
<223> OTHER INFORMATION: Forward Primer

<400> SEQUENCE: 47
gatctagcta agagacagag atagacacat g                                        31

<210> SEQ ID NO 48
<211> LENGTH: 30
<212> TYPE: DNA
<213> ORGANISM: Artificial
<220> FEATURE:
<223> OTHER INFORMATION: Reverse Primer

<400> SEQUENCE: 48
ccaaagagtt ttctgtactc attatcttca                                          30

<210> SEQ ID NO 49
<211> LENGTH: 22
<212> TYPE: DNA
<213> ORGANISM: Artificial
<220> FEATURE:
<223> OTHER INFORMATION: TaqMan Probe

<400> SEQUENCE: 49
aagatatgag gaagggtgag aa                                                  22

<210> SEQ ID NO 50
<211> LENGTH: 25
<212> TYPE: DNA
<213> ORGANISM: Artificial
<220> FEATURE:
<223> OTHER INFORMATION: Forward Primer

<400> SEQUENCE: 50
ggagtgggaa taacaatttt cttca                                               25

<210> SEQ ID NO 51
<211> LENGTH: 30
<212> TYPE: DNA
<213> ORGANISM: Artificial
<220> FEATURE:
<223> OTHER INFORMATION: Reverse Primer

<400> SEQUENCE: 51
acttgacatt gagtttaata ctcctgtttt                                          30
```

<210> SEQ ID NO 52
<211> LENGTH: 18
<212> TYPE: DNA
<213> ORGANISM: Artificial
<220> FEATURE:
<223> OTHER INFORMATION: TaqMan Probe

<400> SEQUENCE: 52
aatgtctgcg gttaatat                                          18

<210> SEQ ID NO 53
<211> LENGTH: 25
<212> TYPE: DNA
<213> ORGANISM: Artificial
<220> FEATURE:
<223> OTHER INFORMATION: Forward Primer

<400> SEQUENCE: 53
agaacccttc tgtgttgctt aattc                                  25

<210> SEQ ID NO 54
<211> LENGTH: 21
<212> TYPE: DNA
<213> ORGANISM: Artificial
<220> FEATURE:
<223> OTHER INFORMATION: Reverse Primer

<400> SEQUENCE: 54
tgtctccaat acctctggcc a                                      21

<210> SEQ ID NO 55
<211> LENGTH: 17
<212> TYPE: DNA
<213> ORGANISM: Artificial
<220> FEATURE:
<223> OTHER INFORMATION: TaqMan Probe

<400> SEQUENCE: 55
tgcatacagg agctgga                                           17

<210> SEQ ID NO 56
<211> LENGTH: 23
<212> TYPE: DNA
<213> ORGANISM: Artificial
<220> FEATURE:
<223> OTHER INFORMATION: Forward Primer

<400> SEQUENCE: 56
gagaagcaag agcaagcaac ttc                                    23

<210> SEQ ID NO 57
<211> LENGTH: 33
<212> TYPE: DNA
<213> ORGANISM: Artificial
<220> FEATURE:
<223> OTHER INFORMATION: Reverse Primer

<400> SEQUENCE: 57
tagctagtgg tctatctatc ttgttaatgt ttt                         33

<210> SEQ ID NO 58
<211> LENGTH: 20
<212> TYPE: DNA
<213> ORGANISM: Artificial
<220> FEATURE:
<223> OTHER INFORMATION: TaqMan Probe

<400> SEQUENCE: 58
aaggagctag aaacacgaaa                                            20

<210> SEQ ID NO 59
<211> LENGTH: 25
<212> TYPE: DNA
<213> ORGANISM: Artificial
<220> FEATURE:
<223> OTHER INFORMATION: Forward Primer

<400> SEQUENCE: 59
agctgcttga gaaaatacc gagta                                       25

<210> SEQ ID NO 60
<211> LENGTH: 29
<212> TYPE: DNA
<213> ORGANISM: Artificial
<220> FEATURE:
<223> OTHER INFORMATION: Reverse Primer

<400> SEQUENCE: 60
tgttagtgac attcttttc tttgacaga                                   29

<210> SEQ ID NO 61
<211> LENGTH: 35
<212> TYPE: DNA
<213> ORGANISM: Artificial
<220> FEATURE:
<223> OTHER INFORMATION: Invader Probe

<400> SEQUENCE: 61
gacctcagag tgtggtagga gagaaagatg tgtgt                           35

<210> SEQ ID NO 62
<211> LENGTH: 42
<212> TYPE: DNA
<213> ORGANISM: Artificial
<220> FEATURE:
<223> OTHER INFORMATION: Allele Probe 1

<400> SEQUENCE: 62
atgacgtggc agacgacaaa taattcaagt acactgttat aa                   42

<210> SEQ ID NO 63
<211> LENGTH: 39
<212> TYPE: DNA
<213> ORGANISM: Artificial
<220> FEATURE:
<223> OTHER INFORMATION: Allele Probe 2

<400> SEQUENCE: 63
cgcgccgagg aacaaataat tcaagtacac tgttataag                       39

<210> SEQ ID NO 64
<211> LENGTH: 26
<212> TYPE: DNA
<213> ORGANISM: Artificial
<220> FEATURE:
<223> OTHER INFORMATION: Forward Primer

<400> SEQUENCE: 64
caacaaacct aatataaaag gccctc                                     26

<210> SEQ ID NO 65

-continued

```
<211> LENGTH: 29
<212> TYPE: DNA
<213> ORGANISM: Artificial
<220> FEATURE:
<223> OTHER INFORMATION: Reverse Primer

<400> SEQUENCE: 65
caaaaataat ctttaaatac atgcactgc                                    29

<210> SEQ ID NO 66
<211> LENGTH: 51
<212> TYPE: DNA
<213> ORGANISM: Artificial
<220> FEATURE:
<223> OTHER INFORMATION: Invader Probe

<400> SEQUENCE: 66
gcagaccaat gtatatattg tatgacgaag ctatatagtt gctttatcac a           51

<210> SEQ ID NO 67
<211> LENGTH: 49
<212> TYPE: DNA
<213> ORGANISM: Artificial
<220> FEATURE:
<223> OTHER INFORMATION: Allele Probe 1

<400> SEQUENCE: 67
atgacgtggc agaccaaata tttgcaaatt aatgcaaaat tattaataa              49

<210> SEQ ID NO 68
<211> LENGTH: 46
<212> TYPE: DNA
<213> ORGANISM: Artificial
<220> FEATURE:
<223> OTHER INFORMATION: Allele Probe 2

<400> SEQUENCE: 68
cgcgccgagg taaatatttg caaattaatg caaaattatt aataag                 46

<210> SEQ ID NO 69
<211> LENGTH: 24
<212> TYPE: DNA
<213> ORGANISM: Artificial
<220> FEATURE:
<223> OTHER INFORMATION: Forward Primer

<400> SEQUENCE: 69
atttccaata ttttgcattt gctg                                         24

<210> SEQ ID NO 70
<211> LENGTH: 25
<212> TYPE: DNA
<213> ORGANISM: Artificial
<220> FEATURE:
<223> OTHER INFORMATION: Reverse Primer

<400> SEQUENCE: 70
tcaaaagaac tctccactcc aaatt                                        25

<210> SEQ ID NO 71
<211> LENGTH: 49
<212> TYPE: DNA
<213> ORGANISM: Artificial
<220> FEATURE:
<223> OTHER INFORMATION: Invader Probe

<400> SEQUENCE: 71
```

```
gaagtgtttt acttccaatt atgtggtcaa ttttagaaga agtgctact          49

<210> SEQ ID NO 72
<211> LENGTH: 33
<212> TYPE: DNA
<213> ORGANISM: Artificial
<220> FEATURE:
<223> OTHER INFORMATION: Allele Probe 1

<400> SEQUENCE: 72
atgacgtggc agacgtggca ctgagaagaa tgt                           33

<210> SEQ ID NO 73
<211> LENGTH: 30
<212> TYPE: DNA
<213> ORGANISM: Artificial
<220> FEATURE:
<223> OTHER INFORMATION: Allele Probe 2

<400> SEQUENCE: 73
cgcgccgagg atggcactga gaagaatgtg                               30

<210> SEQ ID NO 74
<211> LENGTH: 27
<212> TYPE: DNA
<213> ORGANISM: Artificial
<220> FEATURE:
<223> OTHER INFORMATION: Forward Primer

<400> SEQUENCE: 74
aaaggcctag gaatacaatg tacaagg                                  27

<210> SEQ ID NO 75
<211> LENGTH: 23
<212> TYPE: DNA
<213> ORGANISM: Artificial
<220> FEATURE:
<223> OTHER INFORMATION: Reverse Primer

<400> SEQUENCE: 75
tcaagggtag cttgatggga ata                                      23

<210> SEQ ID NO 76
<211> LENGTH: 49
<212> TYPE: DNA
<213> ORGANISM: Artificial
<220> FEATURE:
<223> OTHER INFORMATION: Invader Probe

<400> SEQUENCE: 76
ttcataccca tgagaatgga atttttttcc atttgtttgt gtcctctca          49

<210> SEQ ID NO 77
<211> LENGTH: 32
<212> TYPE: DNA
<213> ORGANISM: Artificial
<220> FEATURE:
<223> OTHER INFORMATION: Allele Probe 1

<400> SEQUENCE: 77
atgacgtggc agacttactt ccttgagcag tg                            32

<210> SEQ ID NO 78
<211> LENGTH: 28
<212> TYPE: DNA
```

```
<213> ORGANISM: Artificial
<220> FEATURE:
<223> OTHER INFORMATION: Allele Probe 2

<400> SEQUENCE: 78
cgcgccgagg ctacttcctt gagcagtg                                              28

<210> SEQ ID NO 79
<211> LENGTH: 21
<212> TYPE: DNA
<213> ORGANISM: Artificial
<220> FEATURE:
<223> OTHER INFORMATION: Forward Primer

<400> SEQUENCE: 79
gcaggatgca aacacaagga a                                                     21

<210> SEQ ID NO 80
<211> LENGTH: 24
<212> TYPE: DNA
<213> ORGANISM: Artificial
<220> FEATURE:
<223> OTHER INFORMATION: Reverse Primer

<400> SEQUENCE: 80
tctctccttg cccaatacaa aaat                                                  24

<210> SEQ ID NO 81
<211> LENGTH: 59
<212> TYPE: DNA
<213> ORGANISM: Artificial
<220> FEATURE:
<223> OTHER INFORMATION: Invader Probe

<400> SEQUENCE: 81
cttgcccaat acaaaattt aggtgactgg caaaatttac tagggtataa ttacaatat            59

<210> SEQ ID NO 82
<211> LENGTH: 35
<212> TYPE: DNA
<213> ORGANISM: Artificial
<220> FEATURE:
<223> OTHER INFORMATION: Allele Probe 1

<400> SEQUENCE: 82
atgacgtggc agacgtaatg ctgggttaat tgtag                                      35

<210> SEQ ID NO 83
<211> LENGTH: 32
<212> TYPE: DNA
<213> ORGANISM: Artificial
<220> FEATURE:
<223> OTHER INFORMATION: Allele Probe 2

<400> SEQUENCE: 83
cgcgccgagg ataatgctgg gttaattgta gt                                         32

<210> SEQ ID NO 84
<211> LENGTH: 26
<212> TYPE: DNA
<213> ORGANISM: Artificial
<220> FEATURE:
<223> OTHER INFORMATION: Forward Primer

<400> SEQUENCE: 84
catgactgac tatggaagaa gacaaa                                                26
```

<210> SEQ ID NO 85
<211> LENGTH: 21
<212> TYPE: DNA
<213> ORGANISM: Artificial
<220> FEATURE:
<223> OTHER INFORMATION: Reverse Primer

<400> SEQUENCE: 85
tgtctccaat acctctggcc a                                              21

<210> SEQ ID NO 86
<211> LENGTH: 31
<212> TYPE: DNA
<213> ORGANISM: Artificial
<220> FEATURE:
<223> OTHER INFORMATION: Invader Probe

<400> SEQUENCE: 86
atacaggagc tggagtcaaa gctggtgagc t                                   31

<210> SEQ ID NO 87
<211> LENGTH: 34
<212> TYPE: DNA
<213> ORGANISM: Artificial
<220> FEATURE:
<223> OTHER INFORMATION: Allele Probe 1

<400> SEQUENCE: 87
atgacgtggc agacgatcca ggcttatgaa gatg                                34

<210> SEQ ID NO 88
<211> LENGTH: 31
<212> TYPE: DNA
<213> ORGANISM: Artificial
<220> FEATURE:
<223> OTHER INFORMATION: Allele Probe 2

<400> SEQUENCE: 88
cgcgccgagg aatccaggct tatgaagatg c                                   31

<210> SEQ ID NO 89
<211> LENGTH: 33
<212> TYPE: DNA
<213> ORGANISM: Artificial
<220> FEATURE:
<223> OTHER INFORMATION: Forward Primer

<400> SEQUENCE: 89
ctaaaaaacc attaagtttt atagcataca gtg                                 33

<210> SEQ ID NO 90
<211> LENGTH: 24
<212> TYPE: DNA
<213> ORGANISM: Artificial
<220> FEATURE:
<223> OTHER INFORMATION: Reverse Primer

<400> SEQUENCE: 90
aaaatctaac aaattctgca gggc                                           24

<210> SEQ ID NO 91
<211> LENGTH: 44
<212> TYPE: DNA
<213> ORGANISM: Artificial
<220> FEATURE:

<223> OTHER INFORMATION: Invader Probe

<400> SEQUENCE: 91
tacagtcaaa aactggtaac agccaaaatg gccatcaata ctga                44

<210> SEQ ID NO 92
<211> LENGTH: 38
<212> TYPE: DNA
<213> ORGANISM: Artificial
<220> FEATURE:
<223> OTHER INFORMATION: Allele Probe 1

<400> SEQUENCE: 92
cgcgccgagg tataaattac tgtctatcta tgcaatag                       38

<210> SEQ ID NO 93
<211> LENGTH: 41
<212> TYPE: DNA
<213> ORGANISM: Artificial
<220> FEATURE:
<223> OTHER INFORMATION: Allele Probe 2

<400> SEQUENCE: 93
atgacgtggc agaccataaa ttactgtcta tctatgcaat a                   41

<210> SEQ ID NO 94
<211> LENGTH: 23
<212> TYPE: DNA
<213> ORGANISM: Artificial
<220> FEATURE:
<223> OTHER INFORMATION: Forward Primer

<400> SEQUENCE: 94
cagaaagctg aaaaggcttg aaa                                       23

<210> SEQ ID NO 95
<211> LENGTH: 32
<212> TYPE: DNA
<213> ORGANISM: Artificial
<220> FEATURE:
<223> OTHER INFORMATION: Reverse Primer

<400> SEQUENCE: 95
tgtctatttg attcttctct cttcttcttt ac                             32

<210> SEQ ID NO 96
<211> LENGTH: 52
<212> TYPE: DNA
<213> ORGANISM: Artificial
<220> FEATURE:
<223> OTHER INFORMATION: Invader Probe

<400> SEQUENCE: 96
gagctagaaa cacgaaaaac ccttcaaaaa aatcaatgaa tccagaagct gt        52

<210> SEQ ID NO 97
<211> LENGTH: 40
<212> TYPE: DNA
<213> ORGANISM: Artificial
<220> FEATURE:
<223> OTHER INFORMATION: Allele Probe 1

<400> SEQUENCE: 97
atgacgtggc agacgctttt tcaaaacatt aacaagatag                     40

<210> SEQ ID NO 98
<211> LENGTH: 36
<212> TYPE: DNA
<213> ORGANISM: Artificial
<220> FEATURE:
<223> OTHER INFORMATION: Allele Probe 2

<400> SEQUENCE: 98
cgcgccgagg cctttttcaa aacattaaca agatag                          36

<210> SEQ ID NO 99
<211> LENGTH: 28
<212> TYPE: DNA
<213> ORGANISM: Artificial
<220> FEATURE:
<223> OTHER INFORMATION: Forward Primer

<400> SEQUENCE: 99
ctaacatgta taatcaacac agagtggc                                   28

<210> SEQ ID NO 100
<211> LENGTH: 27
<212> TYPE: DNA
<213> ORGANISM: Artificial
<220> FEATURE:
<223> OTHER INFORMATION: Reverse Primer

<400> SEQUENCE: 100
agaatgagtg ttattcccat atggaca                                    27

<210> SEQ ID NO 101
<211> LENGTH: 39
<212> TYPE: DNA
<213> ORGANISM: Artificial
<220> FEATURE:
<223> OTHER INFORMATION: Invader Probe

<400> SEQUENCE: 101
cctgctggcc tcaaatcata ctatataagt cccagaact                       39

<210> SEQ ID NO 102
<211> LENGTH: 38
<212> TYPE: DNA
<213> ORGANISM: Artificial
<220> FEATURE:
<223> OTHER INFORMATION: Allele Probe 1

<400> SEQUENCE: 102
atgacgtggc agacgaataa ttcactcttt ttgtgtac                        38

<210> SEQ ID NO 103
<211> LENGTH: 35
<212> TYPE: DNA
<213> ORGANISM: Artificial
<220> FEATURE:
<223> OTHER INFORMATION: Allele Probe 2

<400> SEQUENCE: 103
cgcgccgagg aaataattca ctcttttgt gtacc                            35

<210> SEQ ID NO 104
<211> LENGTH: 21
<212> TYPE: DNA
<213> ORGANISM: Artificial
<220> FEATURE:
<223> OTHER INFORMATION: Forward Primer

<400> SEQUENCE: 104
gactgagcct gcatgtcacc t                                              21

<210> SEQ ID NO 105
<211> LENGTH: 23
<212> TYPE: DNA
<213> ORGANISM: Artificial
<220> FEATURE:
<223> OTHER INFORMATION: Reverse Primer

<400> SEQUENCE: 105
gacccatatt tgcaggacaa gat                                            23

<210> SEQ ID NO 106
<211> LENGTH: 40
<212> TYPE: DNA
<213> ORGANISM: Artificial
<220> FEATURE:
<223> OTHER INFORMATION: Invader Probe

<400> SEQUENCE: 106
ctccacctgt agatccattt caacaactga ttaggtgcca                          40

<210> SEQ ID NO 107
<211> LENGTH: 41
<212> TYPE: DNA
<213> ORGANISM: Artificial
<220> FEATURE:
<223> OTHER INFORMATION: Allele Probe 1

<400> SEQUENCE: 107
atgacgtggc agaccgaagc atttatatgt ctataaattt c                        41

<210> SEQ ID NO 108
<211> LENGTH: 38
<212> TYPE: DNA
<213> ORGANISM: Artificial
<220> FEATURE:
<223> OTHER INFORMATION: Allele Probe 2

<400> SEQUENCE: 108
cgcgccgagg tgaagcattt atatgtctat aaatttct                            38

<210> SEQ ID NO 109
<211> LENGTH: 30
<212> TYPE: DNA
<213> ORGANISM: Artificial
<220> FEATURE:
<223> OTHER INFORMATION: Forward Primer

<400> SEQUENCE: 109
tttgtaaatt tggcatatag gttagaagat                                     30

<210> SEQ ID NO 110
<211> LENGTH: 25
<212> TYPE: DNA
<213> ORGANISM: Artificial
<220> FEATURE:
<223> OTHER INFORMATION: Reverse Primer

<400> SEQUENCE: 110
cacctgaaaa ttgaaccaaa gactg                                          25

<210> SEQ ID NO 111
<211> LENGTH: 65

-continued

<210> SEQ ID NO 112
<211> LENGTH: 41
<212> TYPE: DNA
<213> ORGANISM: Artificial
<220> FEATURE:
<223> OTHER INFORMATION: Invader Probe

<400> SEQUENCE: 111
ggcatatagg ttagaagata atatgatatc ttatatgaac ttaaagtatt cttacagtga    60
atagt    65

<210> SEQ ID NO 112
<211> LENGTH: 41
<212> TYPE: DNA
<213> ORGANISM: Artificial
<220> FEATURE:
<223> OTHER INFORMATION: Allele Probe 1

<400> SEQUENCE: 112
cgcgccgagg aaaaaggaat attactgaaa tcaaaataac c    41

<210> SEQ ID NO 113
<211> LENGTH: 44
<212> TYPE: DNA
<213> ORGANISM: Artificial
<220> FEATURE:
<223> OTHER INFORMATION: Allele Probe 2

<400> SEQUENCE: 113
atgacgtggc agacgaaaag gaatattact gaaatcaaaa taac    44

<210> SEQ ID NO 114
<211> LENGTH: 26
<212> TYPE: DNA
<213> ORGANISM: Artificial
<220> FEATURE:
<223> OTHER INFORMATION: Forward Primer

<400> SEQUENCE: 114
aggacatggt aataagcaac ttttga    26

<210> SEQ ID NO 115
<211> LENGTH: 18
<212> TYPE: DNA
<213> ORGANISM: Artificial
<220> FEATURE:
<223> OTHER INFORMATION: Reverse Primer

<400> SEQUENCE: 115
ccaccagcca actcaggg    18

<210> SEQ ID NO 116
<211> LENGTH: 55
<212> TYPE: DNA
<213> ORGANISM: Artificial
<220> FEATURE:
<223> OTHER INFORMATION: Invader Probe

<400> SEQUENCE: 116
ggacatggta ataagcaact tttgatgaat ttacattgtg tgggctttat gtcac    55

<210> SEQ ID NO 117
<211> LENGTH: 34
<212> TYPE: DNA
<213> ORGANISM: Artificial
<220> FEATURE:
<223> OTHER INFORMATION: Allele Probe 1

```
<400> SEQUENCE: 117
cgcgccgagg attacttatt cagattcatg atcc                              34

<210> SEQ ID NO 118
<211> LENGTH: 38
<212> TYPE: DNA
<213> ORGANISM: Artificial
<220> FEATURE:
<223> OTHER INFORMATION: Allele Probe 2

<400> SEQUENCE: 118
atgacgtggc agactttact tattcagatt catgatcc                          38

<210> SEQ ID NO 119
<211> LENGTH: 27
<212> TYPE: DNA
<213> ORGANISM: Artificial
<220> FEATURE:
<223> OTHER INFORMATION: Forward Primer

<400> SEQUENCE: 119
ggaggtgaga gaaagtgata taaccag                                       27

<210> SEQ ID NO 120
<211> LENGTH: 30
<212> TYPE: DNA
<213> ORGANISM: Artificial
<220> FEATURE:
<223> OTHER INFORMATION: Reverse primer

<400> SEQUENCE: 120
tgtaagttta tgattttggc ttctctaaaa                                    30

<210> SEQ ID NO 121
<211> LENGTH: 44
<212> TYPE: DNA
<213> ORGANISM: Artificial
<220> FEATURE:
<223> OTHER INFORMATION: Invader Probe

<400> SEQUENCE: 121
gagccttgat gtttgatgtc ttagagttat cagcccaagt ctat                    44

<210> SEQ ID NO 122
<211> LENGTH: 45
<212> TYPE: DNA
<213> ORGANISM: Artificial
<220> FEATURE:
<223> OTHER INFORMATION: Allele Probe 1

<400> SEQUENCE: 122
atgacgtggc agacgtaaac attctttttg attatcacta taata                   45

<210> SEQ ID NO 123
<211> LENGTH: 42
<212> TYPE: DNA
<213> ORGANISM: Artificial
<220> FEATURE:
<223> OTHER INFORMATION: Allele Probe 2

<400> SEQUENCE: 123
cgcgccgagg ataaacattc ttttgatta tcactataat ag                       42

<210> SEQ ID NO 124
<211> LENGTH: 25
```

```
<212> TYPE: DNA
<213> ORGANISM: Artificial
<220> FEATURE:
<223> OTHER INFORMATION: Forward Primer

<400> SEQUENCE: 124
gaaggaggag gatatagaaa ggtgg                                    25

<210> SEQ ID NO 125
<211> LENGTH: 28
<212> TYPE: DNA
<213> ORGANISM: Artificial
<220> FEATURE:
<223> OTHER INFORMATION: Reverse Primer

<400> SEQUENCE: 125
ttaacattat tctttgccta tcaggaaa                                 28

<210> SEQ ID NO 126
<211> LENGTH: 40
<212> TYPE: DNA
<213> ORGANISM: Artificial
<220> FEATURE:
<223> OTHER INFORMATION: Invader Probe

<400> SEQUENCE: 126
ggatttgctt tccaatcttc tctaccctgt ttgacaacct                    40

<210> SEQ ID NO 127
<211> LENGTH: 29
<212> TYPE: DNA
<213> ORGANISM: Artificial
<220> FEATURE:
<223> OTHER INFORMATION: Allele Probe 1

<400> SEQUENCE: 127
cgcgccgagg aaagagggtg gcttctatg                                29

<210> SEQ ID NO 128
<211> LENGTH: 32
<212> TYPE: DNA
<213> ORGANISM: Artificial
<220> FEATURE:
<223> OTHER INFORMATION: Allele Probe 2

<400> SEQUENCE: 128
atgacgtggc agaccaagag ggtggcttct at                            32

<210> SEQ ID NO 129
<211> LENGTH: 27
<212> TYPE: DNA
<213> ORGANISM: Artificial
<220> FEATURE:
<223> OTHER INFORMATION: Forward Primer

<400> SEQUENCE: 129
tggatccata aaataggaa aaactga                                   27

<210> SEQ ID NO 130
<211> LENGTH: 21
<212> TYPE: DNA
<213> ORGANISM: Artificial
<220> FEATURE:
<223> OTHER INFORMATION: Reverse Primer

<400> SEQUENCE: 130
```
tcagatttca tcacagtcgc g                     21

<210> SEQ ID NO 131
<211> LENGTH: 31
<212> TYPE: DNA
<213> ORGANISM: Artificial
<220> FEATURE:
<223> OTHER INFORMATION: Invader Probe

<400> SEQUENCE: 131
ggatccacag agaatcctga tcagcaggac a           31

<210> SEQ ID NO 132
<211> LENGTH: 26
<212> TYPE: DNA
<213> ORGANISM: Artificial
<220> FEATURE:
<223> OTHER INFORMATION: Allele Probe 1

<400> SEQUENCE: 132
cgcgccgagg taggctggac ccacag                26

<210> SEQ ID NO 133
<211> LENGTH: 28
<212> TYPE: DNA
<213> ORGANISM: Artificial
<220> FEATURE:
<223> OTHER INFORMATION: Allele Probe 2

<400> SEQUENCE: 133
atgacgtggc agaccaggct ggacccac              28

<210> SEQ ID NO 134
<211> LENGTH: 21
<212> TYPE: DNA
<213> ORGANISM: Artificial
<220> FEATURE:
<223> OTHER INFORMATION: Forward Primer

<400> SEQUENCE: 134
tccagttggt tcttgcgagt g                     21

<210> SEQ ID NO 135
<211> LENGTH: 27
<212> TYPE: DNA
<213> ORGANISM: Artificial
<220> FEATURE:
<223> OTHER INFORMATION: Reverse Primer

<400> SEQUENCE: 135
gtgctagttc tacataaaag caacagc               27

<210> SEQ ID NO 136
<211> LENGTH: 21
<212> TYPE: DNA
<213> ORGANISM: Artificial
<220> FEATURE:
<223> OTHER INFORMATION: Invader Probe

<400> SEQUENCE: 136
tccagttggt tcttgcgagt g                     21

<210> SEQ ID NO 137
<211> LENGTH: 38
<212> TYPE: DNA
<213> ORGANISM: Artificial

```
<220> FEATURE:
<223> OTHER INFORMATION: Allele Probe 1

<400> SEQUENCE: 137
cgcgccgagg atgtattagt gagagagtta tttaaaag                          38

<210> SEQ ID NO 138
<211> LENGTH: 41
<212> TYPE: DNA
<213> ORGANISM: Artificial
<220> FEATURE:
<223> OTHER INFORMATION: Allele Probe 2

<400> SEQUENCE: 138
atgacgtggc agacgtgtat tagtgagaga gttatttaaa a                      41

<210> SEQ ID NO 139
<211> LENGTH: 23
<212> TYPE: DNA
<213> ORGANISM: Artificial
<220> FEATURE:
<223> OTHER INFORMATION: Forward Primer

<400> SEQUENCE: 139
tggttcataa tgcatggtct cct                                          23

<210> SEQ ID NO 140
<211> LENGTH: 23
<212> TYPE: DNA
<213> ORGANISM: Artificial
<220> FEATURE:
<223> OTHER INFORMATION: Reverse Primer

<400> SEQUENCE: 140
ggtgtcagtt ctgtgtccaa ggt                                          23

<210> SEQ ID NO 141
<211> LENGTH: 34
<212> TYPE: DNA
<213> ORGANISM: Artificial
<220> FEATURE:
<223> OTHER INFORMATION: Invader Probe

<400> SEQUENCE: 141
gacctctctc tactgccaca caagttctgt gctt                              34

<210> SEQ ID NO 142
<211> LENGTH: 35
<212> TYPE: DNA
<213> ORGANISM: Artificial
<220> FEATURE:
<223> OTHER INFORMATION: Allele Probe 1

<400> SEQUENCE: 142
atgacgtggc agacgacatg ggaataacat tagga                             35

<210> SEQ ID NO 143
<211> LENGTH: 32
<212> TYPE: DNA
<213> ORGANISM: Artificial
<220> FEATURE:
<223> OTHER INFORMATION: Allele Probe 2

<400> SEQUENCE: 143
cgcgccgagg aacatgggaa taacattagg at                                32
```

<210> SEQ ID NO 144
<211> LENGTH: 23
<212> TYPE: DNA
<213> ORGANISM: Artificial
<220> FEATURE:
<223> OTHER INFORMATION: Forward Primer

<400> SEQUENCE: 144
tggttcataa tgcatggtct cct                                           23

<210> SEQ ID NO 145
<211> LENGTH: 23
<212> TYPE: DNA
<213> ORGANISM: Artificial
<220> FEATURE:
<223> OTHER INFORMATION: Reverse Primer

<400> SEQUENCE: 145
ggtgtcagtt ctgtgtccaa ggt                                           23

<210> SEQ ID NO 146
<211> LENGTH: 35
<212> TYPE: DNA
<213> ORGANISM: Artificial
<220> FEATURE:
<223> OTHER INFORMATION: Invader Probe

<400> SEQUENCE: 146
ggcctgaaat tttctctcag ggggaggaat tcagt                              35

<210> SEQ ID NO 147
<211> LENGTH: 33
<212> TYPE: DNA
<213> ORGANISM: Artificial
<220> FEATURE:
<223> OTHER INFORMATION: Allele Probe 1

<400> SEQUENCE: 147
atgacgtggc agacgtatgc aaagaggtgg ttg                                33

<210> SEQ ID NO 148
<211> LENGTH: 30
<212> TYPE: DNA
<213> ORGANISM: Artificial
<220> FEATURE:
<223> OTHER INFORMATION: Allele Probe 2

<400> SEQUENCE: 148
cgcgccgagg atatgcaaag aggtggttgt                                    30

<210> SEQ ID NO 149
<211> LENGTH: 22
<212> TYPE: DNA
<213> ORGANISM: Artificial
<220> FEATURE:
<223> OTHER INFORMATION: Forward Primer

<400> SEQUENCE: 149
gtgtcacaac cacctctttg ca                                            22

<210> SEQ ID NO 150
<211> LENGTH: 21
<212> TYPE: DNA
<213> ORGANISM: Artificial
<220> FEATURE:
<223> OTHER INFORMATION: Reverse Primer

```
<400> SEQUENCE: 150
tccaaggttg agatggttgg a                                      21

<210> SEQ ID NO 151
<211> LENGTH: 35
<212> TYPE: DNA
<213> ORGANISM: Artificial
<220> FEATURE:
<223> OTHER INFORMATION: Invader Probe

<400> SEQUENCE: 151
gggtcctcaa atccagtttg aaatccagtt cttga                       35

<210> SEQ ID NO 152
<211> LENGTH: 28
<212> TYPE: DNA
<213> ORGANISM: Artificial
<220> FEATURE:
<223> OTHER INFORMATION: Allele Probe 1

<400> SEQUENCE: 152
cgcgccgagg ttgactctga agcctgac                               28

<210> SEQ ID NO 153
<211> LENGTH: 31
<212> TYPE: DNA
<213> ORGANISM: Artificial
<220> FEATURE:
<223> OTHER INFORMATION: Allele Probe 2

<400> SEQUENCE: 153
atgacgtggc agacctgact ctgaagcctg a                           31

<210> SEQ ID NO 154
<211> LENGTH: 20
<212> TYPE: DNA
<213> ORGANISM: Artificial
<220> FEATURE:
<223> OTHER INFORMATION: Forward Primer

<400> SEQUENCE: 154
ccaaaataga actggggcac                                        20

<210> SEQ ID NO 155
<211> LENGTH: 21
<212> TYPE: DNA
<213> ORGANISM: Artificial
<220> FEATURE:
<223> OTHER INFORMATION: Reverse Primer

<400> SEQUENCE: 155
ccctgtcatt tgttcacagc a                                      21

<210> SEQ ID NO 156
<211> LENGTH: 39
<212> TYPE: DNA
<213> ORGANISM: Artificial
<220> FEATURE:
<223> OTHER INFORMATION: Invader Probe

<400> SEQUENCE: 156
tcactggtcc attagtccag gaagagctaa ataagcaca                   39

<210> SEQ ID NO 157
```

```
<211> LENGTH: 35
<212> TYPE: DNA
<213> ORGANISM: Artificial
<220> FEATURE:
<223> OTHER INFORMATION: Allele Probe 1

<400> SEQUENCE: 157
atgacgtggc agacgtaaaa gttctcaagg ggaag                              35

<210> SEQ ID NO 158
<211> LENGTH: 32
<212> TYPE: DNA
<213> ORGANISM: Artificial
<220> FEATURE:
<223> OTHER INFORMATION: Allele Probe 2

<400> SEQUENCE: 158
cgcgccgagg ttaaaagttc tcaaggggaa gg                                 32

<210> SEQ ID NO 159
<211> LENGTH: 22
<212> TYPE: DNA
<213> ORGANISM: Artificial
<220> FEATURE:
<223> OTHER INFORMATION: Forward Primer

<400> SEQUENCE: 159
ttcccaggtg aggacaaact tt                                            22

<210> SEQ ID NO 160
<211> LENGTH: 21
<212> TYPE: DNA
<213> ORGANISM: Artificial
<220> FEATURE:
<223> OTHER INFORMATION: Reverse Primer

<400> SEQUENCE: 160
caggcaagga gctttgatgt g                                             21

<210> SEQ ID NO 161
<211> LENGTH: 29
<212> TYPE: DNA
<213> ORGANISM: Artificial
<220> FEATURE:
<223> OTHER INFORMATION: Invader Probe

<400> SEQUENCE: 161
cccagagtgg actctcccaa taaccctct                                     29

<210> SEQ ID NO 162
<211> LENGTH: 29
<212> TYPE: DNA
<213> ORGANISM: Artificial
<220> FEATURE:
<223> OTHER INFORMATION: Allele Probe 1

<400> SEQUENCE: 162
cgcgccgagg agcctgaact gaagacatc                                     29

<210> SEQ ID NO 163
<211> LENGTH: 32
<212> TYPE: DNA
<213> ORGANISM: Artificial
<220> FEATURE:
<223> OTHER INFORMATION: Allele Probe 2

<400> SEQUENCE: 163
```

```
atgacgtggc agacggcctg aactgaagac at                                    32

<210> SEQ ID NO 164
<211> LENGTH: 27
<212> TYPE: DNA
<213> ORGANISM: Artificial
<220> FEATURE:
<223> OTHER INFORMATION: Forward Primer

<400> SEQUENCE: 164
ccgctactga cactacttac tcatcaa                                          27

<210> SEQ ID NO 165
<211> LENGTH: 23
<212> TYPE: DNA
<213> ORGANISM: Artificial
<220> FEATURE:
<223> OTHER INFORMATION: Reverse Primer

<400> SEQUENCE: 165
aacattggca aaacatgaaa agg                                              23

<210> SEQ ID NO 166
<211> LENGTH: 45
<212> TYPE: DNA
<213> ORGANISM: Artificial
<220> FEATURE:
<223> OTHER INFORMATION: Invader Probe

<400> SEQUENCE: 166
caatgactcc atggcttgga attctggaat atcataatct cctct                      45

<210> SEQ ID NO 167
<211> LENGTH: 28
<212> TYPE: DNA
<213> ORGANISM: Artificial
<220> FEATURE:
<223> OTHER INFORMATION: Allele Probe 1

<400> SEQUENCE: 167
cgcgccgagg attttcttct tcccccgc                                         28

<210> SEQ ID NO 168
<211> LENGTH: 31
<212> TYPE: DNA
<213> ORGANISM: Artificial
<220> FEATURE:
<223> OTHER INFORMATION: Allele Probe 2

<400> SEQUENCE: 168
atgacgtggc agacgttttc ttcttccccc g                                     31

<210> SEQ ID NO 169
<211> LENGTH: 18
<212> TYPE: DNA
<213> ORGANISM: Artificial
<220> FEATURE:
<223> OTHER INFORMATION: Forward Primer

<400> SEQUENCE: 169
cccctgcatg tagcacgg                                                    18

<210> SEQ ID NO 170
<211> LENGTH: 25
<212> TYPE: DNA
```

<213> ORGANISM: Artificial
<220> FEATURE:
<223> OTHER INFORMATION: Reverse Primer

<400> SEQUENCE: 170
caaaagaaaa aggaaagaca agggt                                    25

<210> SEQ ID NO 171
<211> LENGTH: 41
<212> TYPE: DNA
<213> ORGANISM: Artificial
<220> FEATURE:
<223> OTHER INFORMATION: Invader Probe

<400> SEQUENCE: 171
ggaggtggaa acacaggaaa gtgatcttgt agctaaaacc t                  41

<210> SEQ ID NO 172
<211> LENGTH: 34
<212> TYPE: DNA
<213> ORGANISM: Artificial
<220> FEATURE:
<223> OTHER INFORMATION: Allele Probe 1

<400> SEQUENCE: 172
cgcgccgagg ataactgact ataaaagaag acag                          34

<210> SEQ ID NO 173
<211> LENGTH: 37
<212> TYPE: DNA
<213> ORGANISM: Artificial
<220> FEATURE:
<223> OTHER INFORMATION: Allele Probe 2

<400> SEQUENCE: 173
atgacgtggc agacgtaact gactataaaa gaagaca                       37

<210> SEQ ID NO 174
<211> LENGTH: 20
<212> TYPE: DNA
<213> ORGANISM: Artificial
<220> FEATURE:
<223> OTHER INFORMATION: Forward Primer

<400> SEQUENCE: 174
ttctaaggcc caaacacccc                                          20

<210> SEQ ID NO 175
<211> LENGTH: 21
<212> TYPE: DNA
<213> ORGANISM: Artificial
<220> FEATURE:
<223> OTHER INFORMATION: Reverse Primer

<400> SEQUENCE: 175
cagtcattaa gggtggccat g                                        21

<210> SEQ ID NO 176
<211> LENGTH: 34
<212> TYPE: DNA
<213> ORGANISM: Artificial
<220> FEATURE:
<223> OTHER INFORMATION: Invader Probe

<400> SEQUENCE: 176
tctaggcaga atatgtgggg cagcaagaga caga                          34

```
<210> SEQ ID NO 177
<211> LENGTH: 33
<212> TYPE: DNA
<213> ORGANISM: Artificial
<220> FEATURE:
<223> OTHER INFORMATION: Allele Probe 1

<400> SEQUENCE: 177
atgacgtggc agacgactct gagttcagca ttc                             33

<210> SEQ ID NO 178
<211> LENGTH: 32
<212> TYPE: DNA
<213> ORGANISM: Artificial
<220> FEATURE:
<223> OTHER INFORMATION: Allele Probe 2

<400> SEQUENCE: 178
cgcgccgagg tactctgagt tcagcattct tt                              32

<210> SEQ ID NO 179
<211> LENGTH: 29
<212> TYPE: DNA
<213> ORGANISM: Artificial
<220> FEATURE:
<223> OTHER INFORMATION: Forward Primer

<400> SEQUENCE: 179
ttaatgatac attgaggact gttaaggtg                                  29

<210> SEQ ID NO 180
<211> LENGTH: 29
<212> TYPE: DNA
<213> ORGANISM: Artificial
<220> FEATURE:
<223> OTHER INFORMATION: Reverse Primer

<400> SEQUENCE: 180
ggaaatccta aaagtgatt gatagctat                                   29

<210> SEQ ID NO 181
<211> LENGTH: 39
<212> TYPE: DNA
<213> ORGANISM: Artificial
<220> FEATURE:
<223> OTHER INFORMATION: Invader Probe

<400> SEQUENCE: 181
cactagaaaa ggactagact gaagggcttt ccattctga                       39

<210> SEQ ID NO 182
<211> LENGTH: 33
<212> TYPE: DNA
<213> ORGANISM: Artificial
<220> FEATURE:
<223> OTHER INFORMATION: Allele Probe 1

<400> SEQUENCE: 182
cgcgccgagg taggtttcag caaatagaat tcc                             33

<210> SEQ ID NO 183
<211> LENGTH: 36
<212> TYPE: DNA
<213> ORGANISM: Artificial
<220> FEATURE:
```

-continued

<223> OTHER INFORMATION: Allele Probe 2

<400> SEQUENCE: 183
atgacgtggc agaccaggtt tcagcaaata gaattc 36

<210> SEQ ID NO 184
<211> LENGTH: 31
<212> TYPE: DNA
<213> ORGANISM: Artificial
<220> FEATURE:
<223> OTHER INFORMATION: Forward Primer

<400> SEQUENCE: 184
cagaaagtga gaaatacat gaaagtctct c 31

<210> SEQ ID NO 185
<211> LENGTH: 23
<212> TYPE: DNA
<213> ORGANISM: Artificial
<220> FEATURE:
<223> OTHER INFORMATION: Reverse Primer

<400> SEQUENCE: 185
ttgcttggca tcagtcactg tat 23

<210> SEQ ID NO 186
<211> LENGTH: 51
<212> TYPE: DNA
<213> ORGANISM: Artificial
<220> FEATURE:
<223> OTHER INFORMATION: Invader Probe

<400> SEQUENCE: 186
caaacattga atcgtaatta atcaagcgct gtgctaattc tacataaaag t 51

<210> SEQ ID NO 187
<211> LENGTH: 37
<212> TYPE: DNA
<213> ORGANISM: Artificial
<220> FEATURE:
<223> OTHER INFORMATION: Allele Probe 1

<400> SEQUENCE: 187
cgcgccgagg aaaacatctt tcaaataagt ctctcac 37

<210> SEQ ID NO 188
<211> LENGTH: 39
<212> TYPE: DNA
<213> ORGANISM: Artificial
<220> FEATURE:
<223> OTHER INFORMATION: Allele Probe 2

<400> SEQUENCE: 188
atgacgtggc agaccaaaca tctttcaaat aagtctctc 39

<210> SEQ ID NO 189
<211> LENGTH: 24
<212> TYPE: DNA
<213> ORGANISM: Artificial
<220> FEATURE:
<223> OTHER INFORMATION: forward primer

<400> SEQUENCE: 189 cagctcccctt tataagggaa gggt 24

```
<210> SEQ ID NO 190
<211> LENGTH: 21
<212> TYPE: DNA
<213> ORGANISM: Artificial
<220> FEATURE:
<223> OTHER INFORMATION: reverse primer

<400> SEQUENCE: 190
tcagcagaag ggactttgta c                                              21

<210> SEQ ID NO 191
<211> LENGTH: 23
<212> TYPE: DNA
<213> ORGANISM: Artificial
<220> FEATURE:
<223> OTHER INFORMATION: forward primer

<400> SEQUENCE: 191
ccaaactgag ttcctccatc aca                                            23

<210> SEQ ID NO 192
<211> LENGTH: 20
<212> TYPE: DNA
<213> ORGANISM: Artificial
<220> FEATURE:
<223> OTHER INFORMATION: reverse primer

<400> SEQUENCE: 192
tcgctggcct gtttcatgtc                                                20

<210> SEQ ID NO 193
<211> LENGTH: 20
<212> TYPE: DNA
<213> ORGANISM: Artificial
<220> FEATURE:
<223> OTHER INFORMATION: forward primer

<400> SEQUENCE: 193
agagacgagg tggggcaaag                                                20

<210> SEQ ID NO 194
<211> LENGTH: 18
<212> TYPE: DNA
<213> ORGANISM: Artificial
<220> FEATURE:
<223> OTHER INFORMATION: reverse primer

<400> SEQUENCE: 194
ttgctcacgg ctttgtcc                                                  18

<210> SEQ ID NO 195
<211> LENGTH: 18
<212> TYPE: DNA
<213> ORGANISM: Artificial
<220> FEATURE:
<223> OTHER INFORMATION: forward primer

<400> SEQUENCE: 195
acaaagcggg aactggga                                                  18

<210> SEQ ID NO 196
<211> LENGTH: 22
<212> TYPE: DNA
<213> ORGANISM: Artificial
<220> FEATURE:
<223> OTHER INFORMATION: reverse primer
```

```
<400> SEQUENCE: 196
tgtctgagat gtcccctcct cc                                              22

<210> SEQ ID NO 197
<211> LENGTH: 22
<212> TYPE: DNA
<213> ORGANISM: Artificial
<220> FEATURE:
<223> OTHER INFORMATION: forward primer

<400> SEQUENCE: 197
ttggtgaggt cagtggtaag ga                                              22

<210> SEQ ID NO 198
<211> LENGTH: 19
<212> TYPE: DNA
<213> ORGANISM: Artificial
<220> FEATURE:
<223> OTHER INFORMATION: reverse primer

<400> SEQUENCE: 198
cccccaaatg acctccaat                                                  19

<210> SEQ ID NO 199
<211> LENGTH: 22
<212> TYPE: DNA
<213> ORGANISM: Artificial
<220> FEATURE:
<223> OTHER INFORMATION: forward primer

<400> SEQUENCE: 199
tgacaggtgc agaattggag gt                                              22

<210> SEQ ID NO 200
<211> LENGTH: 23
<212> TYPE: DNA
<213> ORGANISM: Artificial
<220> FEATURE:
<223> OTHER INFORMATION: reverse primer

<400> SEQUENCE: 200
aacaggagat cgacgacgtg ata                                             23

<210> SEQ ID NO 201
<211> LENGTH: 20
<212> TYPE: DNA
<213> ORGANISM: Artificial
<220> FEATURE:
<223> OTHER INFORMATION: forward primer

<400> SEQUENCE: 201
atcctgtaag cctgacctcc                                                 20

<210> SEQ ID NO 202
<211> LENGTH: 20
<212> TYPE: DNA
<213> ORGANISM: Artificial
<220> FEATURE:
<223> OTHER INFORMATION: reverse primer

<400> SEQUENCE: 202
cagtgtggtg gcattgagga                                                 20

<210> SEQ ID NO 203
<211> LENGTH: 18
```

```
<212> TYPE: DNA
<213> ORGANISM: Artificial
<220> FEATURE:
<223> OTHER INFORMATION: forward primer

<400> SEQUENCE: 203
gtcccccgtg tgtttggt                                                 18

<210> SEQ ID NO 204
<211> LENGTH: 20
<212> TYPE: DNA
<213> ORGANISM: Artificial
<220> FEATURE:
<223> OTHER INFORMATION: reverse primer

<400> SEQUENCE: 204
gggaggtgaa gaagaggaag                                               20

<210> SEQ ID NO 205
<211> LENGTH: 19
<212> TYPE: DNA
<213> ORGANISM: Artificial
<220> FEATURE:
<223> OTHER INFORMATION: forward primer

<400> SEQUENCE: 205
ccttcctgcc tttctcagc                                                19

<210> SEQ ID NO 206
<211> LENGTH: 20
<212> TYPE: DNA
<213> ORGANISM: Artificial
<220> FEATURE:
<223> OTHER INFORMATION: reverse primer

<400> SEQUENCE: 206
ggtaagcagg aatgaggcag                                               20

<210> SEQ ID NO 207
<211> LENGTH: 28
<212> TYPE: DNA
<213> ORGANISM: Artificial
<220> FEATURE:
<223> OTHER INFORMATION: forward primer

<400> SEQUENCE: 207
gttatcccag aaggctttgc aggcttca                                      28

<210> SEQ ID NO 208
<211> LENGTH: 23
<212> TYPE: DNA
<213> ORGANISM: Artificial
<220> FEATURE:
<223> OTHER INFORMATION: reverse primer

<400> SEQUENCE: 208
cactcgctgg cctgtttcat gtc                                           23

<210> SEQ ID NO 209
<211> LENGTH: 22
<212> TYPE: DNA
<213> ORGANISM: Artificial
<220> FEATURE:
<223> OTHER INFORMATION: forward primer

<400> SEQUENCE: 209
```

```
ctggaatccg gtgtcgaagt gg                                              22

<210> SEQ ID NO 210
<211> LENGTH: 20
<212> TYPE: DNA
<213> ORGANISM: Artificial
<220> FEATURE:
<223> OTHER INFORMATION: reverse primer

<400> SEQUENCE: 210
ctcggcccct gcactgtttc                                                 20

<210> SEQ ID NO 211
<211> LENGTH: 22
<212> TYPE: DNA
<213> ORGANISM: Artificial
<220> FEATURE:
<223> OTHER INFORMATION: forward primer

<400> SEQUENCE: 211
gaggcaagaa ggagtgtcag gg                                              22

<210> SEQ ID NO 212
<211> LENGTH: 23
<212> TYPE: DNA
<213> ORGANISM: Artificial
<220> FEATURE:
<223> OTHER INFORMATION: reverse primer

<400> SEQUENCE: 212
gggtaagcag gaatgaggca ggg                                             23

<210> SEQ ID NO 213
<211> LENGTH: 19
<212> TYPE: DNA
<213> ORGANISM: Artificial
<220> FEATURE:
<223> OTHER INFORMATION: Invader probe

<400> SEQUENCE: 213
gctgggtccc aggtcatct                                                  19

<210> SEQ ID NO 214
<211> LENGTH: 27
<212> TYPE: DNA
<213> ORGANISM: Artificial
<220> FEATURE:
<223> OTHER INFORMATION: allele probe

<400> SEQUENCE: 214
cgcgccgagg ctgtgctcag ttagcag                                         27

<210> SEQ ID NO 215
<211> LENGTH: 30
<212> TYPE: DNA
<213> ORGANISM: Artificial
<220> FEATURE:
<223> OTHER INFORMATION: allele probe

<400> SEQUENCE: 215
atgacgtggc agaccgtgct cagttagcag                                      30

<210> SEQ ID NO 216
<211> LENGTH: 25
<212> TYPE: DNA
<213> ORGANISM: Artificial
```

```
<220> FEATURE:
<223> OTHER INFORMATION: Invader probe

<400> SEQUENCE: 216
ccttacccgc atctcccacc cccat                                              25

<210> SEQ ID NO 217
<211> LENGTH: 24
<212> TYPE: DNA
<213> ORGANISM: Artificial
<220> FEATURE:
<223> OTHER INFORMATION: allele probe

<400> SEQUENCE: 217
cgcgccgagg agacgcccct ttcg                                               24

<210> SEQ ID NO 218
<211> LENGTH: 28
<212> TYPE: DNA
<213> ORGANISM: Artificial
<220> FEATURE:
<223> OTHER INFORMATION: allele probe

<400> SEQUENCE: 218
atgacgtggc agacggacgc ccctttcg                                           28

<210> SEQ ID NO 219
<211> LENGTH: 17
<212> TYPE: DNA
<213> ORGANISM: Artificial
<220> FEATURE:
<223> OTHER INFORMATION: Invader probe

<400> SEQUENCE: 219
ggcctcctcg gtcacct                                                       17

<210> SEQ ID NO 220
<211> LENGTH: 23
<212> TYPE: DNA
<213> ORGANISM: Artificial
<220> FEATURE:
<223> OTHER INFORMATION: allele probe

<400> SEQUENCE: 220
cgcgccgagg cactgctcca gcg                                                23

<210> SEQ ID NO 221
<211> LENGTH: 27
<212> TYPE: DNA
<213> ORGANISM: Artificial
<220> FEATURE:
<223> OTHER INFORMATION: allele probe

<400> SEQUENCE: 221
atgacgtggc agaccctgct ccagcga                                            27

<210> SEQ ID NO 222
<211> LENGTH: 17
<212> TYPE: DNA
<213> ORGANISM: Artificial
<220> FEATURE:
<223> OTHER INFORMATION: Invader probe

<400> SEQUENCE: 222
acgctgcaca tccggrc                                                       17
```

```
<210> SEQ ID NO 223
<211> LENGTH: 27
<212> TYPE: DNA
<213> ORGANISM: Artificial
<220> FEATURE:
<223> OTHER INFORMATION: allele probe

<400> SEQUENCE: 223
cgcgccgagg tgtaggatca tgagcag                                        27

<210> SEQ ID NO 224
<211> LENGTH: 31
<212> TYPE: DNA
<213> ORGANISM: Artificial
<220> FEATURE:
<223> OTHER INFORMATION: allele probe

<400> SEQUENCE: 224
atgacgtggc agacggtagg atcatgagca g                                   31

<210> SEQ ID NO 225
<211> LENGTH: 20
<212> TYPE: DNA
<213> ORGANISM: Artificial
<220> FEATURE:
<223> OTHER INFORMATION: Invader probe

<400> SEQUENCE: 225
ccttctgccc atcacccaca                                                20

<210> SEQ ID NO 226
<211> LENGTH: 23
<212> TYPE: DNA
<213> ORGANISM: Artificial
<220> FEATURE:
<223> OTHER INFORMATION: allele probe

<400> SEQUENCE: 226
cgcgccgagg cggagtggtt ggc                                            23

<210> SEQ ID NO 227
<211> LENGTH: 28
<212> TYPE: DNA
<213> ORGANISM: Artificial
<220> FEATURE:
<223> OTHER INFORMATION: allele probe

<400> SEQUENCE: 227
atgacgtggc agacaggagt ggttggcg                                       28

<210> SEQ ID NO 228
<211> LENGTH: 20
<212> TYPE: DNA
<213> ORGANISM: Artificial
<220> FEATURE:
<223> OTHER INFORMATION: Invader probe

<400> SEQUENCE: 228
ggccttcctg gcagagatgt                                                20

<210> SEQ ID NO 229
<211> LENGTH: 26
<212> TYPE: DNA
<213> ORGANISM: Artificial
<220> FEATURE:
<223> OTHER INFORMATION: allele probe
```

```
<400> SEQUENCE: 229
cgcgccgagg gagaaggtga gagtgg                                              26

<210> SEQ ID NO 230
<211> LENGTH: 29
<212> TYPE: DNA
<213> ORGANISM: Artificial
<220> FEATURE:
<223> OTHER INFORMATION: allele probe

<400> SEQUENCE: 230
atgacgtggc agacgaggtg agagtggct                                           29

<210> SEQ ID NO 231
<211> LENGTH: 22
<212> TYPE: DNA
<213> ORGANISM: Artificial
<220> FEATURE:
<223> OTHER INFORMATION: Invader probe

<400> SEQUENCE: 231
gcagtggcag ggggcctggt gt                                                  22

<210> SEQ ID NO 232
<211> LENGTH: 24
<212> TYPE: DNA
<213> ORGANISM: Artificial
<220> FEATURE:
<223> OTHER INFORMATION: allele probe

<400> SEQUENCE: 232
cgcgccgagg agtagcgtgc agcc                                                24

<210> SEQ ID NO 233
<211> LENGTH: 27
<212> TYPE: DNA
<213> ORGANISM: Artificial
<220> FEATURE:
<223> OTHER INFORMATION: allele probe

<400> SEQUENCE: 233
atgacgtggc agacggtagc gtgcagc                                             27

<210> SEQ ID NO 234
<211> LENGTH: 19
<212> TYPE: DNA
<213> ORGANISM: Artificial
<220> FEATURE:
<223> OTHER INFORMATION: Invader probe

<400> SEQUENCE: 234
cccgaagcgg cgccgcaat                                                      19

<210> SEQ ID NO 235
<211> LENGTH: 24
<212> TYPE: DNA
<213> ORGANISM: Artificial
<220> FEATURE:
<223> OTHER INFORMATION: allele probe

<400> SEQUENCE: 235
cgcgccgagg ctgcagaggg aggg                                                24

<210> SEQ ID NO 236
```

-continued

```
<211> LENGTH: 28
<212> TYPE: DNA
<213> ORGANISM: Artificial
<220> FEATURE:
<223> OTHER INFORMATION: allele probe

<400> SEQUENCE: 236
atgacgtggc agacgtgcag agggaggg                                          28

<210> SEQ ID NO 237
<211> LENGTH: 17
<212> TYPE: DNA
<213> ORGANISM: Artificial
<220> FEATURE:
<223> OTHER INFORMATION: Invader probe

<400> SEQUENCE: 237
agcaggttgc ccagcca                                                      17

<210> SEQ ID NO 238
<211> LENGTH: 22
<212> TYPE: DNA
<213> ORGANISM: Artificial
<220> FEATURE:
<223> OTHER INFORMATION: allele probe

<400> SEQUENCE: 238
cgcgccgagg cgggcagtgg ca                                                22

<210> SEQ ID NO 239
<211> LENGTH: 26
<212> TYPE: DNA
<213> ORGANISM: Artificial
<220> FEATURE:
<223> OTHER INFORMATION: allele probe

<400> SEQUENCE: 239
atgacgtggc agactgggca gtggca                                            26

<210> SEQ ID NO 240
<211> LENGTH: 20
<212> TYPE: DNA
<213> ORGANISM: Artificial
<220> FEATURE:
<223> OTHER INFORMATION: Invader probe

<400> SEQUENCE: 240
ccttctgccc atcacccaca                                                   20

<210> SEQ ID NO 241
<211> LENGTH: 23
<212> TYPE: DNA
<213> ORGANISM: Artificial
<220> FEATURE:
<223> OTHER INFORMATION: allele probe

<400> SEQUENCE: 241
cgcgccgagg cggagtggtt ggc                                               23

<210> SEQ ID NO 242
<211> LENGTH: 28
<212> TYPE: DNA
<213> ORGANISM: Artificial
<220> FEATURE:
<223> OTHER INFORMATION: allele probe

<400> SEQUENCE: 242
```
atgacgtggc agactggagt ggttggcg    28

<210> SEQ ID NO 243
<211> LENGTH: 22
<212> TYPE: DNA
<213> ORGANISM: Artificial
<220> FEATURE:
<223> OTHER INFORMATION: Invader probe

<400> SEQUENCE: 243
tgttctggaa gtccacatgc at    22

<210> SEQ ID NO 244
<211> LENGTH: 24
<212> TYPE: DNA
<213> ORGANISM: Artificial
<220> FEATURE:
<223> OTHER INFORMATION: allele probe

<400> SEQUENCE: 244
cgcgccgagg gacaggttgc ccag    24

<210> SEQ ID NO 245
<211> LENGTH: 27
<212> TYPE: DNA
<213> ORGANISM: Artificial
<220> FEATURE:
<223> OTHER INFORMATION: allele probe

<400> SEQUENCE: 245
atgacgtggc agacgcaggt tgcccag    27

<210> SEQ ID NO 246
<211> LENGTH: 22
<212> TYPE: DNA
<213> ORGANISM: Artificial
<220> FEATURE:
<223> OTHER INFORMATION: Invader probe

<400> SEQUENCE: 246
ggcccraarc ccaggatctg gt    22

<210> SEQ ID NO 247
<211> LENGTH: 24
<212> TYPE: DNA
<213> ORGANISM: Artificial
<220> FEATURE:
<223> OTHER INFORMATION: allele probe

<400> SEQUENCE: 247
cgcgccgagg atgatgggca cagg    24

<210> SEQ ID NO 248
<211> LENGTH: 28
<212> TYPE: DNA
<213> ORGANISM: Artificial
<220> FEATURE:
<223> OTHER INFORMATION: allele probe

<400> SEQUENCE: 248
atgacgtggc agacgtgatg ggcacagg    28

<210> SEQ ID NO 249
<211> LENGTH: 18
<212> TYPE: DNA

```
<213> ORGANISM: Artificial
<220> FEATURE:
<223> OTHER INFORMATION: Invader probe

<400> SEQUENCE: 249
agcttctcgg tgcccacc                                                    18

<210> SEQ ID NO 250
<211> LENGTH: 23
<212> TYPE: DNA
<213> ORGANISM: Artificial
<220> FEATURE:
<223> OTHER INFORMATION: allele probe

<400> SEQUENCE: 250
cgcgccgagg tgtgcccact gga                                              23

<210> SEQ ID NO 251
<211> LENGTH: 26
<212> TYPE: DNA
<213> ORGANISM: Artificial
<220> FEATURE:
<223> OTHER INFORMATION: allele probe

<400> SEQUENCE: 251
atgacgtggc agactggaca gccccg                                           26

<210> SEQ ID NO 252
<211> LENGTH: 19
<212> TYPE: DNA
<213> ORGANISM: Artificial
<220> FEATURE:
<223> OTHER INFORMATION: Invader probe

<400> SEQUENCE: 252
cccagctgga tgagctgcc                                                   19

<210> SEQ ID NO 253
<211> LENGTH: 27
<212> TYPE: DNA
<213> ORGANISM: Artificial
<220> FEATURE:
<223> OTHER INFORMATION: allele probe

<400> SEQUENCE: 253
cgcgccgagg taactgagca caggatg                                          27

<210> SEQ ID NO 254
<211> LENGTH: 29
<212> TYPE: DNA
<213> ORGANISM: Artificial
<220> FEATURE:
<223> OTHER INFORMATION: allele probe

<400> SEQUENCE: 254
atgacgtggc agactgagca caggatgac                                        29

<210> SEQ ID NO 255
<211> LENGTH: 20
<212> TYPE: DNA
<213> ORGANISM: Artificial
<220> FEATURE:
<223> OTHER INFORMATION: Invader probe

<400> SEQUENCE: 255
ccgactcctc cttcagtyct                                                  20
```

```
<210> SEQ ID NO 256
<211> LENGTH: 25
<212> TYPE: DNA
<213> ORGANISM: Artificial
<220> FEATURE:
<223> OTHER INFORMATION: allele probe

<400> SEQUENCE: 256
cgcgccgagg cctcctgagc taggt                                        25

<210> SEQ ID NO 257
<211> LENGTH: 30
<212> TYPE: DNA
<213> ORGANISM: Artificial
<220> FEATURE:
<223> OTHER INFORMATION: allele probe

<400> SEQUENCE: 257
atgacgtggc agacctcctg agctaggtcc                                   30

<210> SEQ ID NO 258
<211> LENGTH: 17
<212> TYPE: DNA
<213> ORGANISM: Artificial
<220> FEATURE:
<223> OTHER INFORMATION: Invader probe

<400> SEQUENCE: 258
ctgggaccca gcccagt                                                 17

<210> SEQ ID NO 259
<211> LENGTH: 21
<212> TYPE: DNA
<213> ORGANISM: Artificial
<220> FEATURE:
<223> OTHER INFORMATION: allele probe

<400> SEQUENCE: 259
cgcgccgagg cccccccga g                                             21

<210> SEQ ID NO 260
<211> LENGTH: 26
<212> TYPE: DNA
<213> ORGANISM: Artificial
<220> FEATURE:
<223> OTHER INFORMATION: allele probe

<400> SEQUENCE: 260
atgacgtggc agaccccccc cgagac                                       26

<210> SEQ ID NO 261
<211> LENGTH: 19
<212> TYPE: DNA
<213> ORGANISM: Artificial
<220> FEATURE:
<223> OTHER INFORMATION: Invader probe

<400> SEQUENCE: 261
cagccccggc ccagccaca                                               19

<210> SEQ ID NO 262
<211> LENGTH: 28
<212> TYPE: DNA
<213> ORGANISM: Artificial
<220> FEATURE:
```

-continued

<223> OTHER INFORMATION: allele probe

<400> SEQUENCE: 262
cgcgccgagg tctcgtgtcg tcagcttt                                    28

<210> SEQ ID NO 263
<211> LENGTH: 33
<212> TYPE: DNA
<213> ORGANISM: Artificial
<220> FEATURE:
<223> OTHER INFORMATION: allele probe

<400> SEQUENCE: 263
atgacgtggc agaccatggt gtctttgctt tcc                              33

<210> SEQ ID NO 264
<211> LENGTH: 16
<212> TYPE: DNA
<213> ORGANISM: Artificial
<220> FEATURE:
<223> OTHER INFORMATION: Invader probe

<400> SEQUENCE: 264 agccccccg agaccc                                                  16

<210> SEQ ID NO 265
<211> LENGTH: 25
<212> TYPE: DNA
<213> ORGANISM: Artificial
<220> FEATURE:
<223> OTHER INFORMATION: allele probe

<400> SEQUENCE: 265
cgcgccgagg tgactgaggc cttcc                                       25

<210> SEQ ID NO 266
<211> LENGTH: 28
<212> TYPE: DNA
<213> ORGANISM: Artificial
<220> FEATURE:
<223> OTHER INFORMATION: allele probe

<400> SEQUENCE: 266
atgacgtggc agactgaggc cttcctgg                                    28

<210> SEQ ID NO 267
<211> LENGTH: 16
<212> TYPE: DNA
<213> ORGANISM: Artificial
<220> FEATURE:
<223> OTHER INFORMATION: Invader probe

<400> SEQUENCE: 267
acgccccttt cgccct                                                 16

<210> SEQ ID NO 268
<211> LENGTH: 25
<212> TYPE: DNA
<213> ORGANISM: Artificial
<220> FEATURE:
<223> OTHER INFORMATION: allele probe

<400> SEQUENCE: 268
cgcgccgagg ctttcgcccc tttcg                                       25

```
<210> SEQ ID NO 269
<211> LENGTH: 30
<212> TYPE: DNA
<213> ORGANISM: Artificial
<220> FEATURE:
<223> OTHER INFORMATION: allele probe

<400> SEQUENCE: 269
atgacgtggc agaccaacgg tctcttggac                                    30

<210> SEQ ID NO 270
<211> LENGTH: 24
<212> TYPE: DNA
<213> ORGANISM: Artificial
<220> FEATURE:
<223> OTHER INFORMATION: Invader probe

<400> SEQUENCE: 270
aaacagtgca ggggccgagg gagt                                          24

<210> SEQ ID NO 271
<211> LENGTH: 26
<212> TYPE: DNA
<213> ORGANISM: Artificial
<220> FEATURE:
<223> OTHER INFORMATION: allele probe

<400> SEQUENCE: 271
cgcgccgagg aaagggtaca ggcggg                                        26

<210> SEQ ID NO 272
<211> LENGTH: 29
<212> TYPE: DNA
<213> ORGANISM: Artificial
<220> FEATURE:
<223> OTHER INFORMATION: allele probe

<400> SEQUENCE: 272
atgacgtggc agacgaaggg tacaggcgg                                     29

<210> SEQ ID NO 273
<211> LENGTH: 19
<212> TYPE: DNA
<213> ORGANISM: Artificial
<220> FEATURE:
<223> OTHER INFORMATION: Invader probe

<400> SEQUENCE: 273
gatgtcccca aagcgctgt                                                19

<210> SEQ ID NO 274
<211> LENGTH: 28
<212> TYPE: DNA
<213> ORGANISM: Artificial
<220> FEATURE:
<223> OTHER INFORMATION: allele probe

<400> SEQUENCE: 274
cgcgccgagg cacacctcat gaatcacg                                      28

<210> SEQ ID NO 275
<211> LENGTH: 31
<212> TYPE: DNA
<213> ORGANISM: Artificial
<220> FEATURE:
<223> OTHER INFORMATION: allele probe
```

```
<400> SEQUENCE: 275
atgacgtggc agaccacctc atgaatcacg g                              31

<210> SEQ ID NO 276
<211> LENGTH: 21
<212> TYPE: DNA
<213> ORGANISM: Artificial
<220> FEATURE:
<223> OTHER INFORMATION: Invader probe

<400> SEQUENCE: 276
ctgtttccca gatgggctca t                                         21

<210> SEQ ID NO 277
<211> LENGTH: 23
<212> TYPE: DNA
<213> ORGANISM: Artificial
<220> FEATURE:
<223> OTHER INFORMATION: allele probe

<400> SEQUENCE: 277
cgcgccgagg cgctgcacat ccg                                       23

<210> SEQ ID NO 278
<211> LENGTH: 27
<212> TYPE: DNA
<213> ORGANISM: Artificial
<220> FEATURE:
<223> OTHER INFORMATION: allele probe

<400> SEQUENCE: 278
atgacgtggc agacggctgc acatccg                                   27

<210> SEQ ID NO 279
<211> LENGTH: 19
<212> TYPE: DNA
<213> ORGANISM: Artificial
<220> FEATURE:
<223> OTHER INFORMATION: Invader probe

<400> SEQUENCE: 279
gtgatagggc aggtgcgga                                            19

<210> SEQ ID NO 280
<211> LENGTH: 25
<212> TYPE: DNA
<213> ORGANISM: Artificial
<220> FEATURE:
<223> OTHER INFORMATION: allele probe

<400> SEQUENCE: 280
cgcgccgagg cgaccagaga tgggt                                     25

<210> SEQ ID NO 281
<211> LENGTH: 29
<212> TYPE: DNA
<213> ORGANISM: Artificial
<220> FEATURE:
<223> OTHER INFORMATION: allele probe

<400> SEQUENCE: 281
atgacgtggc agactgacca gagatgggt                                 29

<210> SEQ ID NO 282
<211> LENGTH: 19
```

```
<212> TYPE: DNA
<213> ORGANISM: Artificial
<220> FEATURE:
<223> OTHER INFORMATION: Invader probe

<400> SEQUENCE: 282
ccaagtrcca gcctccaca                                                    19

<210> SEQ ID NO 283
<211> LENGTH: 25
<212> TYPE: DNA
<213> ORGANISM: Artificial
<220> FEATURE:
<223> OTHER INFORMATION: allele probe

<400> SEQUENCE: 283
cgcgccgagg tctctctcct tgccc                                             25

<210> SEQ ID NO 284
<211> LENGTH: 29
<212> TYPE: DNA
<213> ORGANISM: Artificial
<220> FEATURE:
<223> OTHER INFORMATION: allele probe

<400> SEQUENCE: 284
atgacgtggc agaccctctc tccttgccc                                         29

<210> SEQ ID NO 285
<211> LENGTH: 18
<212> TYPE: DNA
<213> ORGANISM: Artificial
<220> FEATURE:
<223> OTHER INFORMATION: forward primer

<400> SEQUENCE: 285
caggagccca atgggtga                                                     18

<210> SEQ ID NO 286
<211> LENGTH: 20
<212> TYPE: DNA
<213> ORGANISM: Artificial
<220> FEATURE:
<223> OTHER INFORMATION: reverse primer

<400> SEQUENCE: 286
acttcgacac cggattccag                                                   20

<210> SEQ ID NO 287
<211> LENGTH: 12
<212> TYPE: DNA
<213> ORGANISM: Artificial
<220> FEATURE:
<223> OTHER INFORMATION: TaqMan probe

<400> SEQUENCE: 287
tggcgcattt cc                                                           12

<210> SEQ ID NO 288
<211> LENGTH: 14
<212> TYPE: DNA
<213> ORGANISM: Artificial
<220> FEATURE:
<223> OTHER INFORMATION: TaqMan probe

<400> SEQUENCE: 288
```

```
cccccgcctg tacc                                                    14
```

<210> SEQ ID NO 289
<211> LENGTH: 21
<212> TYPE: DNA
<213> ORGANISM: Artificial
<220> FEATURE:
<223> OTHER INFORMATION: forward primer

<400> SEQUENCE: 289

```
ggtgtcccag caaagttcat g                                            21
```

<210> SEQ ID NO 290
<211> LENGTH: 19
<212> TYPE: DNA
<213> ORGANISM: Artificial
<220> FEATURE:
<223> OTHER INFORMATION: reverse primer

<400> SEQUENCE: 290

```
tgagcccatc tgggaaaca                                               19
```

<210> SEQ ID NO 291
<211> LENGTH: 17
<212> TYPE: DNA
<213> ORGANISM: Artificial
<220> FEATURE:
<223> OTHER INFORMATION: TaqMan probe

<400> SEQUENCE: 291

```
cccctatgag ctttgtg                                                 17
```

<210> SEQ ID NO 292
<211> LENGTH: 16
<212> TYPE: DNA
<213> ORGANISM: Artificial
<220> FEATURE:
<223> OTHER INFORMATION: forward primer

<400> SEQUENCE: 292

```
ggcccagcca ccatgg                                                  16
```

<210> SEQ ID NO 293
<211> LENGTH: 19
<212> TYPE: DNA
<213> ORGANISM: Artificial
<220> FEATURE:
<223> OTHER INFORMATION: reverse primer

<400> SEQUENCE: 293

```
ctctggctag ggagcaggc                                               19
```

<210> SEQ ID NO 294
<211> LENGTH: 12
<212> TYPE: DNA
<213> ORGANISM: Artificial
<220> FEATURE:
<223> OTHER INFORMATION: TaqMan probe

<400> SEQUENCE: 294

```
ccggcatggc tg                                                      12
```

<210> SEQ ID NO 295
<211> LENGTH: 20
<212> TYPE: DNA
<213> ORGANISM: Artificial

```
<220> FEATURE:
<223> OTHER INFORMATION: forward primer

<400> SEQUENCE: 295
gacaggagtg gtcccatcca                                              20

<210> SEQ ID NO 296
<211> LENGTH: 21
<212> TYPE: DNA
<213> ORGANISM: Artificial
<220> FEATURE:
<223> OTHER INFORMATION: reverse primer

<400> SEQUENCE: 296
tacagacccg gcaccaagta c                                            21

<210> SEQ ID NO 297
<211> LENGTH: 26
<212> TYPE: DNA
<213> ORGANISM: Artificial
<220> FEATURE:
<223> OTHER INFORMATION: reverse primer

<400> SEQUENCE: 297
gccgactgag ccctgggagg taggta                                       26

<210> SEQ ID NO 298
<211> LENGTH: 23
<212> TYPE: DNA
<213> ORGANISM: Artificial
<220> FEATURE:
<223> OTHER INFORMATION: forward primer

<400> SEQUENCE: 298
gccactctcg tgtcgtcagc ttt                                          23

<210> SEQ ID NO 299
<211> LENGTH: 18
<212> TYPE: DNA
<213> ORGANISM: Artificial
<220> FEATURE:
<223> OTHER INFORMATION: reverse primer

<400> SEQUENCE: 299
ggcatgagct aaggcacc                                                18

<210> SEQ ID NO 300
<211> LENGTH: 21
<212> TYPE: DNA
<213> ORGANISM: Artificial
<220> FEATURE:
<223> OTHER INFORMATION: forward primer

<400> SEQUENCE: 300
accgggcacc tgtactcctc a                                            21

<210> SEQ ID NO 301
<211> LENGTH: 22
<212> TYPE: DNA
<213> ORGANISM: Artificial
<220> FEATURE:
<223> OTHER INFORMATION: reverse primer

<400> SEQUENCE: 301
gcatgagcta aggcacccag ac                                           22
```

```
<210> SEQ ID NO 302
<211> LENGTH: 19
<212> TYPE: DNA
<213> ORGANISM: Artificial
<220> FEATURE:
<223> OTHER INFORMATION: forward primer

<400> SEQUENCE: 302
aaggagtgtc agggccgga                                                      19

<210> SEQ ID NO 303
<211> LENGTH: 21
<212> TYPE: DNA
<213> ORGANISM: Artificial
<220> FEATURE:
<223> OTHER INFORMATION: reverse primer

<400> SEQUENCE: 303
agctcggact acggtcatca c                                                   21

<210> SEQ ID NO 304
<211> LENGTH: 19
<212> TYPE: DNA
<213> ORGANISM: Artificial
<220> FEATURE:
<223> OTHER INFORMATION: forward primer

<400> SEQUENCE: 304
tgattcatga ggtgcagcg                                                      19

<210> SEQ ID NO 305
<211> LENGTH: 20
<212> TYPE: DNA
<213> ORGANISM: Artificial
<220> FEATURE:
<223> OTHER INFORMATION: reverse primer

<400> SEQUENCE: 305
cacgtgcagg gcacctagat                                                     20

<210> SEQ ID NO 306
<211> LENGTH: 22
<212> TYPE: DNA
<213> ORGANISM: Artificial
<220> FEATURE:
<223> OTHER INFORMATION: forward primer

<400> SEQUENCE: 306
gcactctcgt gtcgtcagct tt                                                  22

<210> SEQ ID NO 307
<211> LENGTH: 18
<212> TYPE: DNA
<213> ORGANISM: Artificial
<220> FEATURE:
<223> OTHER INFORMATION: reverse primer

<400> SEQUENCE: 307
ggcatgagct aaggcacc                                                       18
```

METHOD OF DETECTING GENETIC POLYMORPHISM

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 54,734 bytes ASCII (Text) file named "702743SequenceListing.txt," created Mar. 27, 2008.

TECHNICAL FIELD

The present invention relates to a method of detecting genetic polymorphism based on the invader assay, particularly to a method suitable for the detection of copy number variation (CNV).

BACKGROUND ART

A genomic region where the copy number of a gene per cell differs among individuals in a certain population is referred to as copy number variation (CNV). Other known forms of polymorphism in genomic DNA number include, for example, single nucleotide polymorphism (SNP), variable number of tandem repeat (VNTR) and microsatellite polymorphism. These forms of polymorphism all involve regions of 1 kbp or shorter (each repeat unit is usually about several to several tens of bases for VNTR, and about two to four bases for microsatellite polymorphism), whereas copy number variation involves longer regions not less than 1 kb and is known to lead to a change in the copy number of the whole gene. As with SNP and the like, a type of copy number variation that occurs at frequencies of 1% or more in a population is also especially referred to as copy number polymorphism (CNP) (hereinafter, the abbreviation "CNV" is used to refer to copy number variation of any frequency).

Copy number variation occurs as relatively increased or decreased copy numbers compared with controls, known as multiplication and deletion, respectively. Usually, in human and other cells, there are two copies of each gene, one being of paternal origin, and the other being of maternal origin. In some individuals, however, there is only one copy of a particular gene per cell (deletion), or there are three copies or more (multiplication). It was in 2004 when the first definite report was presented that such gene multiplication/deletion was observed as polymorphism at high frequency in the genome of humans with normal traits (Nat. Genet., 36:949-51 (2004) and Science, 305: 525-8 (2004)). Later analysis revealed that copy number variation is a relatively common form of polymorphism, accounting for about 12% of the regions of the human genome (Nature, 444: 444-54 (2006)); it was suggested that copy number variation may be widely involved in human trait variations, including disease susceptibility and drug responsiveness.

Because copy number differences in a gene influence gene product levels, some copy number variations can be associated with susceptibility to certain diseases, drug responsiveness, and adverse reactions of drugs. Additionally, a gene may contain an allele that retains normal function, an allele that exhibits increased or decreased function, and an allele that has no function; not only variation at the gene level, but also copy number variation in a particular allele can influence phenotypes. For example, multiplication of a functional allele in the CYP2D6 gene has been shown to be correlated with extremely rapid codeine metabolism that causes opioid poisoning (N. Engl. J. Med., 351:2827-31 (2004)). To apply such information as a "point-of-care (POC)" genetic testing system to personalized medicine, it is essential to develop a novel method for determining the copy numbers of genes relevant to disease susceptibility and drug responsiveness, as well as the copy number of each allele (Genome Res., 16: 949-61 (2006)).

To date, over 2000 CNV regions have been identified by a variety of methods, including BAC-array CGH (comparative genomic hybridization) (see, for example, Nature, 444: 444-54 (2006) and Am. J. Hum. Genet., 79:275-90 (2006)), an oligonucleotide array called ROMA (representational oligonucleotide microarray analysis) (Science, 305: 525-8 (2004)), fosmid paired-end sequence mapping (Nat. Genet., 37:727-32 (2005)) and SNP mapping array (Nature, 444: 444-54 (2006)), and are summarized in the Database of Genomic Variants [projects.tcag.ca/variation/]. However, deleted or multiplied genomic regions have not fully been identified due to technical limitations of these platform technologies. For example, BAC-array CGH is incapable of detecting CNV not more than 50 kb in length because of the large probe size used for detection (100 kb or more). Meanwhile, the ROMA method is of low resolution because of the narrow coverage of genome. In fosmid paired-end sequencing, it is difficult to analyze multiple samples because a large amount of sequence per sample is analyzed. Furthermore, the SNP mapping array poses some problems, including low marker density in some parts of genomic regions (Genome Res., 16: 949-61 (2006) and Annu. Rev. Genomics Hum. Genet., 7:407-42 (2006)). In recent years, high-density oligonucleotide tiling array CGH has often been used to accurately define CNV breakpoints (see, for example, Am. J. Hum. Genet., 79:275-90 (2006)). Although this method has an advantage of high resolution, the probe specificity is inadequate, particularly in homologous regions known as CNV hotspots (Am. J. Hum. Genet., 79:275-90 (2006) and Annu. Rev. Genomics Hum. Genet., 7:407-42 (2006)).

Invader assay coupled with multiplex PCR is one of the most accurate methods for SNP genotyping (Nat Biotechnol; 17: 292-296 (1999) and J. Hum. Genet., 46:471-7 (2001)), and was used in International HapMap project (Nature; 437: 1299-1320 (2005)). This assay was originally developed as an endpoint assay, and comprises measuring fluorescence intensity after an invader reaction for 15 to 60 minutes. Although this protocol gives clear and accurate results of genotyping, nothing has been suggested concerning the applicability thereof to the detection of CNV.

Cytochrome P450 2D6 (CYP2D6) is one of the most extensively studied drug metabolizing enzymes and it is involved in the biotransformation of a large number of medications of wide therapeutic use, including blockers, antiarrhythmics, opioids, antidepressant and antipsychotic agents [Pharmacogenomics J 2005; 5: 6-13]. The CYP2D6 gene is extremely polymorphic, and over 60 known allelic variants have been reported, comprising single nucleotide polymorphisms (SNPs), short insertions and deletions (Indels), gene conversions and copy number variations (CNVs), including whole gene deletion, whole gene multiplication of same types of CYP2D6 gene like CYP2D6* 1xN and CYP2D6*2xN (up to thirteen copies per individual), whole gene duplication of different type of CYP2D6 gene like CYP2D6*10-*36 (www.cypalleles.ki.se/). Approximately half of them have been reported its involvement to the enzymatic activity in vivo and/or in vitro and some of them are risk factors for treatment failure or dose-dependent drug toxicity [N Engl J Med 2004; 351: 2827-2831, Clin Chem 2004; 50: 1623-1633, J Clin Oncol 2005; 23: 9312-9318, Pharmacogenomics J 2007; 7: 257-265, Mol Ther 2008; 83: 234-242].

To investigate association between dosage effect of these polymorphisms(alleles) or haplotypes and its enzymatic activity, it has been desired to develop the system to quantify copy number of each polymorphism (allele) by combining notions of CNVs and other polymorphisms [Nucleic Acids Res 2005; 33: e183, Nat Rev Genet 2007; 8: 639-646].

Though multiple methods have been reported for SNPs, Indels, gene conversions and CNVs genotyping in CYP2D6, including long PCR based Restriction Fragment Length Polymorphism (RFLP) [Clin Chem 2000; 46: 1072-1077], Amplichip P450 [Drug Metab Pharmacokinet 2002; 17: 157-160, Ther Drug Monit 2006; 28: 673-677], pyrosequencing [Eur J Clin Pharmacol 2003; 59: 521-526], SNaPshot [Methods Mol Biol 2005; 297: 243-252] and so on, these technologies have been developed for qualitative detection of the polymorphisms, not quantitative.

The method for total gene copy number using real-time quantitative PCR has already been established and widely used [Hum Mutat 2003; 22: 476-85, J Biomed Biotechnol 2005; 005: 48-53]. On the other hand, a few methods for allele ratio, including molecular inversion probe [Nucleic Acids Res 2005; 33: e183], TaqMan SNP genotyping assays [BMC Genomics 2006; 7: 143], melting curve analysis [Clin Chem 2000; 46:1574-1582] and Mass spectrometry [Clin Chem 2005; 51: 2358-2362] have been reported. However, the possibility of application to CYP2D6 genotyping has still been unclear.

SUMMARY OF THE INVENTION

It is an object of the present invention to provide a novel method of accurately, quickly, and conveniently detecting genetic polymorphism, particularly widely applicable to the detection of copy number variation (CNV).

The present inventors modified the invader assay, which had conventionally been performed as an endpoint method, to enable real-time detection of fluorescence during post-PCR enzyme reaction (designated as polymerase chain reaction-real-time invader assay; PCR-RETINA). As a result, the inventors unexpectedly found that genomic multiplication in proportion to allele ratio, i.e., allele asymmetry resulting from multiplication, can be detected in the initial stage of an invader reaction before reaching a plateau. Furthermore, the present inventors succeeded in determining the copy number of each allele by combining this method with total copy numbers calculated by real-time quantitative PCR, and developed the present invention.

Accordingly, the present invention provides:

[1] a method of determining the genotype of a subject in a genomic region comprising an SNP site, comprising a step for performing typing of the SNP site with a DNA-containing sample comprising the genomic region from the subject as the template by an invader assay, wherein fluorescence is measured on a real time basis;

[2] the method according to [1] above, the copy number ratio of both alleles is determined using the ratio of fluorescence intensity corresponding to each allele at a time before saturation of fluorescence intensity;

[3] the method according to [2] above, wherein the genomic region comprising an SNP site is present in a CNV region;

[4] the method according to [2] above, which is for detecting multiplication accompanied by allele asymmetry;

[5] the method according to [1] above, further comprising a step for amplifying the genomic region comprising an SNP site prior to the invader step;

[6] the method according to [5] above, wherein the genomic region comprises a plurality of SNP sites, and wherein a plurality of regions comprising the plurality of SNP sites are simultaneously amplified in the step of amplification;

[7] the method according to [5] above, wherein the copy number of each allele is determined based on the total copy number of both alleles (total gene copy number) determined using quantitative PCR;

[8] the method according to [6] above, wherein the quantitative PCR is performed by the TaqMan method; and

[9] the method according to [6] above, comprising defining CNV breakpoints by identifying a range in which a plurality of SNP sites, whether continuous or not, with detected multiplication or deletion accompanied by allele asymmetry, and the like.

EFFECT OF THE INVENTION

The present invention is highly advantageous in the detection of CNV regions and genomic amplification regions in cancer and the like, and the refinement of breakpoints in CNV regions and genomic amplification regions. Accordingly, the method of the present invention is a potential tool applicable to POC genetic diagnosis and accelerating the realization of personalized medicine.

BRIEF DESCRIPTION OF THE DRAWINGS

FIGS. 6-1 through 6-3 show evaluations by multiplex PCR-RETINA (mPCR-RETINA). The performance of each assay was compared between PCR-RETINA (single PCR) and mPCR-RETINA. The alphanumeric characters in boxes indicate rs numbers in SNP assays. The upper AD plots show the results of PCR-RETINA (single PCR); the lower AD plots show the results of mPCR-RETINA. Each red circle represents an individual with allele asymmetry. Red arrows indicate the boundaries of CNV regions.

BEST MODE FOR CARRYING OUT THE INVENTION

The present invention provides a method of determining the genotype of a subject in a genomic region comprising an SNP site by real-time invader assay (RETINA) (hereinafter, also referred to as "the genotyping method of the present invention"). The subject in the genotyping method of the present invention is not particularly limited, as long as it has a genomic DNA comprising an SNP site, and the subject is preferably a mammal, particularly a human, a mouse or the like, for which mammals data on SNP have been accumulated. The genomic region comprising an SNP site to be subjected to typing, is also not particularly limited. In the case of humans, for example, such genomic regions include genomic regions comprising any SNP site registered with the NCBI SNP database [www.ncbi.nlm.nih.gov/SNP/] and JSNP database [snp.ims.u-tokyo.acjp/index.html].

Figures 1, 6:
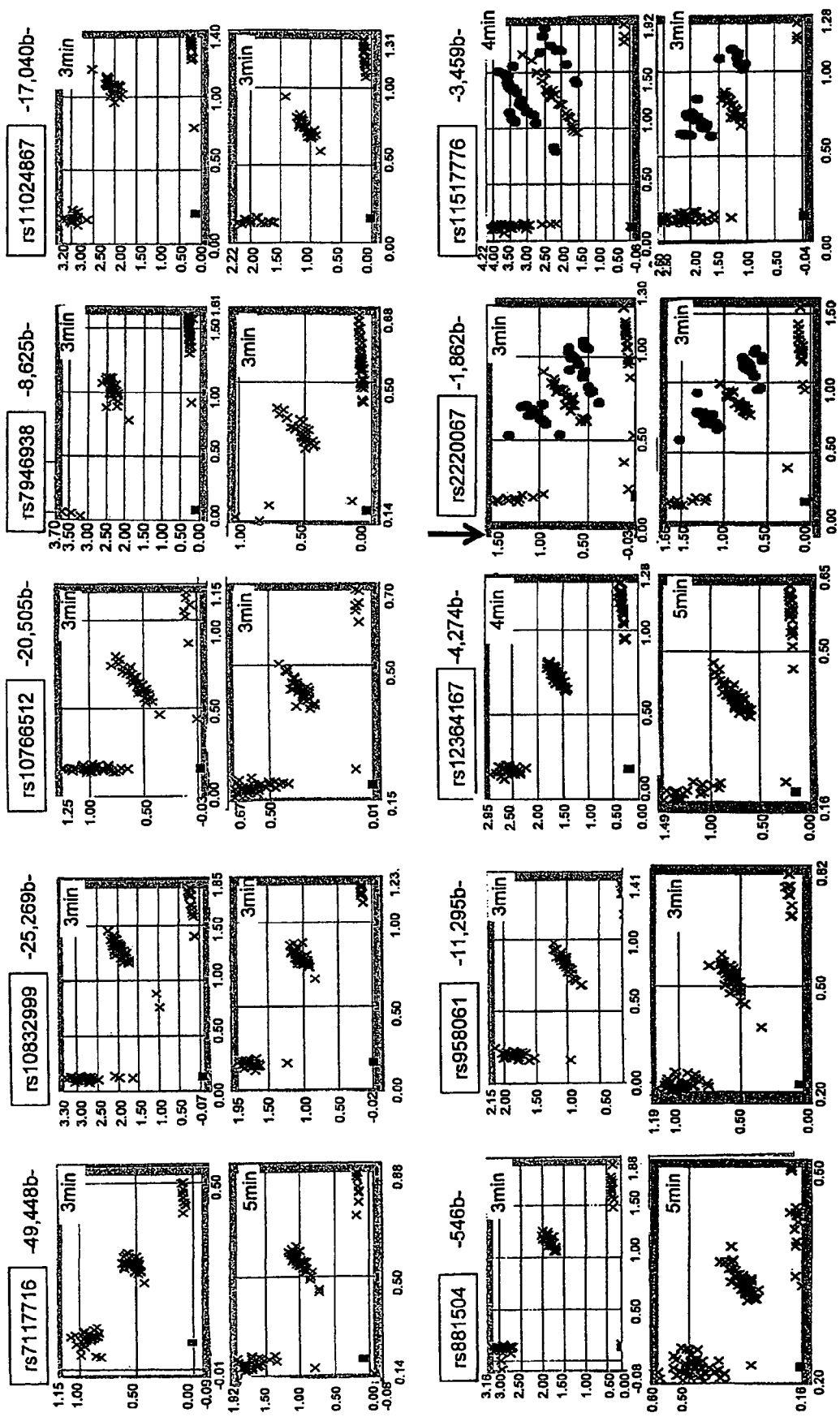
Figures 2, 6:
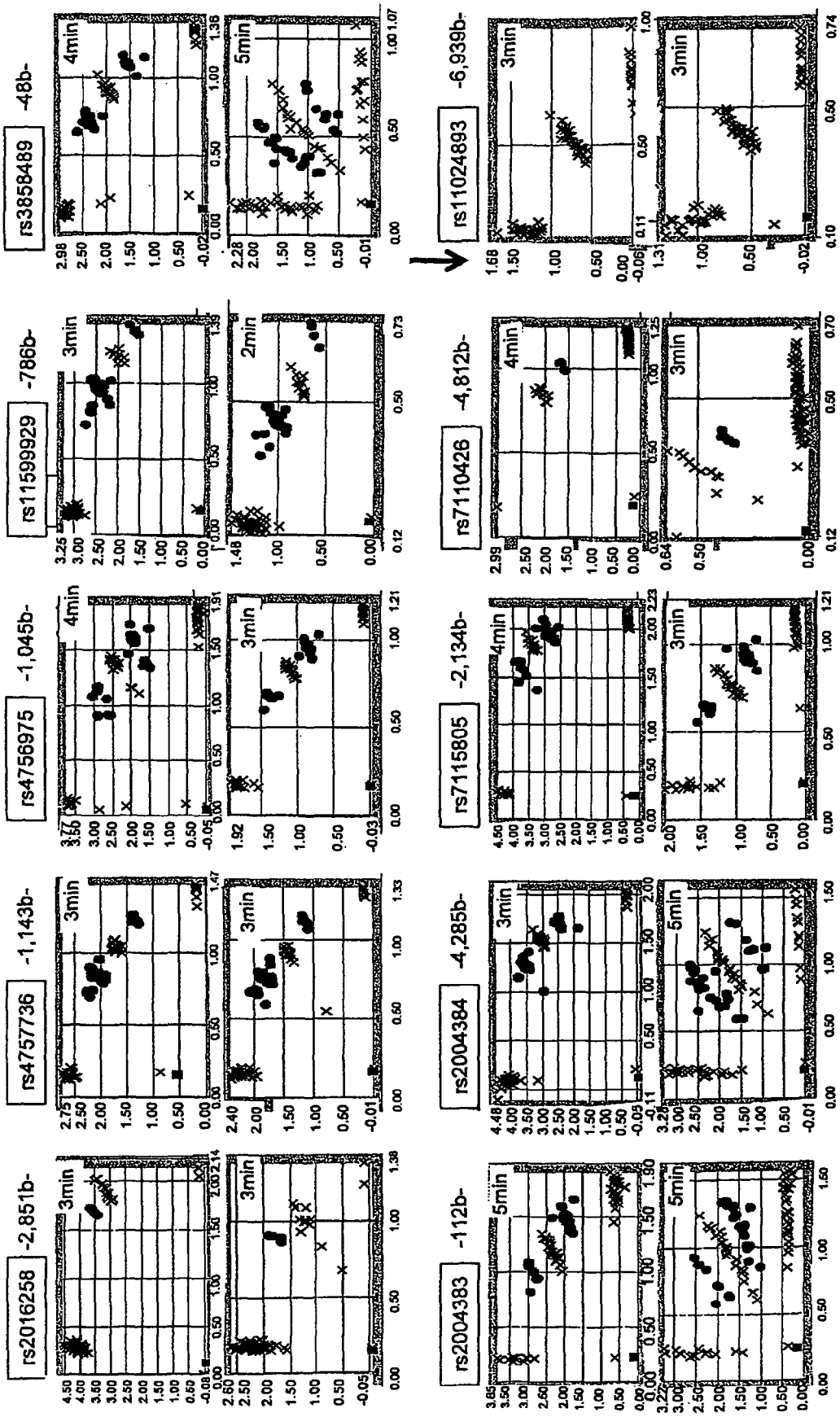
Figures 3, 6:
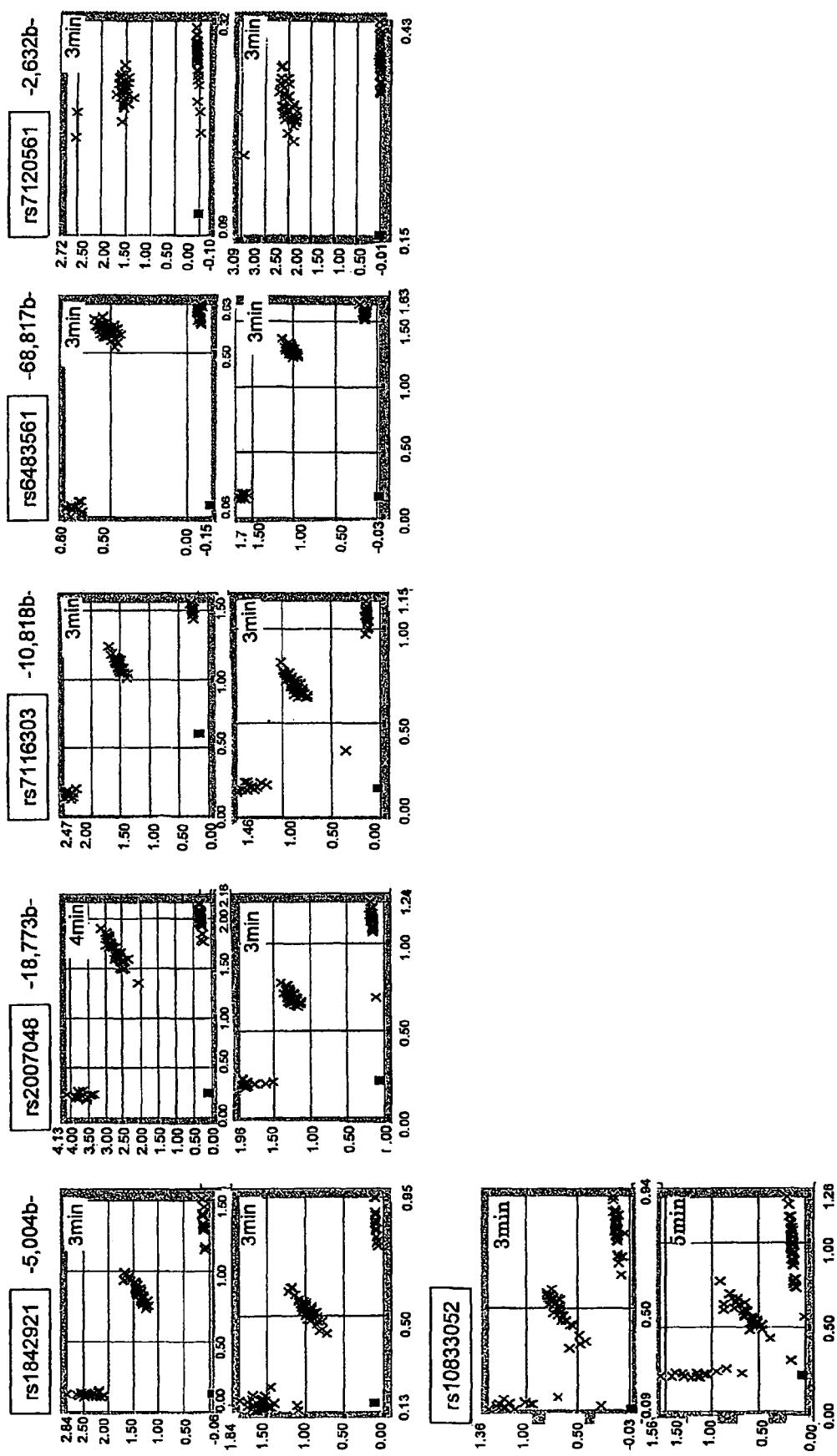

Preferably, the genomic region comprising an SNP site in the present invention exists within a copy number variation (CNV) region. To date, CNV regions in the human genome have been identified by a variety of methods, and are summarized in the Database of Genomic Variants [projects.tcag.ca/variation/]. For example, the CNV region comprising the MRGPRX1 gene, used in Example 1 below, is registered as Locus 2220 with the Database of Genomic Variants, which region spans an about 290 kbp of the base number 18,762,138-19,051,811 of chromosome 11, in which the 26 known SNP sites specified by RefSNP ID in FIG. 6 are contained.

Examples of polymorphism include SNP as well as Indel and gene conversion polymorphism. Indel is an abbreviation of Insertion/Deletion. The gene conversion polymorphism is a polymorphism in which a DNA sequence has been converted into another DNA sequence. Herein, the descriptions concerning SNPs may be interpreted as ones concerning Indel or gene conversion polymorphism, as necessary.

The genomic region comprising an SNP site may comprise one SNP site, and may comprise two or more SNP sites. If the genomic region comprises a plurality of SNP sites, it is possible to collect a genomic DNA-containing sample for each SNP site from a subject to perform the invader assay. However, since it is desirable that typing of a plurality of SNP sites be performed from a small amount of genomic DNA, it is preferable that a plurality of subregions comprising the individual SNP sites in the genomic region be simultaneously amplified from one genomic DNA-containing sample by PCR (multiplex PCR or mPCR), and that an invader reaction be performed for each SNP site with this amplification product as the template.

The subject-derived DNA-containing sample comprising the genomic region may be a genomic DNA itself, and may be an amplification product obtained by previously amplifying a genomic region comprising a desired SNP site by PCR with the genomic DNA as the template. The sample collected from the subject to acquire genomic DNA is not particularly limited, as long as genomic DNA is contained, and may comprise any kind of cell or tissue. Because the sample is desirably collected by minimally invasive means to the subject, for example, blood, blood cell components, lymph fluid, semen, hair and the like are preferable, with greater preference given to blood and blood cell components being fractions thereof (e.g., leukocytes). Extraction of genomic DNA from the collected sample can be achieved by any method known per se; those skilled in the art can choose and use a suitable method according to the kind of sample collected and the like, as necessary.

In a preferred embodiment, the subject-derived DNA-containing sample comprising a desired genomic region is an amplification product obtained by previously amplifying a genomic region comprising a desired SNP site by PCR. Accordingly, the genotyping method of the present invention preferably further comprises a step for amplifying a genomic region comprising an SNP site prior to the invader step. In this step of amplification, PCR may be performed by a conventional method using a genomic DNA prepared as the template DNA and a primer pair for amplifying the base sequence comprising an SNP site to be subjected to typing. As described above, if the genomic region comprises a plurality of SNP sites, it is preferable that multiplex PCR (mPCR) which amplifies all SNP sites within the genomic region from one genomic DNA sample by one round of PCR using a plurality of primer pairs for amplifying a base sequence comprising each SNP site. For example, 50 or more (e.g., 100 or more, 300 or more) regions each comprising SNP site can be simultaneously amplified by mPCR. For details of mPCR, see, for example, JP-A-2002-300894.

Each primer pair used in the above-described step of amplification is designed to amplify a DNA fragment comprising each SNP site, for example, DNA fragment of about 100 bp to several kbp long, preferably about 100 to about 300 bp long. These primers are not particularly limited, as long as the desired fragment can be specifically amplified; for example, the primers are about 15 to about 30 bases long, preferably about 17 to about 25 bases long, and more preferably about 18 to about 22 bases long. In performing mPCR, the primer pair used is preferably designed in order that each primer of the pair anneals to the template DNA at almost the same temperature.

In the above-described step of amplification, it is preferable to apply so-called hot start method, wherein an elongation reaction with DNA polymerase is initiated after the reaction solution becomes hot, so as to prevent the mis-annealing and oligomerization of the primers. For details of the hot start method, see, for example, JP-A-2002-300894.

The genotyping method of the present invention comprises performing typing of SNP sites in a desired genomic region by real-time invader assay (RETINA) with a subject-derived DNA-containing sample comprising the genomic region, prepared as described above, as the template. RETINA means an assay technique for measuring fluorescence intensity from the start of the reaction on a real time basis in the invader assay originally performed as an endpoint assay. This real-time measurement of fluorescence can conveniently be achieved using various conventionally known apparatuses for real-time quantitative PCR.

The principle and embodiments of the invader assay (see, for example, JP-A-2002-300894) are summarized as follows:

In the invader assay, unlike the TaqMan PCR method and the like, the allele-specific oligonucleotide (allele probe) itself is not labeled, and has a sequence (flap) not complementary to the template DNA on the 5' side of the base at the polymorphism site, and a complementary sequence specific for the template on the 3' side of the base at the polymorphism site. Further used in the invader assay are an oligonucleotide having a complementary sequence specific for the 3' side of the polymorphism site of the template (invader probe; the base corresponding to the polymorphism site at the 5' end of the probe is any base), and an FRET (fluorescence resonance energy transfer) probe which has a sequence capable of taking a hairpin structure on the 5' side thereof and a sequence (this sequence is complementary to the flap of the allele probe) continuous to the 3' side from the bases that forms pairs with the 5'-end bases upon formation of the hairpin structure. The FRET probe is labeled with a fluorescent substance (for example, FAM, VIC) at the 5' end thereof and coupled with a quencher (for example, TAMRA). Because the quencher exists in the vicinity of the fluorescent substance when the probe takes the hairpin structure, no fluorescence is detected if the probe is remained as is (in hairpin structure).

When the template genomic DNA is reacted with an allele probe and invader probe, the 3' end of the invader probe invades at the polymorphism site upon complementary binding of these three components. When the single-stranded portion of the allele probe (i.e., flap portion on the 5' side from the base at the polymorphism site) is cut out with an enzyme cleavase that recognizes thus formed structure at the polymorphism site, the released flap binds complementarily to the FRET probe, and in turn, the polymorphic site of the flap invades into the hairpin structure of the FRET probe. As thus formed structure is recognized and cleaved by cleavase, the fluorescent end-labeling of the FRET probe is released and no longer is influenced by the quencher; thus, fluorescence is detected.

In the conventional invader assay as an endpoint assay, fluorescence intensity is measured after performing an invader reaction for about 15 to 60 minutes, whereas in the genotyping method of the present invention, an increase in fluorescence intensity is measured on a real time basis, and the copy number ratio of both alleles is determined using the ratio of fluorescence intensities corresponding to the respective alleles having a desired SNP site at a time before saturation of fluorescence intensity, i.e., before the invader reaction reaches a plateau. Although there is some variation depending on the kind of DNA used as the template, reaction conditions and the like, the invader reaction usually reaches a plateau in about 15 to 20 minutes (see FIG. 1a); in the genotyping method of the present invention, the fluorescence intensity ratio obtained up to 15 minutes after the start of the reaction, preferably at about 1 to about 10 minutes after the start of the reaction, is used. Hence, the genotyping method of the present invention allows quicker typing of a desired SNP site than the conventional invader assay as the endpoint method.

The present method exhibits the best resolution at a time just before the reaction reaches a plateau (see FIGS. 1c and d). Accordingly, in a preferred embodiment, for a period from the start of the reaction to the complete reach of the reaction to a plateau, at intervals of, for example, about 15 seconds to about 1 minute, preferably about 30 seconds, fluorescence intensity is measured and recorded, and the ratio of fluorescence intensities corresponding to respective alleles is determined using fluorescence intensity at a time just before saturation of the fluorescence intensity. The ratio of fluorescence intensities may be determined by actually calculating the ratio of the two, or by generating a graph with one fluorescence intensity plotted on the ordinate and the other fluorescence intensity plotted on the abscissa. In the former case, close values are obtained from subjects having the same copy number ratio of both alleles, and distinctly different values are obtained from subjects with different copy number ratios. In the latter case, plots from subjects having the same copy number ratio of both alleles gather in a certain region on the graph (clustering), whereas plots from subjects with different copy number ratios appear at distinct positions on the graph. Therefore, the genotyping method of the present invention is useful not only in the simple typing of SNP sites, but also particularly in the detection of copy number variation.

Comparing with standard samples with known allele ratios, it is possible not only to determine the difference in copy number ratio, but also to quantify the copy number ratio. Specifically, an oligonucleotide comprising the same base sequence as a region comprising a desired SNP site is synthesized for each allele; these oligonucleotides are mixed in various allele ratios (for example, 1:0, 8:1 to 1:8, 0:1 and the like) to prepare a plurality of standard template samples; RETINA is performed in the same way to determine fluorescence intensity ratios at the same time point as the subject; and a standard curve for the relationship between fluorescence intensity ratio and allele ratio is generated (see FIG. 4b), or a graph is generated with one fluorescence intensity plotted on the ordinate and the other fluorescence intensity plotted on the abscissa (see FIG. 4a). By applying the fluorescence intensity ratio in the subject, determined as described above, to the standard curve to obtain the corresponding allele ratio, or by comparing the positions of the plots on the graph with those of the standard template samples (see FIG. 4d), the copy number ratio of both alleles for the region comprising a desired SNP site in the subject can be determined.

The genotyping method of the present invention may be performed on a large number of subjects. In a population of subjects without gene multiplication or CNV, fluorescence intensity ratios corresponding to each allele at a time before the invader reaction reaches a plateau are obtained as numerical values corresponding to any one of the three groups of homozygotes (allele ratio is 1:0 or 0:1) and heterozygotes (allele ratio is 1:1) for each allele (three clusters plotted on a graph). In a population of subjects with gene multiplication, particularly those with allele asymmetry resulting from multiplication, fluorescence intensity ratios are different from any of the above-described three groups, and plotted at positions other than any of the three clusters (see FIGS. 2a and b and FIGS. 3a and b). As mentioned herein, "allele asymmetry" means a heterozygote wherein the copy number ratio of both alleles is not 1:1 (for example, 2:1, 1:2). Meanwhile, allele symmetry means a heterozygote wherein the copy number ratio of both alleles is 1:1 and a homozygote.

Therefore, in such cases, even if standard curve analysis is not performed, the three clusters in which plots from a large number of subjects gather can be estimated to be homozygotes or heterozygotes wherein the total copy number is 2 copies, and subjects plotted outside these clusters can be judged to have multiplication accompanied by allele asymmetry in a region comprising a desired SNP site.

While being advantageous in that gene multiplication accompanied by allele asymmetry can be detected quickly and conveniently, the genotyping method of the present invention is only capable of determining the copy number ratio of both alleles; therefore, the method fails to distinguish between allele-symmetric gene multiplication (for example, 2 copies:2 copies) and heterozygotes without gene multiplication (1 copy:1 copy), to distinguish between homozygotes with gene multiplication (3 copies:0 copies) and homozygotes without gene multiplication, and to distinguish between homozygotes and deletion (1 copy:0 copies). Hence, the total copy number of both alleles is determined by performing quantitative PCR with a subject-derived DNA-containing sample comprising a desired genomic region as the template, and combined with the copy number ratio of both alleles obtained by RETINA to determine the copy number of each allele. Accordingly, the present invention also provides a method of genotyping a subject by determining the copy number of each allele using RETINA and quantitative PCR in combination.

For example, if the total copy number of both alleles obtained by quantitative PCR is 4 copies, and the copy number ratio of both alleles obtained by RETINA is 1:1, it can be judged that each allele is present in 2 copies. If the total copy number of both alleles obtained by quantitative PCR is 3 copies, and the copy number ratio of both alleles obtained by RETINA is 1:0, the subject can be judged to be a homozygote with duplication. If the total copy number of both alleles obtained by quantitative PCR is 1 copy, and the copy number ratio of both alleles obtained by RETINA is 1:0, the subject can be judged to have deletion.

If there is a disagreement between the results of RETINA and quantitative PCR, the genomic DNA sequence of the subject region can be confirmed by direct sequencing. As described in Example 1 below, in the case of a subject with polymorphism in the primer sequence portion used in quantitative PCR, quantitative values lower than the actual copy number are sometimes obtained due to low primer annealing efficiency. It will be understood that the genotyping method of the present invention, which employs RETINA, provides limited but extremely highly reliable information when applied alone.

As used here, quantitative PCR can be performed using any techniques known as real-time PCR per se. These techniques involve the detection of the amount of DNA amplified using a fluorescent reagent on a real-time basis, and require an apparatus comprising both thermal cycler and spectral fluorophotometer. Such apparatuses are commercially available. Some methods using different fluorescent reagents are available, including, for example, the intercalater method, Taq-Man™ probe method, and Molecular Beacon method. All these methods involve the addition of a fluorescent reagent or fluorescent probe, referred as an intercalater, TaqMan™ probe or Molecular Beacon probe, to a PCR reaction system comprising a template genomic DNA and a primer pair for amplifying a genomic region comprising a desired SNP site. Because an intercalater binds to a synthesized double-stranded DNA and produces fluorescence upon exposure to excitation light, the amount of amplification product can be monitored by measuring fluorescence intensity, whereby the original amount of template DNA can be estimated. The TaqMan™ probe is an oligonucleotide modified with a fluorescent substance and a quenching substance at the respective ends thereof, capable of hybridizing with amplification regions of target nucleic acid, which probe hybridizes with the target nucleic acid but does not emit fluorescence due to the presence of the quenching substance during annealing, and which emits fluorescence as the fluorescent substance is released upon degradation by the exonuclease activity of DNA polymerase during the elongation reaction. Therefore, by measuring fluorescence intensity, the amount of amplification product can be monitored, whereby the original amount of template DNA can be estimated. The Molecular Beacon probe is an oligonucleotide modified with a fluorescent substance and a quenching substance at the respective ends thereof, capable of hybridizing with amplification regions of target nucleic acid, and also capable of taking a hairpin secondary structure, which probe does not emit fluorescence due to the presence of the quenching substance when taking the hairpin structure, and which emits fluorescence as the distance between the fluorescent substance and the quenching substance expands upon hybridization with the target nucleic acid during annealing. Therefore, by measuring fluorescence intensity, the amount of amplification product can be monitored, whereby the original amount of template DNA can be estimated. In the present invention, the TaqMan method is preferably used.

As described above, the genotyping method of the present invention makes it possible to detect multiplication accompanied by allele asymmetry in a region comprising each SNP site by amplifying a partial base sequence comprising each SNP site for a genomic region comprising a plurality of SNP sites, by mPCR, and thereafter performing RETINA for each SNP site with the obtained amplification product as the template. Therefore, for example, by performing mPCR- RETINA for each SNP site contained in a long CNV region as long as several hundred kbp, it is possible to determine a region, where copy number variation can be detected, between an SNP and another SNP in the CNV region, and then identify the SNPs between which CNV has occurred, i.e., to define the CNV breakpoint, on the basis of the information obtained. Defining the CNV breakpoint is essential for determining whether the entire functional unit of a particular gene or a part thereof has been multiplied. When gene multiplication in the functional unit is revealed, important information for elucidating the correlation between the gene multiplication and disease susceptibility or drug responsiveness can be provided. For example, in Example 1 below, by performing mPCR-RETINA on the CNV region comprising the MRGPRX1 gene, registered as Locus 2220 with the Database of Genomic Variants, it can be judged that the boundaries of the multiplied region are determined between rs12364167 and rs2220067 on one side, and between rs7110426 and rs11024893 on the other side (see FIG. 6), and that the MRGPRX1 gene being present in the region sandwiched by these boundaries has been multiplied as a functional unit.

As used herein, "multiplication" means that plural copies of a specific gene are present per cell. The gene exists in plural copies in tandem on one chromosome, or collectively exists in plural copies on two homologous chromosomes and the like. Herein, "multiplication" embraces the presence of 2 copies (duplication), 3 copies (triplication), or more copies of one gene per cell.

EXAMPLES

The present invention is hereinafter described in more detail by means of the following examples, which, however, are for illustrative purposes only and never limit the scope of the invention.

Example 1

Materials And methods

Genomic DNA

A total of 180 genomic DNA samples consisting of 30 trios of CEPH families with European ancestry (CEU) and 30 trios of Yoruba (YRI) for the International HapMap project [International HapMap Consortium, 2005] were used. These DNA samples were purchased from the Coriell Cell Repository.

PCR-RETINA

A PCR primer, invader probe and allele probe reported for CYP2D6 assay were used [Nevilie et al., Biotechniques, 32: S34-43, 2002]. The remaining PCR primers were designed using Primer Express 1.5 (Applied Biosystems), and other invader probes and allele probes were designed and synthesized on the basis of reported standards [Mast and Arruda, Methods Mol Biol. 335: 173-186, 2006]. The sequences of all probes and primers are listed in Table 1. FRET probes labeled with FAM or Yakima Yellow were purchased from Third Wave Technologies. The Rox dye (Sigma) was used to normalize reporter signals.

In all assays, PCR amplification was performed at a primer concentration of 100 nM according to the manufacturer's protocol with purified genomic DNA as the template. In all the PCR amplification, Takara Ex Taq HS (Takara) was used. A PCR reaction using one set of primers was performed with a reaction volume of 5 μl using GeneAamp 9700 (Applied Biosystems). For CYP2D6 assay conditions, denaturation of genomic DNA at 95° C. for 2 minutes was followed by a PCR reaction of 35 cycles at 95° C. for 15 seconds and at 68° C. for 4 minutes. In MRGPRX1 assay, a denaturation at 95° C. for 2 minutes was followed by a PCR reaction of 35 cycles at 95° C. for 15 seconds, at 58° C. for 30 seconds and at 72° C. for 1 minute. Regarding multiplex PCR reaction conditions, with a reaction volume of 10 μl, a denaturation at 95° C. for 2 minutes was followed by a PCR reaction of 37 cycles at 95° C. for 15 seconds, at 58° C. for 30 seconds and at 72° C. for 4 minutes [Ohnishi et al., J Hum Genet. 46: 471-477 2001].

After PCR reaction, the product was diluted 10-fold and used as the template for RETINA. RETINA was performed with a reaction volume of 4 μl according to the protocol recommended by Third Wave Technologies using ABIprism 7900 (Applied Biosystems). Data analysis was performed using the Excel program (Microsoft).

Copy Number Analysis By Taqman Assays

Copy number analysis was performed using Taqman assays. First, Tagman assay reported for CYP2D6 was used [Bodin et al., J Biomed Biotechnol. 3: 248-53 2005]. However, since 3-base insertion in the reverse primer of the reported assay was found in several YRI individuals, a new reverse primer was designed using Primer Express to obtain accurate data in the analysis of YRI individuals, and copy number analysis was performed again. For MRGPRX1, all assays were designed using Primer Express 1.5. The Taqman probe used had been labeled with FAM at the 5' end thereof, and coupled with No Fluorescence Quencher and MGB at the 3' end thereof. Used as the reference gene was RNase P assay (Applied Biosystems) that had been labeled with VIC. All Taqman assays were performed according to the reported protocol, and copy numbers were calculated by the $\Delta\Delta Ct$ method [Bodin et al., 2005, ibid.]. Assuming a sample with the median $\Delta Ct$ value to have two copies, the present inventors used the sample as the calibrator. All samples were tested in duplicate, and mean copy number values were used in scatter plot analysis. The sequences of the primers and probes used in all assays are listed in Table 1.

DNA Sequencing

Two YRI samples showing a disagreement between the results of PCR-RETINA and Taqman assay were amplified by PCR under reported reaction conditions [Dorad et al., Biotechniques. 39: 571-574 2005]. The amplified DNAs were subjected to DNA sequencing using the ABI prism 3700 sequencer (Applied Biosystems) and analyzed using Polyphred software (University of Washington).

TABLE 1

| Primer/<br>Probe Name | Oligo Type | Assay Type | Purpose | Tagrget |
|---|---|---|---|---|
| rs2114912A | Artificial<br>template | PCR-RETINA | Confirmation of the<br>performance of PCR-RIA | None |
| rs2114912C | Artificial<br>template | PCR-RETINA | Confirmation of the<br>performance of PCR-RIA | None |

TABLE 1-continued

| | | | | |
|---|---|---|---|---|
| rs2114912F | Forward Primer | PCR-RETINA | Confirmation of the performance of PCR-RIA | None |
| rs2114912R | Reverse Primer | PCR-RETINA | Confirmation of the performance of PCR-RIA | None |
| rs2114912 In | Invader Probe | PCR-RETINA | Confirmation of the performance of PCR-RIA | None |
| rs2114912 AL1 | Allele Probe 1 | PCR-RETINA | Confirmation of the performance of PCR-RIA | None |
| rs2114912 AL2 | Allele Probe 2 | PCR-RETINA | Confirmation of the performance of PCR-RIA | None |
| PCR 1F | Forward Primer | PCR-RETINA | Confirmation of gene Duplication | CYP2D6 |
| PCR 1R | Reverse Primer | PCR-RETINA | Confirmation of gene Duplication | CYP2D6 |
| PCR 2F | Forward Primer | PCR-RETINA | Confirmation of gene Duplication | CYP2D6 |
| PCR 2R | Reverse Primer | PCR-RETINA | Confirmation of gene Duplication | CYP2D6 |
| CYP2D6*10-100 C > T In | Invader Probe | PCR-RETINA | Confirmation of gene Duplication | CYP2D6 |
| CYP2DT*10-100 C > T AL1 | Allele Probe 1 | PCR-RETINA | Confirmation of gene Duplication | CYP2D6 |
| CYP2D6*10-100 C > T AL2 | Allele Probe 2 | PCR-RETINA | Confirmation of gene Duplication | CYP2D6 |
| CYP2D6*4-1844 G > A In | Invader Probe | PCR-RETINA | Confirmation of gene Duplication | CYP2D6 |
| CYP2D6*4-1846 G > A AL1 | Allele Probe 1 | PCR-RETINA | Confirmation of gene Duplication | CYP2D6 |
| CYP2D6*4-1846 G > A AL2 | Allele Probe 2 | PCR-RETINA | Confirmation of gene Duplication | CYP2D6 |
| CYP2D6*2-2850 C > T In | Invader Probe | PCR-RETINA | Confirmation of gene Duplication | CYP2D6 |
| CYP2D6*2-2850 C > T AL1 | Allele Probe 1 | PCR-RETINA | Confirmation of gene Duplication | CYP2D6 |
| CYP2D6*2-2850 C > T AL2 | Allele Probe 2 | PCR-RETINA | Confirmation of gene Duplication | CYP2D6 |
| CYP2D6 Reported Copy number F | Forward Primer | TaqMan | Confirmation of gene Duplication | CYP2D6 |
| CYP2D6 Reported Copy number R | Reverse Primer | TaqMan | Confirmation of gene Duplication | CYP2D6 |
| CYP2D6 Reported Copy number T | TaqMan Probe | TaqMan | Confirmation of gene Duplication | CYP2D6 |
| CYP2D6 Designed Copy number R | Reverse Primer | TaqMan | Confirmation of Discordance | CYP2D6 |
| DPKUP | Forward Primer | PCR (Sequence amplicon) | Confirmation of Discordance | CYP2D6 |
| DPKLDW | Reverse Primer | PCR (Sequence amplicon) | Confirmation of Discordance | CYP2D6 |
| 2 D6SeqF | Sequence Primer | Sequence | Confirmation of Discordance | CYP2D6 |
| 2 D6SeqR | Sequence Primer | Sequence | Confirmation of Discordance | CYP2D6 |

TABLE 1-continued

| | | | | |
|---|---|---|---|---|
| rs3858489F | Forward Primer | PCR-RETINA | Confirmation of gene Duplication | MRGPRX1 |
| rs3858489R | Reverse Primer | PCR-RETINA | Confirmation of gene Duplication | MRGPRX1 |
| rs3858489 In | Invader Probe | PCR-RETINA | Confirmation of gene Duplication | MRGPRX1 |
| rs3858489 AL1 | Allele Probe 1 | PCR-RETINA | Confirmation of gene Duplication | MRGPRX1 |
| rs3858489 AL2 | Allele Probe 2 | PCR-RETINA | Confirmation of gene Duplication | MRGPRX1 |
| rs11599929F | Forward Primer | PCR-RETINA | Confirmation of gene Duplication | MRGPRX1 |
| rs11599929R | Reverse Primer | PCR-RETINA | Confirmation of gene Duplication | MRGPRX1 |
| rs11599929 In | Invader Probe | PCR-RETINA | Confirmation of gene Duplication | MRGPRX1 |
| rs11599929 AL1 | Allele Probe 1 | PCR-RETINA | Confirmation of gene Duplication | MRGPRX1 |
| rs11599929 AL2 | Allele Probe 2 | PCR-RETINA | Confirmation of gene Duplication | MRGPRX1 |
| rs4756975F | Forward Primer | PCR-RETINA | Confirmation of gene Duplication | MRGPRX1 |
| rs4756975R | Reverse Primer | PCR-RETINA | Confirmation of gene Duplication | MRGPRX1 |
| rs4756975 In | Invader Probe | PCR-RETINA | Confirmation of gene Duplication | MRGPRX1 |
| rs4756975 AL1 | Allele Probe 1 | PCR-RETINA | Confirmation of gene Duplication | MRGPRX1 |
| rs4756975AL2 | Allele Probe 2 | PCR-RETINA | Confirmation of gene Duplication | MRGPRX1 |
| MRGPRX1 copy number F | Forward Primer | TaqMan | Confirmation of gene Duplication | MRGPRX1 |
| MRGPRX1 copy number R | Reverse Primer | TaqMan | Confirmation of gene Duplication | MRGPRX1 |
| MRGPRX1 copy number T | TaqMan Probe | TaqMan | Confirmation of gene Duplication | MRGPRX1 |
| MRGPR5'2copyFP (CA1) | Forward Primer | TaqMan | Breakpoint Refinement | MRGPRX1 |
| MRGPR5'2copyRP (CA1) | Reverse Primer | TaqMan | Breakpoint Refinement | MRGPRX1 |
| MRGPR5'2copyT (CA1) | TaqMan Probe | TaqMan | Breakpoint Refinement | MRGPRX1 |
| MRGPR5'3copyFP (CA2) | Forward Primer | TaqMan | Breakpoint Refinement | MRGPRX1 |
| MRGPR5'3copyRP (CA2) | Reverse Primer | TaqMan | Breakpoint Refinement | MRGPRX1 |
| MRGPR5'3copyT (CA2) | TaqMan Probe | TaqMan | Breakpoint Refinement | MRGPRX1 |
| MRGPR3'3copyFP (CA3) | Forward Primer | TaqMan | Breakpoint Refinement | MRGPRX1 |
| MRGPR3'3copyRP (CA3) | Reverse Primer | TaqMan | Breakpoint Refinement | MRGPRX1 |

TABLE 1-continued

| | | | | |
|---|---|---|---|---|
| MRGPR3'copyT (CA3) | TaqMan Probe | TaqMan | Breakpoint Refinement | MRGPRX1 |
| MRGPR3'2copyFP (CA4) | Forward Primer | TaqMan | Breakpoint Refinement | MRGPRX1 |
| MRGPR3'2copyRP (CA4) | Reverse Primer | TaqMan | Breakpoint Refinement | MRGPRX1 |
| MRGPR3'2copyT (CA4) | TaqMan Probe | TaqMan | Breakpoint Refinement | MRGPRX1 |
| rs958061F | Forward Primer | PCR-RETINA | Breakpoint Refinement | MRGPRX1 |
| rs958061R | Reverse Primer | PCR-RETINA | Breakpoint Refinement | MRGPRX1 |
| rs958061 In | Invader Probe | PCR-RETINA | Breakpoint Refinement | MRGPRX1 |
| rs958061AL1 | Allele Probe 1 | PCR-RETINA | Breakpoint Refinement | MRGPRX1 |
| rs958061AL2 | Allele Probe 2 | PCR-RETINA | Breakpoint Refinement | MRGPRX1 |
| rs12364167F | Forward Primer | PCR-RETINA | Breakpoint Refinement | MRGPRX1 |
| rs12364167R | Reverse Primer | PCR-RETINA | Breakpoint Refinement | MRGPRX1 |
| rs12364167In | Invader Probe | PCR-RETINA | Breakpoint Refinement | MRGPRX1 |
| rs12364167AL1 | Allele Probe 1 | PCR-RETINA | Breakpoint Refinement | MRGPRX1 |
| rs12364167AL2 | Allele Probe 2 | PCR-RETINA | Breakpoint Refinement | MRGPRX1 |
| rs2220067F | Forward Primer | PCR-RETINA | Breakpoint Refinement | MRGPRX1 |
| rs2220067R | Reverse Primer | PCR-RETINA | Breakpoint Refinement | MRGPRX1 |
| rs2220067In | Invader Probe | PCR-RETINA | Breakpoint Refinement | MRGPRX1 |
| rs2220067AL1 | Allele Probe 1 | PCR-RETINA | Breakpoint Refinement | MRGPRX1 |
| rs2220067AL2 | Allele Probe 2 | PCR-RETINA | Breakpoint Refinement | MRGPRX1 |
| rs11517776F | Forward Primer | PCR-RETINA | Breakpoint Refinement | MRGPRX1 |
| rs11517776R | Reverse Primer | PCR-RETINA | Breakpoint Refinement | MRGPRX1 |
| rs11517776In | Invader Probe | PCR-RETINA | Breakpoint Refinement | MRGPRX1 |
| rs11517776AL1 | Allele Probe 1 | PCR-RETINA | Breakpoint Refinement | MRGPRX1 |
| rs11517776AL2 | Allele Probe 2 | PCR-RETINA | Breakpoint Refinement | MRGPRX1 |
| rs2016258F | Forward Primer | PCR-RETINA | Breakpoint Refinement | MRGPRX1 |
| rs2016258R | Reverse Primer | PCR-RETINA | Breakpoint Refinement | MRGPRX1 |
| rs2016258In | Invader Probe | PCR-RETINA | Breakpoint Refinement | MRGPRX1 |
| rs2016258AL1 | Allele Probe 1 | PCR-RETINA | Breakpoint Refinement | MRGPRX1 |
| rs2016258AL2 | Allele Probe 2 | PCR-RETINA | Breakpoint Refinement | MRGPRX1 |
| rs7115805F | Forward Primer | PCR-RETINA | Breakpoint Refinement | MRGPRX1 |
| rs7115805R | Reverse Primer | PCR-RETINA | Breakpoint Refinement | MRGPRX1 |
| rs7115805In | Invader Probe | PCR-RETINA | Breakpoint Refinement | MRGPRX1 |
| rs7115805AL1 | Allele Probe 1 | PCR-RETINA | Breakpoint Refinement | MRGPRX1 |
| rs7115805AL2 | Allele Probe 2 | PCR-RETINA | Breakpoint Refinement | MRGPRX1 |
| rs7110426F | Forward Primer | PCR-RETINA | Breakpoint Refinement | MRGPRX1 |
| rs7110426R | Reverse Primer | PCR-RETINA | Breakpoint Refinement | MRGPRX1 |
| rs7110426In | Invader Probe | PCR-RETINA | Breakpoint Refinement | MRGPRX1 |
| rs7110426AL1 | Allele Probe 1 | PCR-RETINA | Breakpoint Refinement | MRGPRX1 |

TABLE 1-continued

| | | | | |
|---|---|---|---|---|
| rs7110426AL2 | Allele Probe 2 | PCR-RETINA | Breakpoint Refinement | MRGPRX1 |
| rs11024893 F | Forward Primer | PCR-RETINA | Breakpoint Refinement | MRGPRX1 |
| rs11024893 R | Reverse Primer | PCR-RETINA | Breakpoint Refinement | MRGPRX1 |
| rs11024893 In | Invader Probe | PCR-RETINA | Breakpoint Refinement | MRGPRX1 |
| rs11024893 AL1 | Allele Probe 1 | PCR-RETINA | Breakpoint Refinement | MRGPRX1 |
| rs11024893 AL2 | Allele Probe 2 | PCR-RETINA | Breakpoint Refinement | MRGPRX1 |
| rs2007048F | Forward Primer | PCR-RETINA | Breakpoint Refinement | MRGPRX1 |
| rs2007048R | Reverse Primer | PCR-RETINA | Breakpoint Refinement | MRGPRX1 |
| rs2007048In | Invader Probe | PCR-RETINA | Breakpoint Refinement | MRGPRX1 |
| rs2007048AL1 | Allele Probe 1 | PCR-RETINA | Breakpoint Refinement | MRGPRX1 |
| rs2007048AL2 | Allele Probe 2 | PCR-RETINA | Breakpoint Refinement | MRGPRX1 |
| rs7117716FP | Forward Primer | PCR-RETINA | Breakpoint Refinement | MRGPRX1 |
| rs7117716RP | Reverse Primer | PCR-RETINA | Breakpoint Refinement | MRGPRX1 |
| rs7117716IN | Invader Probe | PCR-RETINA | Breakpoint Refinement | MRGPRX1 |
| rs7117716AL1 | Allele Probe 1 | PCR-RETINA | Breakpoint Refinement | MRGPRX1 |
| rs7117716AL2 | Allele Probe 2 | PCR-RETINA | Breakpoint Refinement | MRGPRX1 |
| rs10786512F | Forward Primer | PCR-RETINA | Breakpoint Refinement | MRGPRX1 |
| rs10786512R | Reverse Primer | PCR-RETINA | Breakpoint Refinement | MRGPRX1 |
| rs10786512IN | Invader Probe | PCR-RETINA | Breakpoint Refinement | MRGPRX1 |
| rs10786512AL1 | Allele Probe 1 | PCR-RETINA | Breakpoint Refinement | MRGPRX1 |
| rs10786512AL2 | Allele Probe 2 | PCR-RETINA | Breakpoint Refinement | MRGPRX1 |
| rs10832999F | Forward Primer | PCR-RETINA | Breakpoint Refinement | MRGPRX1 |
| rs10832999R | Reverse Primer | PCR-RETINA | Breakpoint Refinement | MRGPRX1 |
| rs10832999IN | Invader Probe | PCR-RETINA | Breakpoint Refinement | MRGPRX1 |
| rs10832999AL1 | Allele Probe 1 | PCR-RETINA | Breakpoint Refinement | MRGPRX1 |
| rs10832999AL2 | Allele Probe 2 | PCR-RETINA | Breakpoint Refinement | MRGPRX1 |
| rs10833052FP | Forward Primer | PCR-RETINA | Breakpoint Refinement | MRGPRX1 |
| rs10833052RP | Reverse Primer | PCR-RETINA | Breakpoint Refinement | MRGPRX1 |
| rs10833052IN | Invader Probe | PCR-RETINA | Breakpoint Refinement | MRGPRX1 |
| rs10833052AL1 | Allele Probe 1 | PCR-RETINA | Breakpoint Refinement | MRGPRX1 |
| rs10833052AL2 | Allele Probe 2 | PCR-RETINA | Breakpoint Refinement | MRGPRX1 |
| r s 11024867F | Forward Primer | PCR-RETINA | Breakpoint Refinement | MRGPRX1 |
| r s 11024867R | Reverse Primer | PCR-RETINA | Breakpoint Refinement | MRGPRX1 |
| r s 11024867IN | Invader Probe | PCR-RETINA | Breakpoint Refinement | MRGPRX1 |
| r s 11024867AL1 | Allele Probe 1 | PCR-RETINA | Breakpoint Refinement | MRGPRX1 |
| r s 11024867AL2 | Allele Probe 2 | PCR-RETINA | Breakpoint Refinement | MRGPRX1 |
| rs11599929F | Forward Primer | PCR-RETINA | Breakpoint Refinement | MRGPRX1 |
| rs11599929R | Reverse Primer | PCR-RETINA | Breakpoint Refinement | MRGPRX1 |
| rs11599929IN | Invader Probe | PCR-RETINA | Breakpoint Refinement | MRGPRX1 |

TABLE 1-continued

| | | | | |
|---|---|---|---|---|
| rs11599929AL1 | Allele Probe 1 | PCR-RETINA | Breakpoint Refinement | MRGPRX1 |
| rs11599929AL2 | Allele Probe 2 | PCR-RETINA | Breakpoint Refinement | MRGPRX1 |
| rs1842921F | Forward Primer | PCR-RETINA | Breakpoint Refinement | MRGPRX1 |
| rs1842921R | Reverse Primer | PCR-RETINA | Breakpoint Refinement | MRGPRX1 |
| rs1842921IN | Invader Probe | PCR-RETINA | Breakpoint Refinement | MRGPRX1 |
| rs1842921AL1 | Allele Probe 1 | PCR-RETINA | Breakpoint Refinement | MRGPRX1 |
| rs1842921AL2 | Allele Probe 2 | PCR-RETINA | Breakpoint Refinement | MRGPRX1 |
| rs2004383FP | Forward Primer | PCR-RETINA | Breakpoint Refinement | MRGPRX1 |
| rs2004383RP | Reverse Primer | PCR-RETINA | Breakpoint Refinement | MRGPRX1 |
| rs2004383IN | Invader Probe | PCR-RETINA | Breakpoint Refinement | MRGPRX1 |
| rs2004383AL1 | Allele Probe 1 | PCR-RETINA | Breakpoint Refinement | MRGPRX1 |
| rs2004383AL2 | Allele Probe 2 | PCR-RETINA | Breakpoint Refinement | MRGPRX1 |
| rs2004384FP | Forward Primer | PCR-RETINA | Breakpoint Refinement | MRGPRX1 |
| rs2004384RP | Reverse Primer | PCR-RETINA | Breakpoint Refinement | MRGPRX1 |
| rs2004384IN | Invader Probe | PCR-RETINA | Breakpoint Refinement | MRGPRX1 |
| rs2004384AL1 | Allele Probe 1 | PCR-RETINA | Breakpoint Refinement | MRGPRX1 |
| rs2004384AL2 | Allele Probe 2 | PCR-RETINA | Breakpoint Refinement | MRGPRX1 |
| rs3858489F | Forward Primer | PCR-RETINA | Breakpoint Refinement | MRGPRX1 |
| rs3858489R | Reverse Primer | PCR-RETINA | Breakpoint Refinement | MRGPRX1 |
| rs3858489IN | Invader Probe | PCR-RETINA | Breakpoint Refinement | MRGPRX1 |
| rs3858489AL1 | Allele Probe 1 | PCR-RETINA | Breakpoint Refinement | MRGPRX1 |
| rs3858489AL2 | Allele Probe 2 | PCR-RETINA | Breakpoint Refinement | MRGPRX1 |
| rs4756975FP | Forward Primer | PCR-RETINA | Breakpoint Refinement | MRGPRX1 |
| rs4756975RP | Reverse Primer | PCR-RETINA | Breakpoint Refinement | MRGPRX1 |
| rs4756975IN | Invader Probe | PCR-RETINA | Breakpoint Refinement | MRGPRX1 |
| rs4756975AL1 | Allele Probe 1 | PCR-RETINA | Breakpoint Refinement | MRGPRX1 |
| rs4756975AL2 | Allele Probe 2 | PCR-RETINA | Breakpoint Refinement | MRGPRX1 |
| r s 4757736FP | Forward Primer | PCR-RETINA | Breakpoint Refinement | MRGPRX1 |
| r s 4757736RP | Reverse Primer | PCR-RETINA | Breakpoint Refinement | MRGPRX1 |
| r s 4757736IN | Invader Probe | PCR-RETINA | Breakpoint Refinement | MRGPRX1 |
| r s 4757736AL1 | Allele Probe 1 | PCR-RETINA | Breakpoint Refinement | MRGPRX1 |
| r s 4757736AL2 | Allele Probe 2 | PCR-RETINA | Breakpoint Refinement | MRGPRX1 |
| rs6483561F | Forward Primer | PCR-RETINA | Breakpoint Refinement | MRGPRX1 |
| rs6483561R | Reverse Primer | PCR-RETINA | Breakpoint Refinement | MRGPRX1 |
| rs6483561IN | Invader Probe | PCR-RETINA | Breakpoint Refinement | MRGPRX1 |
| rs6483561AL1 | Allele Probe 1 | PCR-RETINA | Breakpoint Refinement | MRGPRX1 |
| rs6483561AL2 | Allele Probe 2 | PCR-RETINA | Breakpoint Refinement | MRGPRX1 |
| rs7116303F | Forward Primer | PCR-RETINA | Breakpoint Refinement | MRGPRX1 |
| rs7116303R | Reverse Primer | PCR-RETINA | Breakpoint Refinement | MRGPRX1 |
| rs7116303IN | Invader Probe | PCR-RETINA | Breakpoint Refinement | MRGPRX1 |

TABLE 1-continued

| | | | | |
|---|---|---|---|---|
| rs7116303AL1 | Allele Probe 1 | PCR-RETINA | Breakpoint Refinement | MRGPRX1 |
| rs7116303AL2 | Allele Probe 2 | PCR-RETINA | Breakpoint Refinement | MRGPRX1 |
| rs7120561FP | Forward Primer | PCR-RETINA | Breakpoint Refinement | MRGPRX1 |
| rs7120561RP | Reverse Primer | PCR-RETINA | Breakpoint Refinement | MRGPRX1 |
| rs7120561IN | Invader Probe | PCR-RETINA | Breakpoint Refinement | MRGPRX1 |
| rs7120561AL1 | Allele Probe 1 | PCR-RETINA | Breakpoint Refinement | MRGPRX1 |
| rs7120561AL2 | Allele Probe 2 | PCR-RETINA | Breakpoint Refinement | MRGPRX1 |
| rs7946938F | Forward Primer | PCR-RETINA | Breakpoint Refinement | MRGPRX1 |
| rs7946938R | Reverse Primer | PCR-RETINA | Breakpoint Refinement | MRGPRX1 |
| rs7946938IN | Invader Probe | PCR-RETINA | Breakpoint Refinement | MRGPRX1 |
| rs7946938AL1 | Allele Probe 1 | PCR-RETINA | Breakpoint Refinement | MRGPRX1 |
| rs7946938AL2 | Allele Probe 2 | PCR-RETINA | Breakpoint Refinement | MRGPRX1 |
| rs881504F | Forward Primer | PCR-RETINA | Breakpoint Refinement | MRGPRX1 |
| rs881504R | Reverse Primer | PCR-RETINA | Breakpoint Refinement | MRGPRX1 |
| rs881504IN | Invader Probe | PCR-RETINA | Breakpoint Refinement | MRGPRX1 |
| rs881504AL1 | Allele Probe 1 | PCR-RETINA | Breakpoint Refinement | MRGPRX1 |
| rs881504AL2 | Allele Probe 2 | PCR-RETINA | Breakpoint Refinement | MRGPRX1 |

| Primer/Probe Name | Sequence | SEQ ID NO: |
|---|---|---|
| rs2114912A | GGCCTGCGCCTCCACAGGTGGCTGATGACGGGGCTCTCCAGCCTAAAACGCTGGAAGGCTTAGTGCCTGGAGTGCCCTCC | 1 |
| rs2114912C | GGCCTGCGCCTCCACAGGTGGCTGATGACGGGGCTCTCCAGCCTCAAACGCTGGAAGGCTTAGTGCCTGGAGTGCCCTCC | 2 |
| rs2114912F | GGCTGATGACGGGGCTCT | 3 |
| rs2114912R | CCAGGCACTAAGCCTTCCAG | 4 |
| rs2114912 In | CACTCCAGGCACTAAGCCTTCCAGCGTTTC | 5 |
| rs2114912 AL1 | ATGACGTGGCAGACTAGGCTGGAGAGCC | 6 |
| rs2114912 AL2 | CGCGCCGAGGGAGGCTGGAGAGCC | 7 |
| PCR 1F | CTGGGCTGGGAGCAGCCTC | 8 |
| PCR 1R | CACTCGCTGGCCTGTTTCATGTC | 9 |
| PCR 2F | CTGGAATCCGGTGTCGAAGTGG | 10 |
| PCR 2R | CTCGGCCCCTGCACTGTTTC | 11 |
| CYP2D6*10-100 C > T In | GCAGTGGCAGGGGCCTGGTGT | 12 |
| CYP2DT*10-100 C > T AL1 | ATGACGTGGCAGACGGTAGCGTGCAGC | 13 |
| CYP2D6*10-100 C > T AL2 | CGCGCCGAGGAGTAGCGTGCAGCC | 14 |
| CYP2D6*4-1844 G > A In | CCTTACCCGCATCTCCCACCGGCAT | 15 |
| CYP2D6*4-1846 G > A AL1 | CGCGCCGAGGAGACGCCCCTTTCG | 16 |
| CYP2D6*4-1846 G > A AL2 | ATGACGTGGCAGACGGACGCCCCTTTCG | 17 |

TABLE 1-continued

| | | |
|---|---|---|
| CYP2D6*2-2850 C > T In | GGCAGAGAACAGGTCAGCCACCACTATGCT | 18 |
| CYP2D6*2-2850 C > T AL1 | ATGACGTGGCAGACGCAGGTTCTCATCATTGAA | 19 |
| CYP2D6*2-2850 C > T AL2 | CGCGCCGAGGACAGGTTCTCATCATTGAAG | 20 |
| CYP2D6 Reported Copy number F | GGTGTCCCAGCAAAGTTCATG | 21 |
| CYP2D6 Reported Copy number R | CCTCCTGCTCATGATCCTACATC | 22 |
| CYP2D6 Reported Copy number T | FAM-CCCCCGCCTGTACC | 23 |
| CYP2D6 Designed Copy number R | ACTTCGACACCGGATTCCAG | 24 |
| DPKUP | GTTATCCCAGAAGGCTTTGCAGGCTTGA | 25 |
| DPKLDW | GCCGACTGAGCCCTGGGAGGTAGGTA | 26 |
| 2 D6SeqF | TGTTCTCTGCCGGGATGG | 27 |
| 2 D6SeqR | GCCCTATCACGTCGTCGATC | 28 |
| rs3858489F | GTGTCACAACCACCTGTTTGCA | 29 |
| rs3858489R | TCCAAGGTTGAGATGGTTGGA | 30 |
| rs3858489 In | GGGTCCTCAAATCCAGTTTGAAATCCAGTTCTTGA | 31 |
| rs3858489 AL1 | CGCGCCGAGGTTGACTCTGAAGCCTGAC | 32 |
| rs3858489 AL2 | ATGACGTGGCAGACCTGACTCTGAAGCCTGA | 33 |
| rs11599929F | TGGATCCATAAAAATAGGAAAAACTGA | 34 |
| rs11599929R | TCAGATTTCATCACAGTCGCG | 35 |
| rs11599929 In | GGATCCACAGAGAATCCTGATCAGCAGGACA | 36 |
| rs11599929 AL1 | CGCGCCGAGGTAGGCTGGACCCACAG | 37 |
| rs11599929 AL2 | ATGACGTGGCAGACCAGGCTGGACCCAC | 38 |
| rs4756975F | GGCCTTGGTTTCTAGTAAAGACAACT | 39 |
| rs4756975R | GCCAAAATAGAACTGGGGCA | 40 |
| rs4756975 In | ACTGGTCCATTAGTGCAGGAAGAGCTAAATAAGCACA | 41 |
| rs4756975 AL1 | CGCGCCGAGGTTAAAGTTCT CAAGGGGAAG | 42 |
| rs4756975AL2 | ATGACGTGGCAGACGTAAAAGTTCT CAAGGGGAA | 43 |
| MRGPRX1 copy number F | TTAAGCTTCATCAGTATCCCCCA | 44 |
| MRGPRX1 copy number R | CAAAGTAGGAAAACATCATCACAGGA | 45 |
| MRGPRX1 copy number T | ACCATCTCTAAAATCCT | 46 |
| MRGPR5'2copyFP (CA1) | GATCTAGCTAAGAGACAGAGATAGACACATG | 47 |
| MRGPR5'2copyRP (CA1) | CCAAAGAGTTTTCTGTACTCATTATCTTCA | 48 |
| MRGPR5'2copyT (CA1) | FAM-AAGATATGAGGAAGGGTGAGAA | 49 |

TABLE 1-continued

| | | |
|---|---|---|
| MRGPR5'3copyFP (CA2) | GGAGTGGGATAACAATTTTCTTCA | 50 |
| MRGPR5'3copyRP (CA2) | ACTTGACATTGAGTTTAATACTCCTGTTTT | 51 |
| MRGPR5'3copyT (CA2) | FAM-AATGTCTGCGGTTAATAT | 52 |
| MRGPR3'3copyFP (CA3) | AGAACCCTTCTGTGTTGCTTAATTC | 53 |
| MRGPR3'3copyRP (CA3) | TGTCTCCAATACCTCTGGCCA | 54 |
| MRGPR3'copyT (CA3) | FAM-TGCATACAGGAGCTGGA | 55 |
| MRGPR3'2copyFP (CA4) | GAGAAGCAAGAGCAAGCAACTTC | 56 |
| MRGPR3'2copyRP (CA4) | TAGCTAGTGGTCTATCTATCTTGTTAATGTTTT | 57 |
| MRGPR3'2copyT (CA4) | FAM-AAGGAGCTAGAAACACGAAA | 58 |
| rs958061F | AGCTGCTTGAGAAAAATACCGAGTA | 59 |
| rs958061R | TGTTAGTGACATTCTTTTTCTTTGACAGA | 60 |
| rs958061 In | GACCTCAGAGTGTGGTAGGAGAGAAAGATGTGTG T | 61 |
| rs958061AL1 | ATGACGTGGCAGACGACAAATAATTCAAGTACACTGTTATAA | 62 |
| rs958061AL2 | CGCGCCGAGGAAGAAATAATTGAAGTACACTGTTATAAG | 63 |
| rs12364167F | CAACAAACCTAATATAAAAGGCCCTC | 64 |
| rs12364167R | CAAAAATAATCTTTAAATACATGCACTGC | 65 |
| rs12364167In | GCAGACCAATGTATATATTGTATGACGAAGCTATATAGTTGCTTTATCAGA | 66 |
| rs12364167AL1 | ATGACGTGGCAGACCAAATATTTGCAAATTAATGCAAAATTATTAATAA | 67 |
| rs12364167AL2 | CGCGCCGAGGTAAATATTTGCAAATTAATGCAAAATTATTAATAAG | 68 |
| rs2220067F | ATTTCCAATATTTTGCATTTGCTG | 69 |
| rs2220067R | TCAAAAGAACTCTCCACTCCAAATT | 70 |
| rs2220067In | GAAGTGTTTTACTTCCAATTATGTGGTCAATTTTAGAAGAAGTGCTACT | 71 |
| rs2220067AL1 | ATGACGTGGCAGACGTGGCACTGAGAAGAATGT | 72 |
| rs2220067AL2 | CGCGCCGAGGATGGCACTGAGAAGAATGTG | 73 |
| rs11517776F | AAAGGCCTAGGAATACAATGTACAAGG | 74 |
| rs11517776R | TCAAGGGTAGCTTGATGGGAATA | 75 |
| rs11517776In | TTCATACCCATGAGAATGGAATTTTTTGGATTTGTTTGTGTCCTCTCA | 76 |
| rs11517776AL1 | ATGACGTGGCAGACTTACTTCCTTGAGCAGTG | 77 |
| rs11517776AL2 | CGCGCCGAGGCTACTTCCTTGAGCAGTG | 78 |
| rs2016258F | GCAGGATGCAAACACAAGGAA | 79 |
| rs2016258R | TCTCTCCTTGCCCAATAGAAAAT | 80 |
| rs2016258In | CTTGCCCAATACAAAAATTTAGGTGACTGGCAAAATTTACTAGGGTATAATTACAATAT | 81 |
| rs2016258AL1 | ATGACGTGGCAGACGTAATGCTGGGTTAATTGTAG | 82 |
| rs2016258AL2 | CGCGCCGAGGATAATGCTGGGTTAATTGTAGT | 83 |
| rs7115805F | CATGACTCAGTATGGAAGAAGACAAA | 84 |

TABLE 1-continued

| | | |
|---|---|---|
| rs7115805R | TGTCTCCAATACCTCTGGCCA | 85 |
| rs7115805In | ATACAGGAGCTGGAGTCAAAGCTGGTGAGCT | 86 |
| rs7115805AL1 | ATGACGTGGCAGACGATCCAGGCTTATGAAGATG | 87 |
| rs7115805AL2 | CGCGCCGAGGAATCCAGGCTTATGAAGATGC | 88 |
| rs7110426F | CTAAAAACCATTAAGTTTTATAGCATACAGTG | 89 |
| rs7110426R | AAAATCTAACAAATTCTGCAGGGC | 90 |
| rs7110426In | TACAGTCAAAAACTGGTAACAGCCAAAATGGCCATCAATACTGA | 91 |
| rs7110426AL1 | CGCGCCGAGGTATAAATTACTGTCTATCTATGCAATAG | 92 |
| rs7110426AL2 | ATGACGTGGCAGACCATAAATTACTGTCTATCTATGCAATA | 93 |
| rs11024893 F | CAGAAAGCTGAAAAGGCTTGAAA | 94 |
| rs11024893 R | TGTCTATTTGATTCTTCTCTTCTTCTTTAC | 95 |
| rs11024893 In | GA GCTAGAAACACGAAAACCCTTGAAAAAAATCAATGAATCCAGAAGCTGT | 96 |
| rs11024893 AL1 | ATGACGTGGCAGACGCTTTTTGAAA ACATTAACAA GATAG | 97 |
| rs11024893 AL2 | CGCCCGAGGCCTTTTCAAA ACATTAACAA GATAG | 98 |
| rs2007048F | CTAACATGTATAATCAACACAGAGTGGC | 99 |
| rs2007048R | AGAATGAGTGTTATTGGGATATGGACA | 100 |
| rs2007048In | CCTGCTGGCCTCAAATGATACTATATAAGTCCCAGAACT | 101 |
| rs2007048AL1 | ATGACGTGGCAGACGAATAATTCACTCTTTTTGTGTAC | 102 |
| rs2007048AL2 | CGCCCCGAGGAAATAATTCACTCTTTTTGTGTACC | 103 |
| rs7117716FP | GACTGAGCCTGCATGTCACCT | 104 |
| rs7117716RP | GACCCATATTTGCAGGACAAGAT | 105 |
| rs7117716IN | CTCCACCTGTAGATCCATTTCAACAACTGATTAGGTGCCA | 106 |
| rs7117716AL1 | ATGACGTGGCAGACCGAAGCATTTATATGTCTATA AATTTC | 107 |
| rs7117716AL2 | CGCGCCGAGGTGAAGCATTTATATGTCTATAAATTTCT | 108 |
| rs10786512F | TTTGTAAATTTGGCATATAGGTTAGAAGAT | 109 |
| rs10786512R | CACCTGAAAATTGAACCAAAGACTG | 110 |
| rs10786512IN | GGCATATAGGTTAGAAGATAATATGATATCTTATATGAACTTAAAGTATTCTTAGAGTGAATAGT | 111 |
| rs10786512AL1 | CGCCCCGAGGAAAAGGAATATTACTGAAATCAAAATAACC | 112 |
| rs10786512AL2 | ATGACGTGGCAGACGAAAAGGAATATTACTGAAATCAAATAAC | 113 |
| rs10832999F | AGGACATGGTAATAAGCAACTTTTGA | 114 |
| rs10832999R | CCACCAGCCAACTCAGGG | 115 |
| rs10832999IN | GGACATGGTAATAAGCAACTTTTGATGAATTTACATTGTGTGGGCTTTATGTCAC | 116 |
| rs10832999AL1 | CGCGCCGAGGATTACTTATTCAGATTCATGATCC | 117 |
| rs10832999AL2 | ATGACGTGGCAGACTTTACTTATTCAGATTCATGATCC | 118 |
| rs10833052FP | GGAGGTGAGAGAAAGTGATATAACCAG | 119 |
| rs10833052RP | TGTAAGTTTATGATTTTGGCTTCTCTAAAA | 120 |
| rs10833052IN | GAGCCTTGATGTTTGATGTCTTAGAGTTATCAGCCCAAGTCTAT | 121 |
| rs10833052AL1 | ATGACGTGGCAGACGTAAACATTCTTTTTGATTATCACTATAATA | 122 |
| rs10833052AL2 | CGCGCCGAGGATAAACATTCTTTTTGATTATCACTATAATA G | 123 |
| r s 11024867F | GAAGGAGGAGGATATAGAAAGGTGG | 124 |

TABLE 1-continued

| | | |
|---|---|---|
| rs11024867R | TTAACATTATTCTTTGCCTATCAGGAAA | 125 |
| rs11024867IN | GGATTTGCTTTCCAATCTTCTCTACCCTGTTTGACAACCT | 126 |
| rs11024867AL1 | CGCGCCGAGGAAAGAGGGTGGCTTCTATG | 127 |
| rs11024867AL2 | ATGACGTGGCAGACCAAGAGGGTGGCTTCTAT | 128 |
| rs11599929F | TGGATCCATAAAAATAGGAAAAACTGA | 129 |
| rs11599929R | TCAGATTTCATCACAGTCGCG | 130 |
| rs11599929IN | GGATCCACAGAGAATGGTGATCAGCAGGACA | 131 |
| rs11599929AL1 | CGCGCCGAGGTAGGCTGGACCCACAG | 132 |
| rs11599929AL2 | ATGACGTGGCAGACCAGGCTGGACCCAC | 133 |
| rs1842921F | TCCAGTTGGTTCTTGCGAGTG | 134 |
| rs1842921R | GTGCTAGTTCTACATAAAAGCAACAGC | 135 |
| rs1842921IN | TCCAGTTGGTTCTTGCGAGTG | 136 |
| rs1842921AL1 | CGCGCCGAGGATGTATTAGTGAGAGAGTTATTTAAAG | 137 |
| rs1842921AL2 | ATGACGTGGCAGACGTGTATTAGTGAGAGAGTTATTTAAAA | 138 |
| rs2004383FP | TGGTTCATAATGCATGGTCTCCT | 139 |
| rs2004383RP | GGTGTCAGTTCTGTGTCCAAGGT | 140 |
| rs2004383IN | GAC CTCTCTCTACTGCCACACAAGTTCTGTGCTT | 141 |
| rs2004383AL1 | ATGACGTGGCAGACGACATGGGAATAACATTAGGA | 142 |
| rs2004383AL2 | CGCGCCGAGGAACATGGGAATAACATTAGGAT | 143 |
| rs2004384FP | TGGTTCATAATGCATGGTCTCCT | 144 |
| rs2004384RP | GGTGTCAGTTCTGTGTCCAAGGT | 145 |
| rs2004384IN | GGCCTGAAATTTTCTCTCAGGG GGAGGAATTCAGT | 146 |
| rs2004384AL1 | ATGACGTGGCAGACGTATGCAAAGAGGTGGTTG | 147 |
| rs2004384AL2 | CGCGCCGAGGATATGCAAAGAGGTGGTTGT | 148 |
| rs3858489F | GTGTCACAACCACCTCTTTGCA | 149 |
| rs3858489R | TCCAAGGTTGAGATGGTTGGA | 150 |
| rs3858489IN | GGGTCCTCAAATCCAGTTTGAAATCCAGTTCTTGA | 151 |
| rs3858489AL1 | CGCGCCGAGGTTGACTCTGAAGCCTGAC | 152 |
| rs3858489AL2 | ATGACGTGGCAGACCTGACTCTGAAGCCTGA | 153 |
| rs4756975FP | CCAAAATAGAACTGGGGCAG | 154 |
| rs4756975RP | CCTGTCATTTGTTCACAGCA | 155 |
| rs4756975IN | TCACTGGTCCATTAGTCCAGGAAGAGCTAAATAAGCACA | 156 |
| rs4756975AL1 | ATGACGTGGCAGACGTAAAAGTTCTCAAGGGGAAG | 157 |
| rs4756975AL2 | CGCGCCGACGTTAAAAGTTCTCAAGGGGAAGG | 158 |
| rs4757736FP | TTCCCAGGTGAGGACAAACTTT | 159 |
| rs4757736RP | CAGGCAAGGAGCTTTGATGTG | 160 |
| rs4757736IN | CCCAGAGTGGACTCTCCCAATAACCCTCT | 161 |
| rs4757736AL1 | CGCGCCGAGGAGCCTGAACTGAAGACATC | 162 |
| rs4757736AL2 | ATGACGTGGCAGACGGCCTGAACTGAAGACAT | 163 |

TABLE 1-continued

| | | |
|---|---|---|
| rs6483561F | CCGCTACTGACACTACTTACTCATCAA | 164 |
| rs6483561R | AACATTGGCAAAACATGAAAAGG | 165 |
| rs6483561IN | CAATGACTCCATGGCTTGGAATTCTGGAATATGATAATCTCCTCT | 166 |
| rs6483561AL1 | CGCGCCGAGGATTTTCTTCTTCCCCCGC | 167 |
| rs6483561AL2 | ATGACGTGGCAGACGTTTTCTTCTTCCCCCG | 168 |
| rs7116303F | CCCCTGCATGTAGCACGG | 169 |
| rs7116303R | CAAAAGAAAAAGGAAAGACAAGGGT | 170 |
| rs7116303IN | GGAGGTGGAAACACAGGAAAGTGATCTTGTAGCTAAAACGT | 171 |
| rs7116303AL1 | CGCGCCGAGGATAACTGACTA TAAAAGAAGA CAG | 172 |
| rs7116303AL2 | ATGACGTGGCAGACGTAACTGACTA TAAAAGAAGA CA | 173 |
| rs7120561FP | TTCTAAGGCCCAAACAGGGG | 174 |
| rs7120561RP | CAGTCATTAAGGGTGGCCATG | 175 |
| rs7120561IN | TCTAGGCAGAATATGTGGGGCAGCAAGAGACAGA | 176 |
| rs7120561AL1 | ATGACGTGGCAGACGACTCTGAGTTCAGCATTC | 177 |
| rs7120561AL2 | CGCGCCGAGGTACTCTGAGTTCAGCATTCTTT | 178 |
| rs7946938F | TTAATGATACATTGAGGACTGTTAAGGTG | 179 |
| rs7946938R | GGAAATCCTAAAAAGTGATTGATAGCTAT | 180 |
| rs7946938IN | CACTAGAAAAGGACTAGACTGAAGGGCTTTCCATTCTGA | 181 |
| rs7946938AL1 | CGCGCCGAGGTAGGTTTCAGCAAATAGAATTCC | 182 |
| rs7946938AL2 | ATGACGTGGCAGACCAGGTTTCAGCAAATAGAATTC | 183 |
| rs881504F | CAGAAAGTGAGAAAATACATGAAAGTCTCTC | 184 |
| rs881504R | TTGCTTGGCATCAGTCACTGTAT | 185 |
| rs881504IN | CAAACATTGAATCGTAATTAATCAAGCGCTGTGCTAATTCTAGATAAAAGT | 186 |
| rs881504AL1 | CGCGCCGAGGAAAACATGTTTCAAATAAGTCTCTCAC | 187 |
| rs881504AL2 | ATGACGTGGCAGACCAAACATCTTTCAAATAAGTCTCTC | 188 |

Results

Detection of Allele Asymmetry Using Artificial Templates

Figure 1:
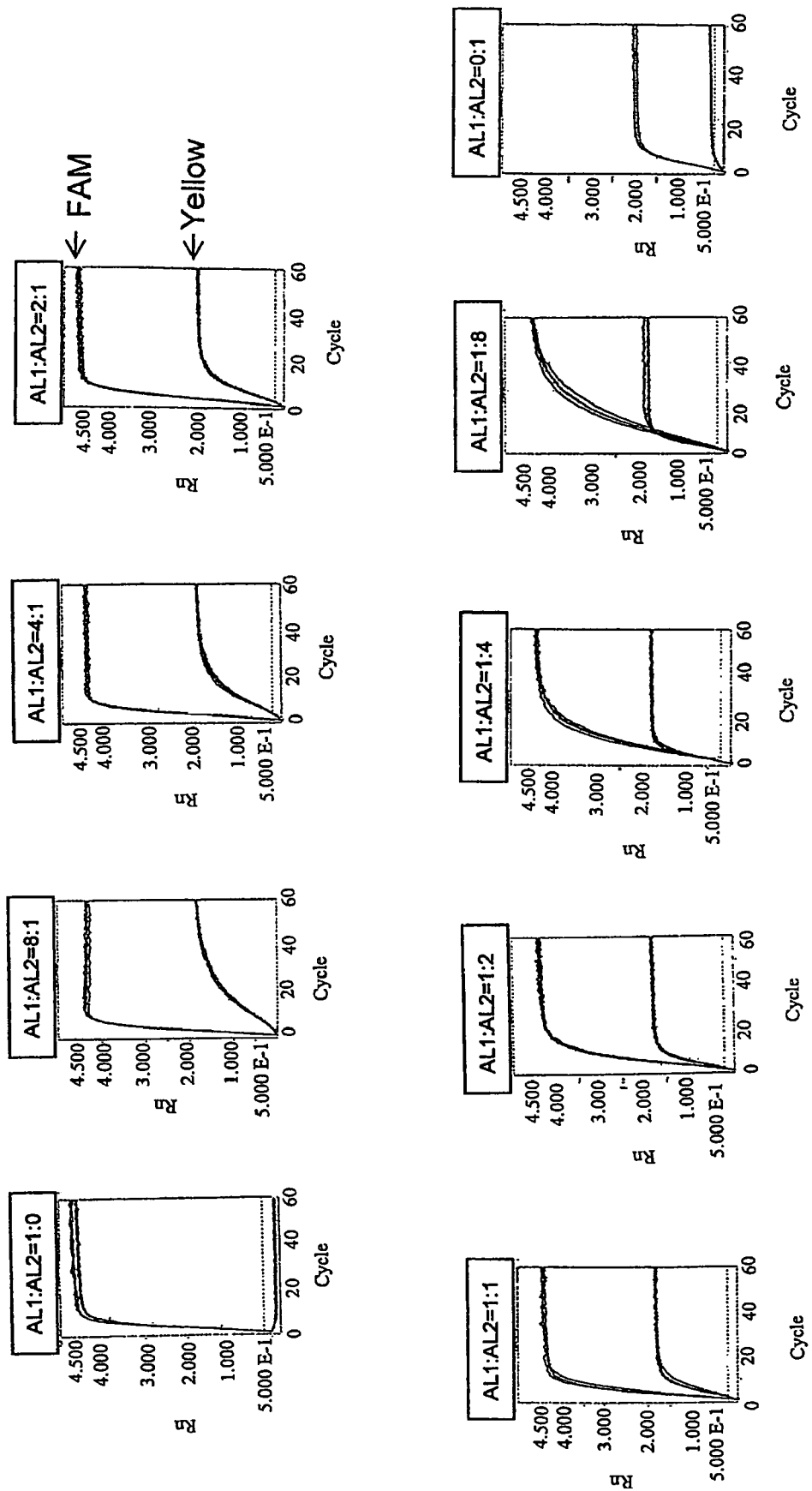
FIG. 1 shows the detection of allele asymmetry by PCR-RETINA using an artificial template. All experiments were performed in quadruplicate. (a) Real-time detection of fluorescence signals during invader assay. Plotted are reporter fluorescence signal values (FAM and Yakima Yellow) after normalization with Rox. The ordinate indicates normalized reporter signals (FAM or Yakima Yellow); the abscissa indicates reaction time at 30-second intervals. (b) Two-dimensional AD plot of PCR-RETINA after 3 minutes of the invader reaction. The ordinate indicates normalized FAM allele signals; the abscissa indicates normalized Yakima Yellow allele signals. (c) Two-dimensional AD plots at 0.5, 3, 10 and 30 minutes of the invader reaction. (d) Changes over time in cluster pattern showing allele asymmetry during 30 minutes of the invader reaction.
Figure 1:
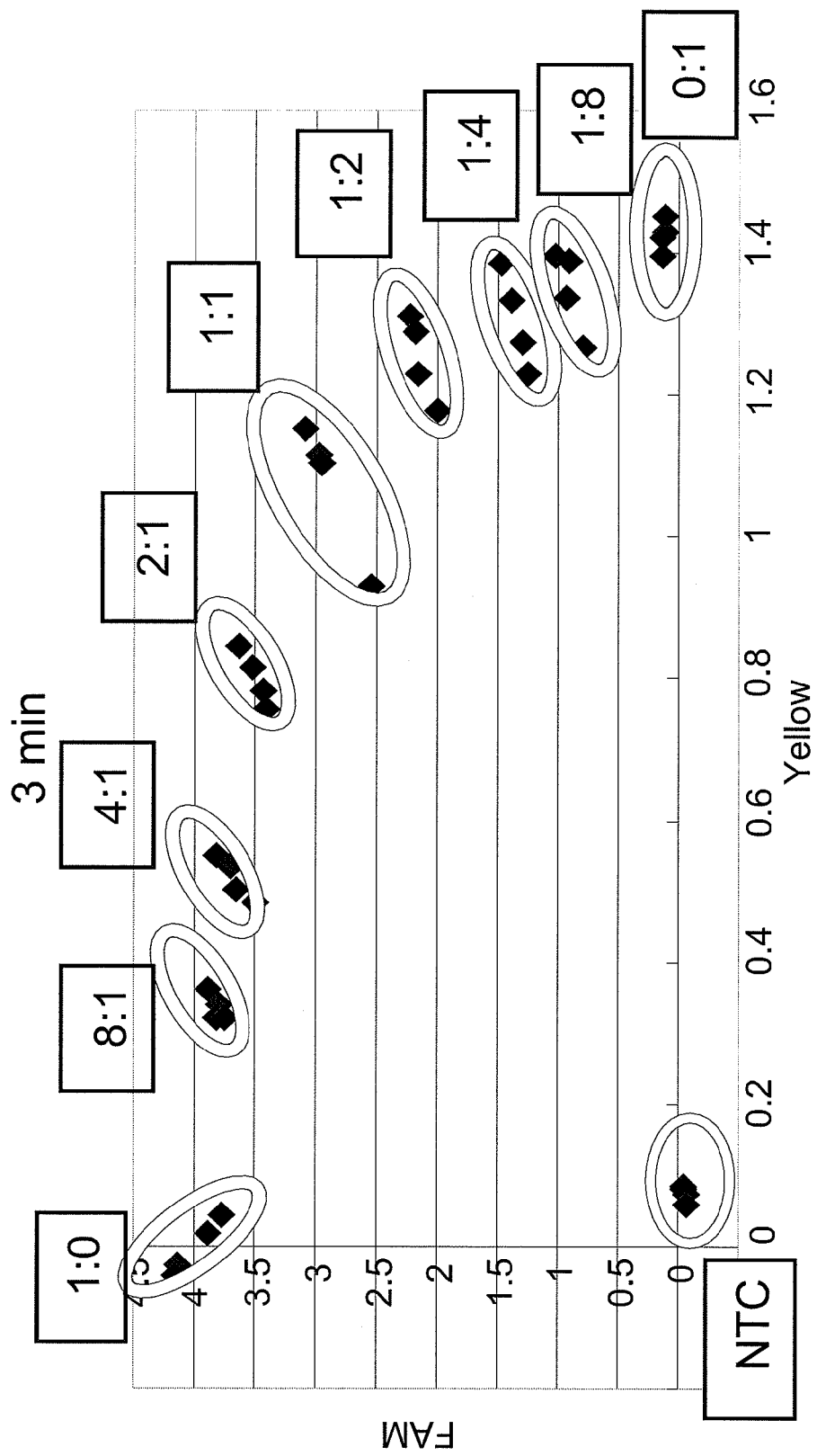
Figure 1:
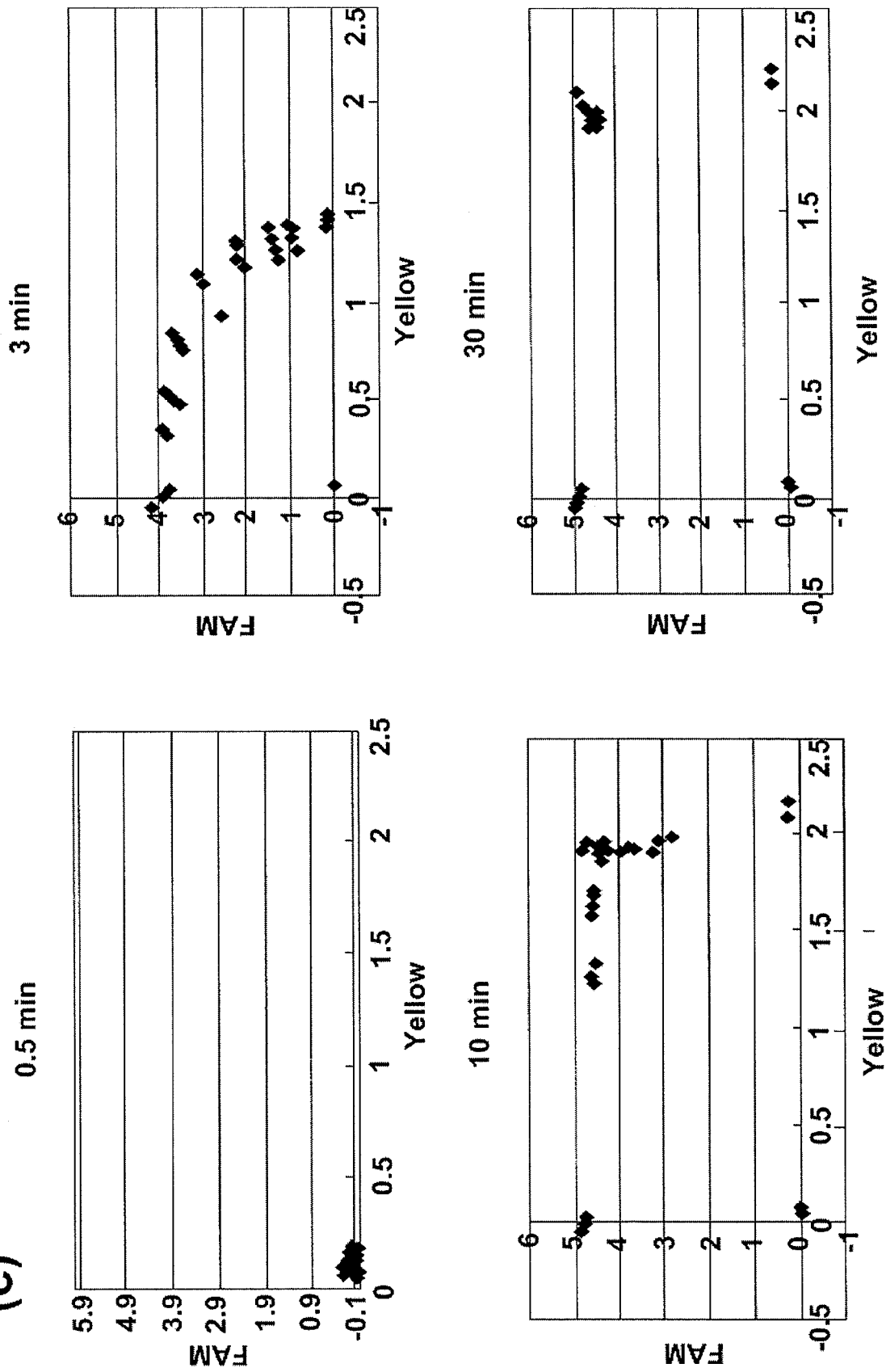
Figure 1:
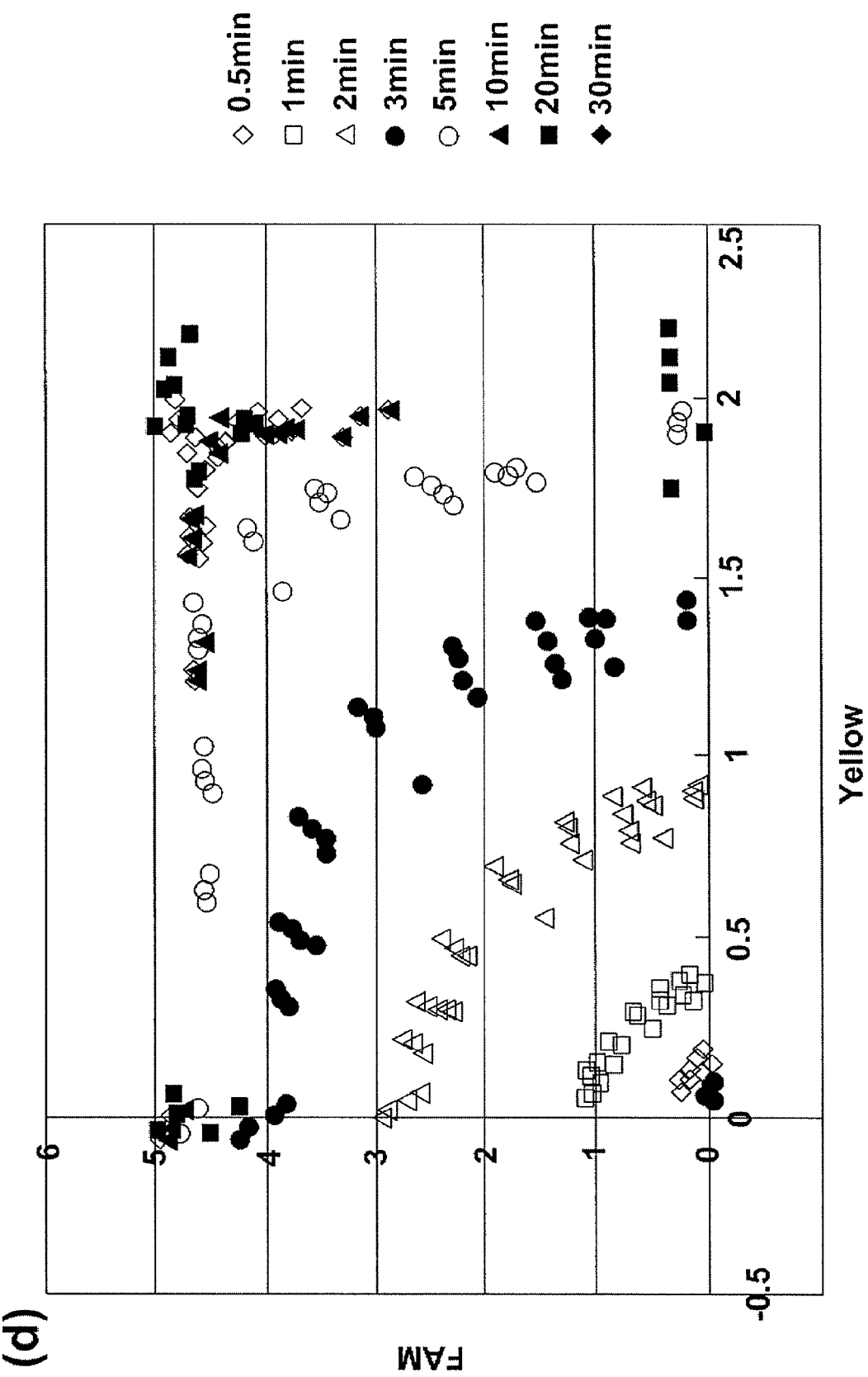

The present inventors developed mPCR-RETINA for the simultaneous detection of allele asymmetry at a plurality of SNP loci in a CNV region. First, two 80-base long oligonucleotide templates corresponding to the genomic sequence of the rs2114912 SNP locus were synthesized (Table 1). Standard samples having allele ratios ranging from 1:8 to 8:1 were prepared using these oligonucleotides. After DNA fragments were amplified by PCR, real-time fluorescence detection was performed every 30 seconds during 30 minutes of the invader reaction. Samples having various allele ratios were clearly separated in proportion to allele ratio in the initial stage of the reaction; however, after 30 minutes of the reaction, the samples merged into one heterozygote (FIG. 1). Among the allelic discrimination (AD) plots at various times, the best separation in cluster analysis was obtained just before saturation of the reaction.

Detection of Gene Multiplication In the Human Genome

Figure 2:
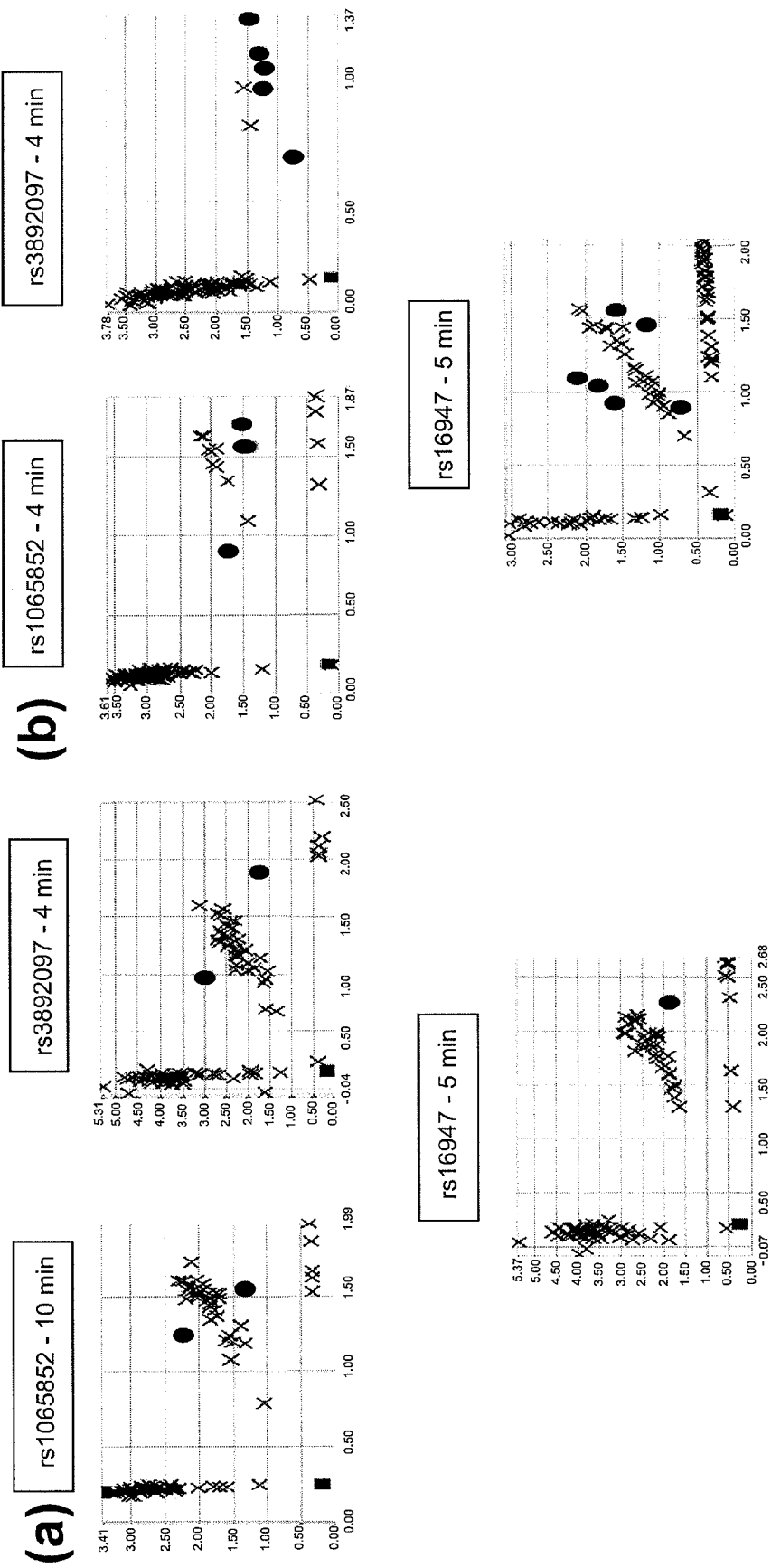
FIG. 2 shows the detection of multiplication of the CYP2D6 gene by PCR-RETINA. Two-dimensional AD plots of PCR-RETINA using CEU individuals (a) and YRI individuals (b). The alphanumeric characters in boxes indicate rs numbers and RETINA time points. Shown are two-dimensional AD plots at the point of inflection just before fluorescence intensity reaches a plateau. The ordinate of the AD plots indicates normalized FAM allele signals; the abscissa indicates normalized Yakima Yellow allele signals. ● represents an individual with allele asymmetry. X represents an individual plotted in a cluster of normal homozygotes or heterozygotes, or several individuals with undetermined type. ■ represents no template control (NTC). Copy number analysis of CYP2D6 by Taqman assay in CEU (c) and YRI (d). All reactions were performed in duplicate; mean copy number values are shown. Each open diamond (◇) represents an individual with allele asymmetry in PCR-RETINA.
Figure 2:
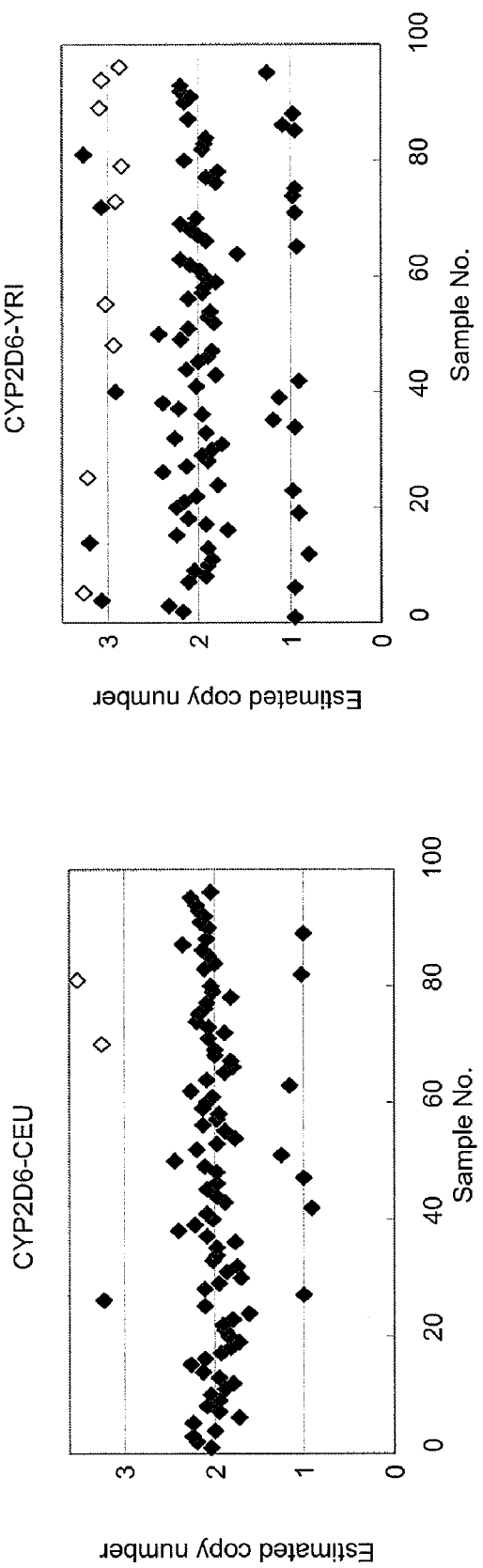

To determine whether PCR-RETINA is applicable to the detection of CNV using genomic DNA, the present inventors attempted to detect two CNVs corresponding to the CYP2D6 locus and MRGPRX1 locus, respectively. RETINA was performed using 90 CEU samples and 90 YRI samples used in the International HapMap project [International HapMap Consortium, 2005]. For CYP2D6, three reported SNPs were selected [Nevilie et al., 2002, ibid.]; for MRGPRX1, three SNPs were selected on the basis of information from the dbSNP database. In CYP2D6 assay, for at least one of the three loci, sample-derived dots were plotted outside the three major clusters in two CEU subjects and nine YRI subjects (FIGS. 2a and b). These 11 samples, plotted outside the clusters, were confirmed to have three copies of CYP2D6 by Taqman assay (FIGS. 2c and d). Meanwhile, PCR-RETINA failed to detect several individuals who were shown to have three copies or one copy by Taqman assay. These samples were found to comprise three copies of the same allele or deletion of one allele.

Figure 3:
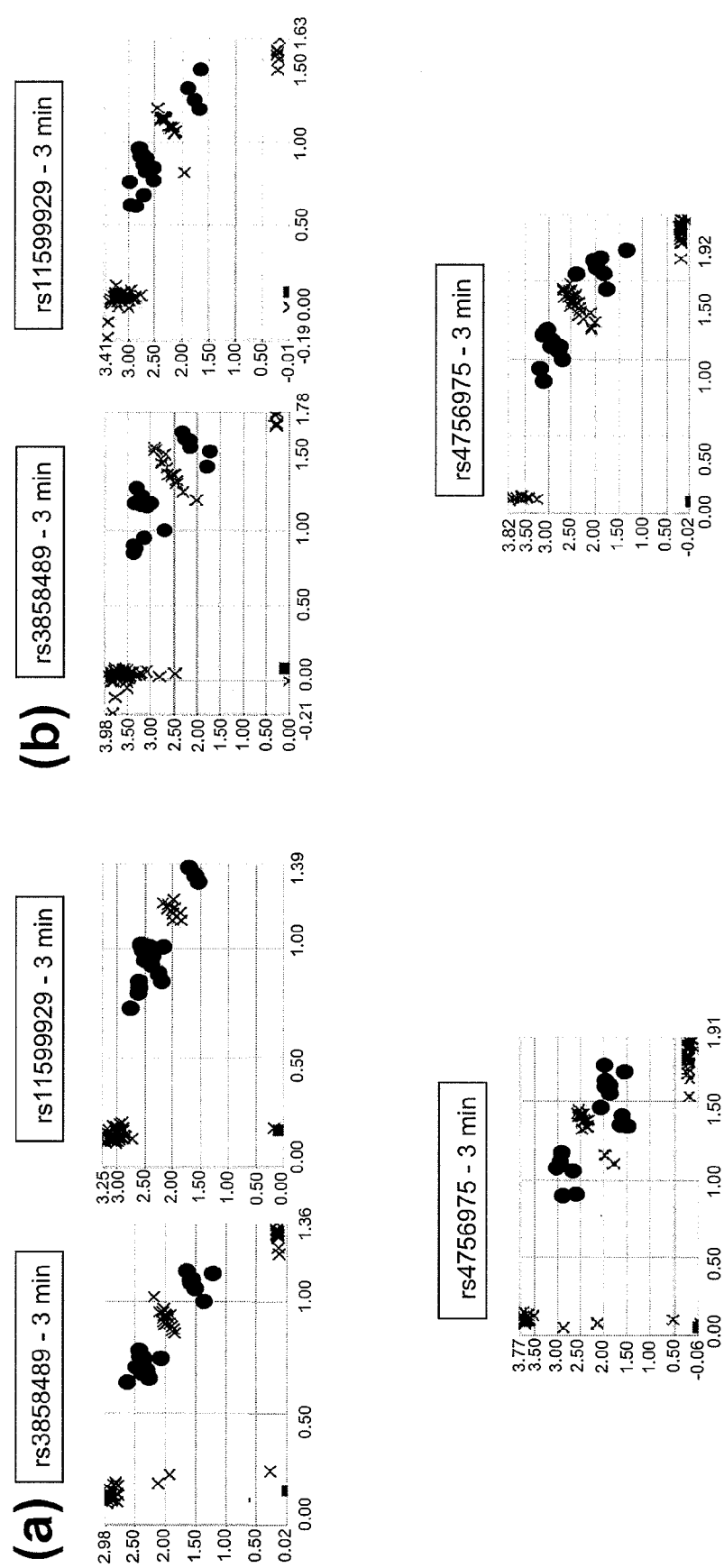
FIG. 3 shows the detection of multiplication of the MRG-PRX1 gene by PCR-RETINA. Shown are 2-dimensional AD plots of PCR-RETINA using CEU individuals (a) and YRI individuals (b). ● represents an individual with allele asymmetry. X represents an individual plotted in a cluster of normal homozygotes or heterozygotes, or several individuals with undetermined type. ■ represents no template control (NTC). Results of copy number analysis by Taqman assay in CEU (c) and YRI (d).
Figure 3:
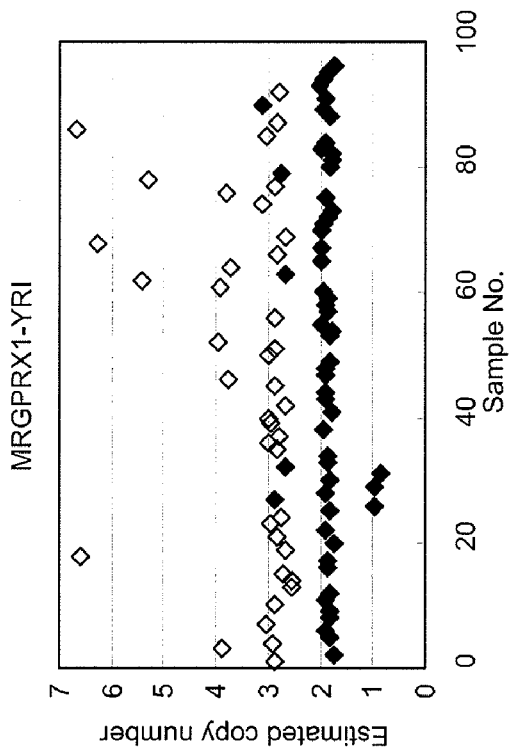
Figure 3:
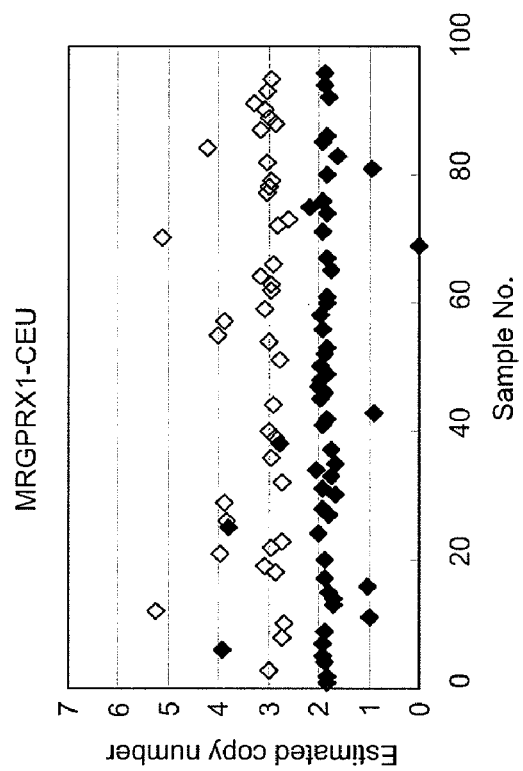

PCR-RETINA analysis for the MRGPRX1 locus detected a large number of individuals outside the major clusters in AD plots in both populations; these samples were confirmed to have three copies or more of multiplication by Taqman assay (FIG. 3). In this assay, PCR-RETINA failed to identify several individual subjects having four copies. These individuals were found to have two copies of both alleles, plotted in a heterozygote cluster. These experiments showed that PCR-RETINA is capable of detecting samples with allele asymmetry, but is incapable of detecting deletion, homo-multiplication, and multiplication accompanied by allele symmetry.

In the experiment for CYP2D6, a disagreement between the results of PCR-RETINA and Taqman assay was observed in two YRI samples. These samples were estimated to have one copy (deletion) by Taqman assay, but were judged to be heterozygotes by PCR-RETINA. DNA sequencing of these two samples demonstrated 3-base insertion that had not been reported previously (4578-4579 insCAT in M33388) in a region corresponding to the reverse primer sequence of Taqman assay. To demonstrate that this insertion led to the disagreement, a new reverse primer was designed to avoid this insertion, and copy number analysis was performed again by Taqman assay. As a result, the disagreement was no longer observable, confirming the accuracy of the results of PCR-RETINA.

Estimation of Allele Copy Numbers

Figure 4:
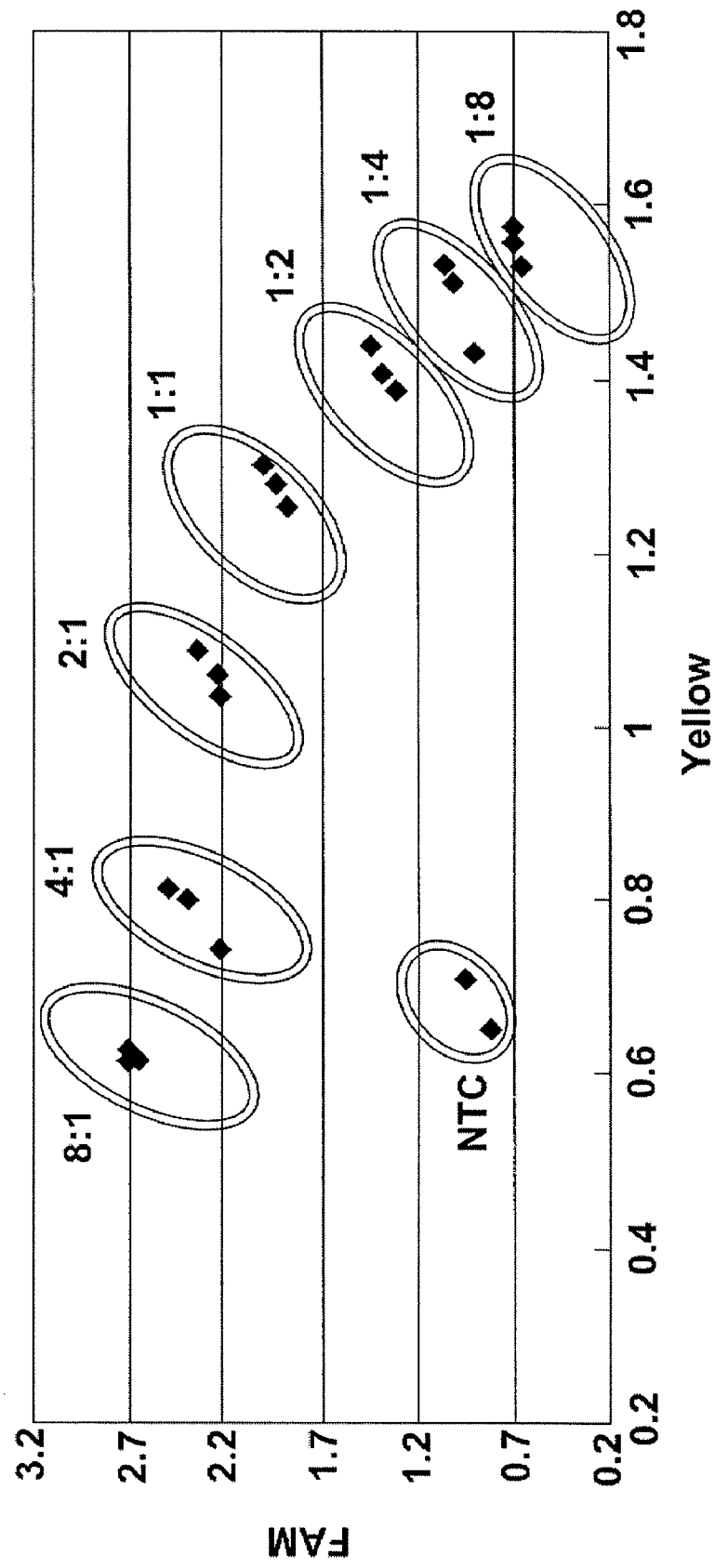
FIG. 4 shows the confirmation of allele copy numbers by the standard curve method. (a) AD plots of standard samples with various allele ratios (8:1, 4:1, 2:1, 1:1, 1:2, 1:4 and 1:8) after 3 minutes of the invader reaction. (b) A standard curve generated using standard samples with known allele ratios. (c) Total copy numbers estimated by Taqman assay. Each triangle, square, and circle represents an individual with 3 copies, 4 copies and 5 copies, respectively. Each diamond represents an individual with 2 copies, 1 copy or 0 copies. (d) AD plot of CEU samples after 3 minutes of RETINA reaction. Each circle, diamond, and oval represents an individual with 3 copies, 4 copies, and 5 copies, respectively. Triangles represent an individual with 2 copies, 1 copy, or 0 copies. Each square represents no template control (NTC). The numerical figures in the AD plots are estimated allele ratios calculated using the standard curve.
Figure 4:
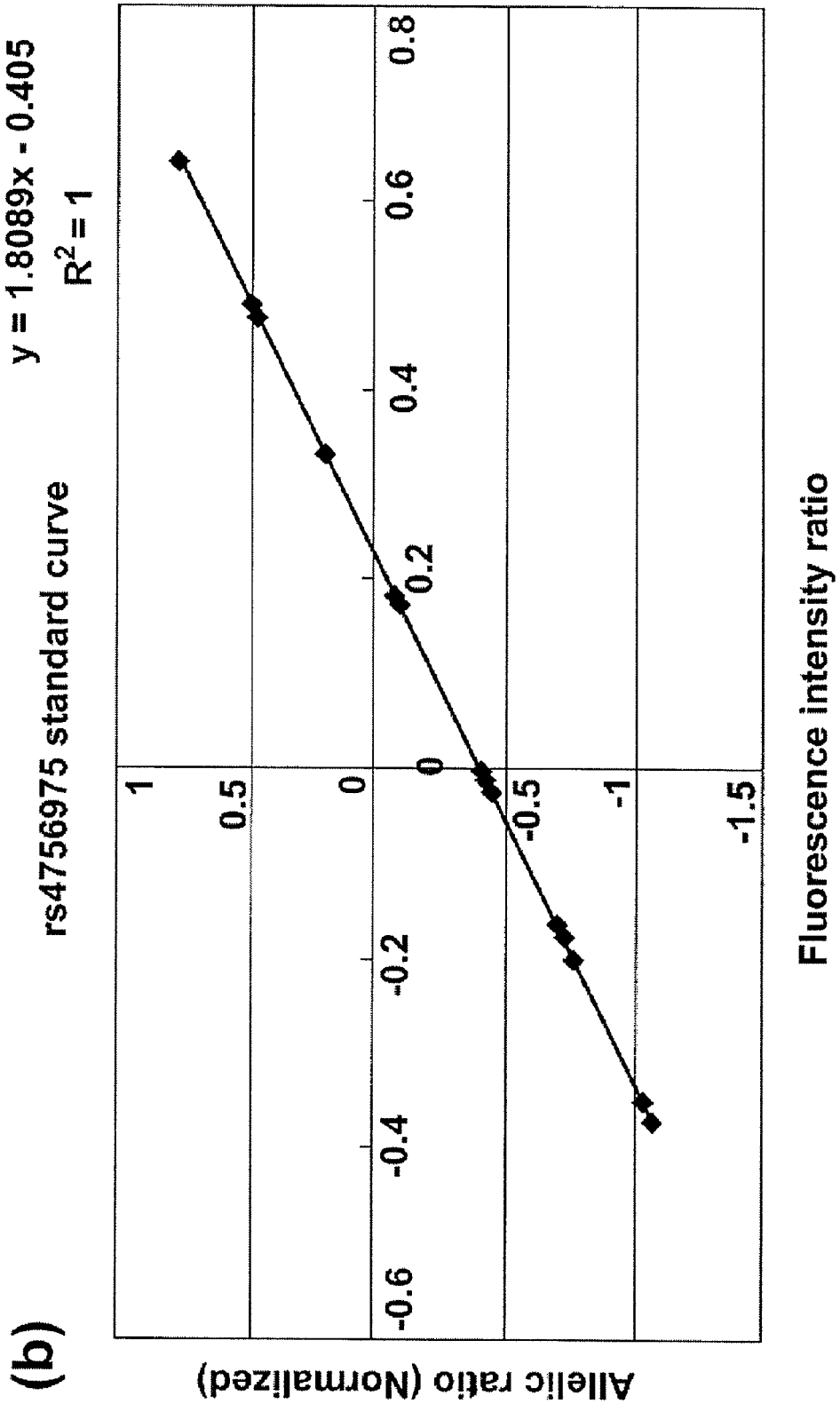
Figure 4:
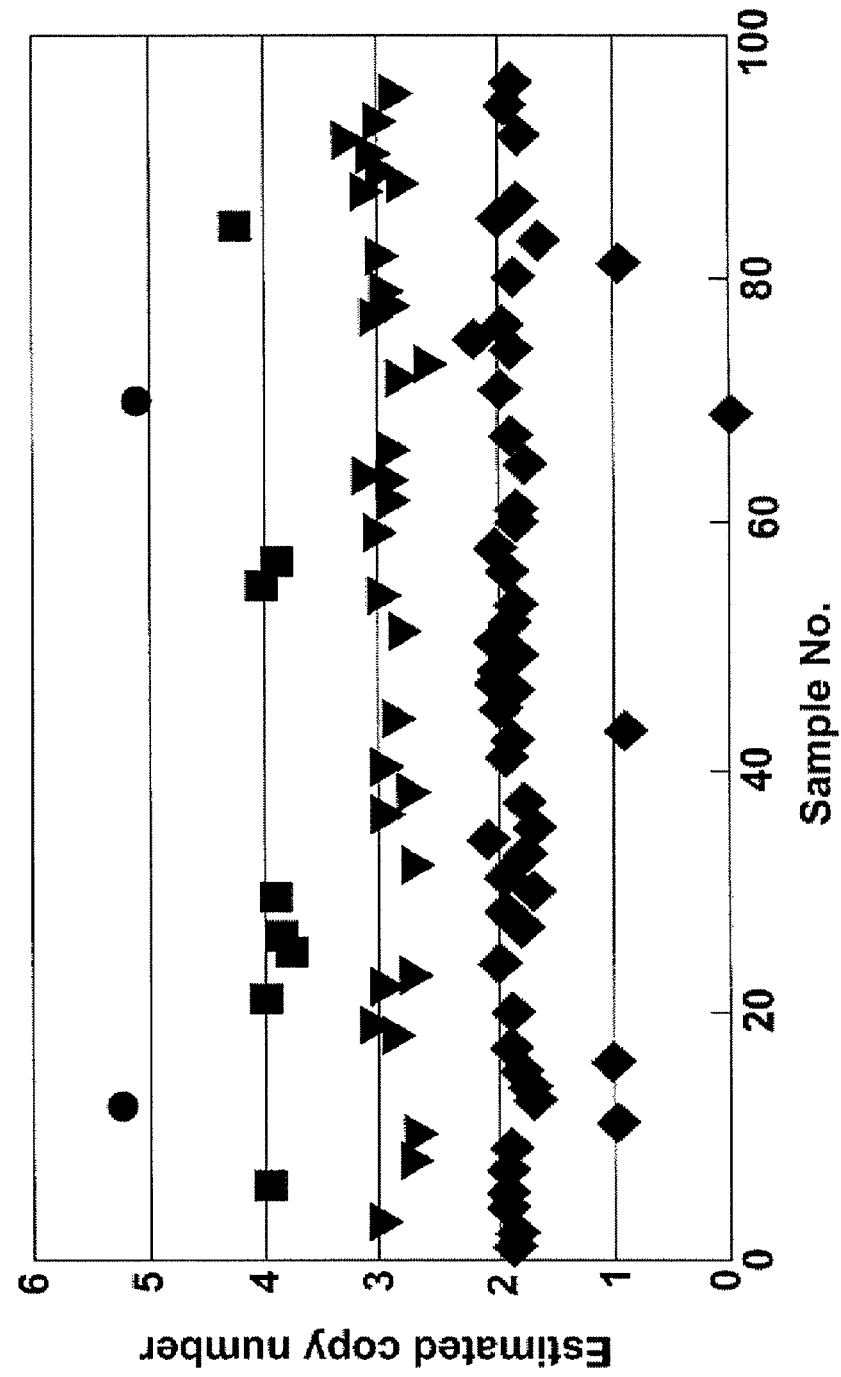
Figure 4:
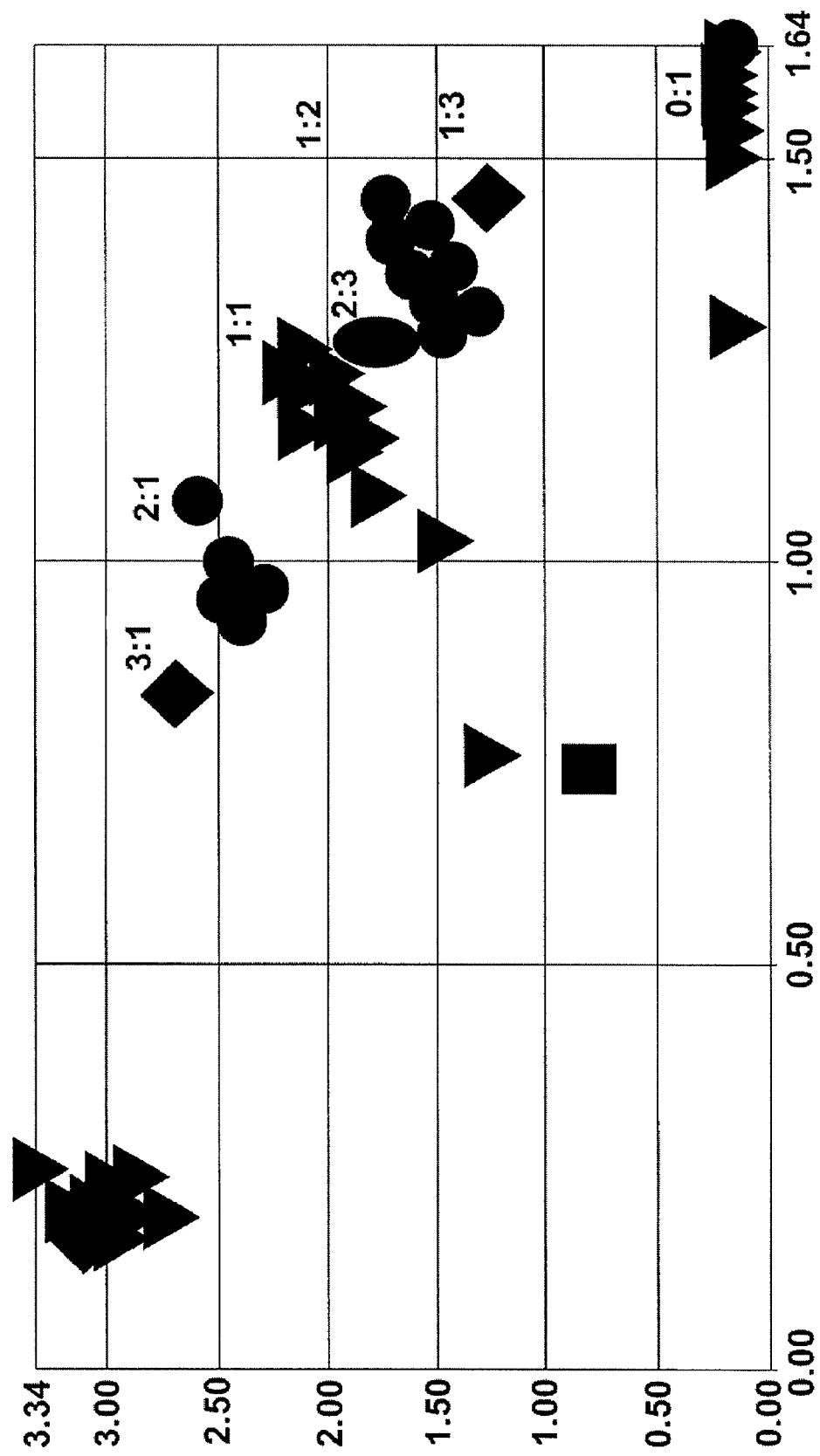

Next, the present inventors attempted to estimate the copy number of each allele by combining positional information of the dots in the AD plot graph obtained by PCR-RETINA (allele ratio) and total copy number determined by Taqman assay. To confirm the accuracy of this estimation, standard curve analysis of the rs4756975 locus was performed using CEU individuals. By mixing 2-copy heterozygote samples (NA07034 and NA12056), standard samples were prepared covering the allele ratio range from 8:1 to 1:8. PCR-RETINA was performed with the standard samples with various allele ratios, and data were analyzed at 3 minutes of the invader reaction (FIG. 4a). Logarithmic fluorescence intensity ratio (FAM intensity/Yellow intensity) was plotted on the X-axis, logarithmic allele mixing ratio was plotted on the Y-axis, and a linear regression curve was generated (FIG. 4b). This standard curve was corrected using fluorescence intensity ratios from 2-copy heterozygote individuals. Actually, PCR-RETINA was performed using CEU samples from 90 subjects, and the copy number of each allele was calculated using the linear regression curve. Individuals with various allele ratios estimated by the standard curve analysis appeared at discretely separate dot positions in AD plots (FIGS. 4c and d).

Applying PCR-RETINA for defining genomic multiplication breakpoints

Figure 5:
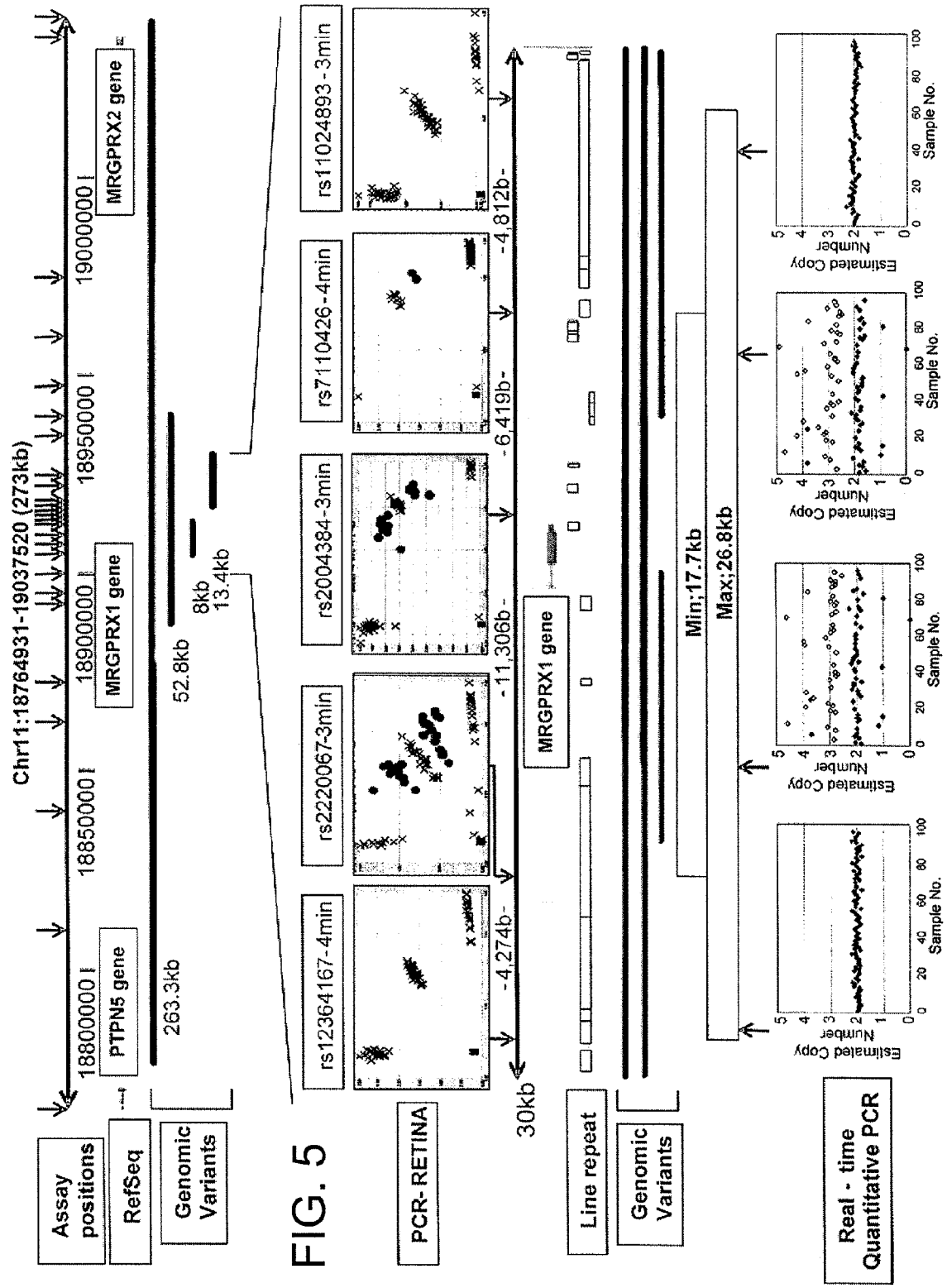
FIG. 5 shows the refinement of breakpoints in a multiplied region comprising the MRGPRX1 gene. Shown on the upper part is the region that covers the largest genomic variation (Variation_3838). The maps of the MRGPRX1 gene and its flanking regions were extracted from the UCSC genome browser and the Database of Genomic Variants. Each arrow indicates an assay position of PCR-RETINA or Taqman assay. Shown in the middle part is a representative AD plot particularly related to the determination of the boundaries of the multiplied region. ● in the AD plot represents an individual with allele asymmetry. Shown in the lower part is a copy number determined by Taqman assay. Each open diamond (◇) represents an individual with allele asymmetry in at least one of the 26 assays. The "Min" and "Max" in the boxes indicate the minimum and maximum sizes, respectively, of the multiplied region, refined by a PCR-RETINA experiment.

Next, PCR-RETINA was applied to search of genomic amplification breakpoints. Search for breakpoints in copy number variation is essential for determining whether the entire functional unit of a gene or a part thereof has been multiplied. Four CNV regions around the MRGPRX1 gene have been reported in the Database of Genomic Variants, and the present inventors utilized PCR-RETINA to search for breakpoints in these regions. Variation_0415 (8 kb) and Variation_0416 (13.4 kb) were found in fosmid paired-end sequences; Variation_2907 (52.8 kb) was found in SNP mapping array; and Variation_3838 (263.3 kb) was found in BAC-array CGH. Hence, assays were designed for 26 SNPs that cover the largest region (Variation_3838), and PCR-RETINA was performed using CEU samples from 90 subjects. As a result, allele asymmetry was observed only in a region between rs2220067 and rs7110426, and was not observed in any locus outside of the region (FIGS. 5 and 6). Therefore, it was concluded that the boundaries of the multiplied region were present between rs12364167 and rs2220067 on one side, and between rs7110426 and rs11024893 on the other side. When four Taqman assays were designed and performed for this region, results consistent with those of PCR-RETINA were obtained. As a result, it was confirmed that only the MRGPRX1 gene is present in this CNV region (FIG. 5). Confirmation of this region using the UCSC genome browser demonstrated the presence of Line-1 repeats on both sides of this CNV region (FIG. 5). From this, it was concluded that the copy number variation in this region was likely to have occurred by non-allelic homologous recombination within these repeats and the like. The same analysis but using YRI samples yielded similar data as those obtained with CEU samples.

Evaluation of Multiplex PCR RETINA (mPCR-RETINA)

The feasibility of the combination of multiplex PCR and RETINA (mPCR-RETINA) was evaluated. AD plot patterns from PCR-RETINA using one set of primers were compared with AD plot patterns from mPCR-RETINA corresponding to the above-described 26 assays. In the mPCR-RETINA, only 10 ng of genomic DNA was used for the 26 targets, and the mPCR-RETINA AD plot patterns were nearly the same as the patterns from PCR-RETINA using one set of primers (FIG. 6). This means that mPCR-RETINA is capable of simultaneously detecting a plurality of loci in a CNV region.

In determining whether CNV exhibits a difference in the copy number of a functional gene unit, it is important to define CNV breakpoints. For establishing personalized medicine, it is important to determine the copy numbers of functional alleles correlated with phenotypes, such as of the CYP2D6 gene. Using the mPCR-RETINA method, the present inventors demonstrated that allele asymmetry analysis of a particular locus enables the determination of genomic multiplication regions. Furthermore, RETINA was proven to be capable of simultaneously determining the copy number of each allele at a plurality of SNP locus in a CNV region when combined with multiplex PCR.

Example 2

Material And Method

Human Genomic DNA samples 90 genomic DNA samples from 45 Japanese and 45 Chinese subjects (JCH) used in the International HapMap project phase I were used for the allele frequency analysis and the evaluation of assay performance in mPCR-RETINAs and real-time quantitative PCR assays. Out of these 90 JCH samples, two (NA18996 and NA18540) were omitted from the sample list due to cell line artifacts reported in Am J Hum Genet 2006; 79: 275-290. JCH samples were purchased form the Coriell Cell Repositories (Camden, N.J., USA). Institutional approval for conducting research using human material was obtained from the RIKEN Ethical Advisory Committee for this study.

Multiplex PCR Amplification of CYP2D6 Gene For RETINA

To estimate the allele ratio of each SNP, indel or gene conversion polymorphism by RETINA, PCR amplifications of CYP2D6 gene were performed before RETINA. Triplex PCR covering whole CYP2D6 gene region was performed. The most of PCR primers were adopted from the primers reported in Example 1 and Biotechniques 2002; Suppl: 34-43. The forward primer for the amplicon 1 was selected from [Clin Chem 2000; 46: 1072-1077] for efficient amplification, and the reverse primer of the amplicon 3 was designed at the common site of CYP2D6 and CYP2D7P in the 3' flanking region to detect CYP2D6 *10D and CYP2D6 *36 which have CYP2D7P sequence in 3' flanking region or exon 9 and 3' flanking region, respectively, and have been reported high frequency in Japanese population [Drug Metab Pharmacokinet 2006; 21: 208-216, Clin Chim Acta 2004; 347: 217-221]. Specific primers for 2988G>A (CYP2D6*41) were designed separately because this polymorphism is located at the site between amplicon 2 and amplicon 3 and triplex PCR products does not cover this site. For assay map of CYP2D6, see FIG. 7. Takara Ex Taq HS (Takara Bio, Otsu, Shiga, Japan) was used for Triplex PCR amplification according to the manufacturer's instructions at a primer concentration of 250 nM.

PCR was performed on GeneAmp 9700 (Applied Biosystems, Foster City, Calif., USA) in 10 μl reaction volume using 10 ng genomic DNA. The PCR condition of the CYP2D6 assays was initiated at 95° C. for 2 min followed by 35cycles at 98° C. for 10 sec and 68° C. for 4 min. After PCR, amplification of PCR products was confirmed by agarose gel electrophoresis.

The sequences of all primers and probes used are listed in Table 2.

TABLE 2

Primers and Probes used in this example

| Oligo name | Purpose | role | Nucleotide sequence | SEQ ID NO: |
|---|---|---|---|---|
| 2D6-ex1F-H | Direct sequence for Exon1 | forward primer | CAGCTCCCTTTATAAGGGAAGGGT | 189 |
| 2D6Ex1R4s | Direct sequence for Exon1 | reverse primer | TCAGCAGAAGGGACTTTGTAC | 190 |
| 2D6-SF4 | Direct sequence for Exon2 | forward primer | CCAAACTGAGTTCCTCCATCACA | 191 |
| 2D6-SR4 | Direct sequence for Exon2 | reverse primer | TCGCTGGCCTGTTTCATGTC | 192 |
| 2D6-SF6 | Direct sequence for Exon3 | forward primer | AGAGACGAGGTGGGGCAAAG | 193 |
| 2D6Ex3R1s | Direct sequence for Exon3 | reverse primer | TTGCTCACGGCTTTGTCC | 194 |
| 2D6Ex4f1s | Direct sequence for Exon4 | forward primer | ACAAAGCGGGAACTGGGA | 195 |
| 2D6-SR8 | Direct sequence for Exon4 | reverse primer | TGTCTGAGATGTCCCCTCCTCC | 196 |
| 2D5Ex5F2s | Direct sequence for Exon5 | forward primer | TTGGTGAGGTCAGTGGTAAGGA | 197 |
| 2D6Ex5R1s | Direct sequence for Exon5 | reverse primer | CCCCCAAATGACCTCCAAT | 198 |
| 2D6-SF11 | Direct sequence for Exon6 | forward primer | TGACAGGTGCAGAATTGGAGGT | 199 |
| 2D6-SR11 | Direct sequence for Exon6 | reverse primer | AACAGGAGATCGACGACGTGATA | 200 |
| 2D6Ex7F2s | Direct sequence for Exon7 | forward primer | ATCCTGTAAGCCTGACCTCC | 201 |
| 2D6Ex7R2s | Direct sequence for Exon7 | reverse primer | CAGTGTGGTGGCATTGAGGA | 202 |
| 2D6Ex8F2s | Direct sequence for Exon8 | forward primer | GTCCCCCGTGTGTTTGGT | 203 |
| 2D6Ex8R1s | Direct sequence for Exon8 | reverse primer | GGGAGGTGAAGAAGAGGAAG | 204 |
| 2D6Ex9F2s | Direct sequence for Exon9 | forward primer | CCTTCCTGCCTTTCTCAGC | 205 |
| 2D6Ex9R2s | Direct sequence for Exon9 | reverse primer | GGTAAGCAGGAATGAGGCAG | 206 |
| DPKup | PCR for RETINA and direct sequence | forward primer | GTTATCCCAGAAGGCTTTGCAGGCTTCA | 207 |
| CYP2D6Triplex1R | PCR for RETINA and direct sequence | reverse primer | CACTCGCTGGCCTGTTTCATGTC | 208 |
| CYP2D6Triplex2F | PCR for RETINA and direct sequence | forward primer | CTGGAATCCGGTGTCGAAGTGG | 209 |
| CYP2D6Triplex2R | PCR for RETINA and direct sequence | reverse primer | CTCGGCCCCTGCACTGTTTC | 210 |
| CYP2D6Triplex3F | PCR for RETINA and direct sequence | forward primer | GAGGCAAGAAGGAGTGTCAGGG | 211 |
| 2D6,7exon9R | PCR for RETINA and direct sequence | reverse primer | GGGTAAGCAGGAATGAGGCAGGG | 212 |
| 2549delAIn | RETINA | Invader probe | GCTGGGTCCCAGGTCATCT | 213 |
| 2549delAAL1 | RETINA | allele probe | CGCGCCGAGG CTGTGCTCAGTTAGCAG | 214 |
| 2549delAAL2 | RETINA | allele probe | ATGACGTGGCAGAC CGTGCTCAGTTAGCAG | 215 |
| 1846G > AIn | RETINA | Invader probe | CCTTACCCGCATCTCCCACCCCCAT | 216 |

TABLE 2-continued

Primers and Probes used in this example

| Oligo name | Purpose | role | Nucleotide sequence | SEQ ID NO: |
|---|---|---|---|---|
| 1846G > AAL1 | RETINA | allele probe | CGCGCCGAGG AGACGCCCCTTTCG | 217 |
| 1846G > AAL2 | RETINA | allele probe | ATGACGTGGCAGAC GGACGCCCCTTTCG | 218 |
| 1707delTIn | RETINA | Invader probe | GGCCTCCTCGGTCACCT | 219 |
| 1707delTAL1 | RETINA | allele probe | CGCGCCGAGG CACTGCTCCAGCG | 220 |
| 1707delTAL2 | RETINA | allele probe | ATGACGTGGCAGACCCTGCTCCAGCGA | 221 |
| 2935A > CIn | RETINA | Invader probe | ACGCTGCACATCCGGRC | 222 |
| 2935A > CAL1 | RETINA | allele probe | CGCGCCGAGGTGTAGGATCATGAGCAG | 223 |
| 2935A > CAL2 | RETINA | allele probe | ATGACGTGGCAGAC GGTAGGATCATGAGCAG | 224 |
| 1758G > TIn | RETINA | Invader probe | CCTTCTGCCCATCACCCACA | 225 |
| 1758G > TAL1 | RETINA | allele probe | CGCGCCGAGG CGGAGTGGTTGGC | 226 |
| 1758G > TAL2 | RETINA | allele probe | ATGACGTGGCAGAC AGGAGTGGTTGGCG | 227 |
| 2613_2615del-AGAIn | RETINA | Invader probe | GGCCTTCCTGGCAGAGATGT | 228 |
| 2613_2615del-AGAAL1 | RETINA | allele probe | CGCGCCGAGG GAGAAGGTGAGAGTGG | 229 |
| 2613_2615del AGAAL2 | RETINA | allele probe | ATGACGTGGCAGACGAGGTGAGAGTGGCT | 230 |
| 100C > TIn | RETINA | Invader probe | GCAGTGGCAGGGGGCCTGGTGT | 231 |
| 100C > TAL1 | RETINA | allele probe | CGCGCCGAGG AGTAGCGTGCAGCC | 232 |
| 100C > TAL2 | RETINA | allele probe | ATGACGTGGCAGAC GGTAGCGTGCAGC | 233 |
| 883G > CIn | RETINA | Invader probe | CCCGAAGCGGCGCCGCAAT | 234 |
| 883G > CAL1 | RETINA | allele probe | CGCGCCGAGG CTGCAGAGGGAGGG | 235 |
| 883G > CAL2 | RETINA | allele probe | ATGACGTGGCAGAC GTGCAGAGGGAGGG | 236 |
| 124G > AIn | RETINA | Invader probe | AGCAGGTTGCCCAGCCA | 237 |
| 124G > AAL1 | RETINA | allele probe | CGCGCCGAGG CGGGCAGTGGCA | 238 |
| 124G > AAL2 | RETINA | allele probe | ATGACGTGGCAGAC TGGGCAGTGGCA | 240 |
| 1758G > AIn | RETINA | Invader probe | CCTTCTGCCCATCACCCACA | 241 |
| 1758G > AAL1 | RETINA | allele probe | CGCGCCGAGG CGGAGTGGTTGGC | 242 |
| 1758G > AAL2 | RETINA | allele probe | ATGACGTGGCAGAC TGGAGTGGTTGGCG | 243 |
| 138_139insTIn | RETINA | Invader probe | TGTTCTGGAAGTCCACATGCAT | 244 |
| 138_139insTAL1 | RETINA | allele probe | CGCGCCGAGG GACAGGTTGCCCAG | 245 |
| 138_139insTAL2 | RETINA | allele probe | ATGACGTGGCAGAC GCAGGTTGCCCAG | 246 |
| 1023C > TIn | RETINA | Invader probe | GGCCCRAARCCCAGGATCTGGT | 247 |
| 1023C > TAL1 | RETINA | allele probe | CGCGCCGAGGATGATGGGCACAGG | 248 |
| 1023C > TAL2 | RETINA | allele probe | ATGACGTGGCAGAC GTGATGGGCACAGG | 249 |
| 4125_4133 dupGTGCCCACTIn | RETINA | Invader probe | AGCTTCTCGGTGCCCACC | 250 |
| 4125_4133 dupGTGCCCACTAL1 | RETINA | allele probe | CGCGCCGAGGTGTGCCCACTGGA | 251 |

TABLE 2-continued

Primers and Probes used in this example

| Oligo name | Purpose | role | Nucleotide sequence | SEQ ID NO: |
|---|---|---|---|---|
| 4125_4133 dupGTGCCCACTAL2 | RETINA | allele probe | ATGACGTGGCAGACTGGACAGCCCCG | 252 |
| 2539_2542del-AACT1n | RETINA | Invader probe | CCCAGCTGGATGAGCTGCC | 253 |
| 2539_2542del-AACTAL1 | RETINA | allele probe | CGCGCCGAGGTAACTGAGCACAGGATG | 254 |
| 2539_2542del-AACTAL2 | RETINA | allele probe | ATGACGTGGCAGACTGAGCACAGGATGAC | 255 |
| 1973_1974insGln | RETINA | Invader probe | CCGACTCCTCCTTCAGTYCT | 256 |
| 1973_1974insGAL1 | RETINA | allele probe | CGCGCCGAGG CCTCCTGAGCTAGGT | 257 |
| 1973_1974insGAL2 | RETINA | allele probe | ATGACGTGGCAGAC CTCCTGAGCTAGGTCC | 258 |
| 2573_2574insCln | RETINA | Invader probe | CTGGGACCCAGCCCAGT | 259 |
| 2573_2574insCAL1 | RETINA | allele probe | CGCGCCGAGG CCCCCCCGAG | 260 |
| 2573_2574insCAL2 | RETINA | allele probe | ATGACGTGGCAGACCCCCCCCGAGAC | 261 |
| exon9geneconv (*36) ln | RETINA | Invader probe | CAGCCCCGGCCCAGCCACA | 262 |
| exon9geneconv (*36) AL1 | RETINA | allele probe | CGCGCCGAGGTCTCGTGTCGTCAGCTTT | 263 |
| exon9geneconv (*36) AL2 | RETINA | allele probe | ATGACGTGGCAGACCATGGTGTCTTTGCTTTCC | 264 |
| 2587_2590del-GACT1n | RETINA | Invader probe | AGCCCCCCGAGACCC | 265 |
| 2587_2590del-GACTAL1 | RETINA | allele probe | CGCGCCGAGGTGACTGAGGCCTTCC | 266 |
| 2587_2590del-GACTAL2 | RETINA | allele probe | ATGACGTGGCAGACTGAGGCCTTCCTGG | 267 |
| 1863_1864ins (TTT CGC CCC)2ln | RETINA | Invader probe | ACGCCCCTTTCGCCCT | 268 |
| 1863_1864ins (TTT CGC CCC)2AL1 | RETINA | allele probe | CGCGCCGAGGCTTTCGCCCCTTTCG | 269 |
| 1863_1864ins (TTT CGC CCC)2AL2 | RETINA | allele probe | ATGACGTGGCAGACCAACGGTCTCTTGGAC | 270 |
| 2988G > Aln | RETINA | Invader probe | AAACAGTGCAGGGGCCGAGGGAGT | 271 |
| 2988G > AAL1 | RETINA | allele probe | CGCGCCGAGGAAAGGGTACAGGCGGG | 272 |
| 2988G > AAL2 | RETINA | allele probe | ATGACGTGGCAGACGAAGGGTACAGGCGG | 273 |
| 3259_3260insGTln | RETINA | Invader probe | GATGTCCCAAAGCGCTGT | 273 |
| 3259_3260insGTAL1 | RETINA | allele probe | CGCGCCGAGG CACACCTCATGAATCACG | 274 |
| 3259_3260insGTAL2 | RETINA | allele probe | ATGACGTGGCAGACCACCTCATGAATCACGG | 275 |
| 2950G > Cln | RETINA | Invader probe | CTGTTTCCCAGATGGGCTCAT | 276 |
| 2950G > CAL1 | RETINA | allele probe | CGCGCCGAGG CGCTGCACATCCG | 277 |
| 2950G > CAL2 | RETINA | allele probe | ATGACGTGGCAGAC GGCTGCACATCCG | 278 |
| 3201C > Tln | RETINA | Invader probe | GTGATAGGGCAGGTGCGGA | 279 |
| 3201C > TAL1 | RETINA | allele probe | CGCGCCGAGG CGACCAGAGATGGGT | 280 |
| 3201C > TAL2 | RETINA | allele probe | ATGACGTGGCAGACTGACCAGAGATGGGT | 281 |

TABLE 2-continued

Primers and Probes used in this example

| Oligo name | Purpose | role | Nucleotide sequence | SEQ ID NO: |
|---|---|---|---|---|
| 2291G > A1n | RETINA | Invader probe | CCAAGTRCCAGCCTCCACA | 282 |
| 2291G > AAL1 | RETINA | allele probe | CGCGCCGAGGTCTCTCTCCTTGCCC | 283 |
| 2291G > AAL2 | RETINA | allele probe | ATGACGTGGCAGACCCTCTCTCCTTGCCC | 284 |
| 2D6Int2qPCRF | Real-time quantitative PCR | forward primer | CAGGAGCCCAATGGGTGA | 285 |
| 2D6Int2qPCRR | Real-time quantitative PCR | reverse primer | ACTTCGACACCGGATTCCAG | 286 |
| 2D6Int2qPCR-TaqMan | Real-time quantitative PCR | TaqMan | FAM-TGGCGCATTTCC | 287 |
| 2D6Int6-TaqMan | Real-time quantitative PCR | TaqMan | fam-CCCCCGCCTGTACC | 288 |
| 2d6Int6F | Real-time quantitative PCR | forward primer | GGTGTCCCAGCAAAGTTCATG | 289 |
| 2d6Int6R | Real-time quantitative PCR | reverse primer | TGAGCCCATCTGGGAAACA | 290 |
| 2D6-Ex9-TaqMan | Real-time quantitative PCR | TaqMan | FAM-CCCCTATGAGCTTTGTG | 291 |
| 2D6-Ex9-F | Real-time quantitative PCR | forward primer | GGCCCAGCCACCATGG | 291 |
| 2D6-Ex9-R | Real-time quantitative PCR | reverse primer | CTCTGGCTAGGGAGCAGGC | 292 |
| 2D6-5'flank-TaqMan | Real-time quantitative PCR | TaqMan | FAM-CCGGCATGGCTG | 293 |
| 2D6-5'flankF | Real-time quantitative PCR | forward primer | GACAGGAGTGGTCCCATCCA | 294 |
| 2D6-5'flankR | Real-time quantitative PCR | reverse primer | TACAGACCCGGCACCAAGTAC | 295 |
| Dpkup | Long PCR (total gene) | forward primer | GTTATCCCAGAAGGCTTTGCAGGCTTCA | 296 |
| Dpklow | Long PCR (total gene) | reverse primer | GCCGACTGAGCCCTGGGAGGTAGGTA | 297 |
| 2D6 D1 | Long PCR (Deletion) | forward primer | GCCACTCTCGTGTCGTCAGCTTT | 298 |
| 2D6 D2 | Long PCR (Deletion) | reverse primer | GGCATGAGCTAAGGCACC | 299 |
| 2D6 13 | Long PCR (Deletione) | forward primer | ACCGGGCACCTGTACTCCTCA | 300 |
| 2D6 24 | Long PCR (Deletion) | reverse primer | GCATGAGCTAAGGCACCCAGAC | 301 |
| 2D6-7S | Long PCR (Duplication 1st PCR) | forward primer | AAGGAGTGTCAGGGCCGGA | 302 |
| 2D6-2AS | Long PCR (Duplication 1st PCR) | reverse primer | AGCTCGGACTACGGTCATCAC | 303 |
| 2D6Ex7F6s | Long PCR (Duplication 2nd PCR) | forward primer | TGATTCATGAGGTGCAGCG | 304 |
| cyp-32r | Long PCR (Duplication 2nd PCR) | reverse primer | CACGTGCAGGGCACCTAGAT | 305 |
| *36-*36F | Long PCR (*36-*36) | forward primer | GCACTCTCGTGTCGTCAGCTTT | 306 |
| *36-*36R | Long PCR (*36-*36) | reverse primer | GGCATGAGCTAAGGCACC | 307 |

Real-Time Invader Assays (RETINA)

Figure 7:
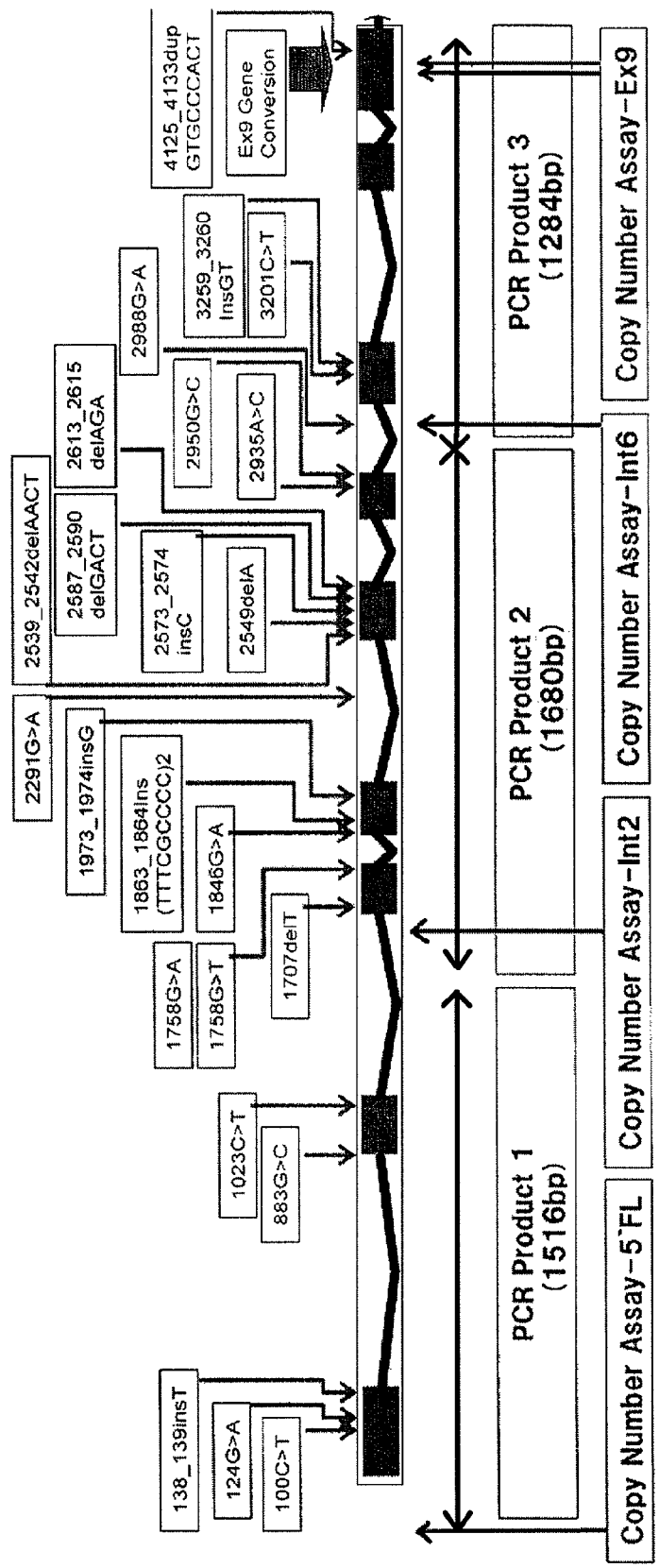
FIG. 7 shows assay map of CYP2D6 mPCR-RETINAs and real-time quantitative PCR (TaqMan) assays.

24 polymorphisms affected on the enzymatic activity were retrieved from CYP allele database (www.cypalleles.ki.se/), and RETINAs were performed (Table 3). Assay locations are indicated in FIG. 7. For the RETINAs of 1846G>A and 100C>T, the assays were adopted from Biotechniques 2002; Suppl: 34-43. For the remaining polymorphisms, Invader assays were designed according to the guideline recommended by Third Wave Technologies (Madison, Wis., USA).

The sequences of all probes are listed in Table 2. FRET probes labeled with FAM or Yakima Yellow were purchased from Third Wave Technologies. Rox dye (Sigma, Saint Louis, Mo., USA) was used for the normalization of reporter signals. Using multiplex PCR products, RETINA for each polymorphism was carried out in duplicate in the reaction volume of 4 ul on ABI prism 7900 (Applied Biosystems) according to the same protocol as above described. Data analysis was performed with Excel (Microsoft, Redmond, Wash., USA).

Allele ratio in each sample was estimated from the information of relative dot positions in the AD plot graph in RETINA as above.

TABLE 3

Target polymorphisms for mPCR-RETINA

| Polymorphisms affecting phenotype | Haplotype | Polymorphism type | Enzyme Activity | Location |
|---|---|---|---|---|
| 2549delA | *3 | Indel | None | exon5 |
| 1846G > A | *4 | SNP | None | Intron3 |
| 1707delT | *6 | Indel | None | exon3 |
| 2935A > C | *7 | SNP | None | exon6 |
| 1758G > T | *8 | SNP | None | exon3 |
| 2613__2615delAGA | *9 | Indel | Decr | exon5 |
| 100C > T | *10, *36 *4,*14A | SNP | Decr | exon1 |
| 883G > C | *11 | SNP | None | Intron1 |
| 124G > A | *12 | SNP | None | exon1 |
| 1758G > A | *14A, *14B | SNP | None | exon3 |
| 138__139insT | *15 | Indel | None | exon1 |
| 1023C > T | *17 | SNP | Decr | exon2 |
| 4125__4133dupGTGCCCACT | *18 | Indel | None | exon9 |
| 2539__2542delAACT | *19 | Indel | None | exon5 |
| 1973__1974insG | *20 | Indel | None | exon4 |
| 2573__2574insC | *21 | Indel | None | exon5 |
| CYP2D7 in Ex9 | *36, *4N | Gene Conversion | Negligible | exon9 |
| 2587__2590delGACT | *38 | Indel | None | exon5 |
| 1863__1864ins (TTT CGC CCC)2 | *40 | Indel | None | exon4 |
| 2988G > A | *41 | SNP | Decr | Intron6 |
| 3259__3260insGT | *42 | Indel | None | exon7 |
| 2950G > C | *44 | SNP | None | exon6 |
| 3201C > T | *56 | SNP | None | exon7 |
| 2291G > A | *59 | SNP | Decr | Intron4 |

These alleles of the enzyme result in Poor metabolizer (PM), Intermediate metabolizer (IM), Extensive metabolizer (EM) or Ultrarapid metabolizer (UM) of the CYP2D6 substrate drugs and the frequencies of these alleles differ among populations. For example, CYP2D6*3 (2549delA), CYP2D6*4 (1846G>A), CYP2D6*5 (whole gene deletion) and CYP2D6*6 (1707delT) have been reported as null function of enzyme and widely distribute in Caucasian population [Pharmacogenetics 1998; 8: 181-185]. Individuals with only these null alleles are defined as PM of drugs that are metabolized mainly by CYP2D6 and 5-10% of Caucasians are considered to be PMs [DNA Cell Biol 1991; 10: 545-558]. On the other hand, the individuals with multiple active genes like CYP2D6*1xN/*1 and CYP2D6*1x2/*1 are defined as UM and 1-7% of Caucasians has been reported as UMs [Drug Metab Rev 1999; 31: 449-459]. In Asian population, the proportion of PMs and UMs are lower than Caucasian (PM: <1%, UM: 1-2%) [Clin Pharmacol Ther 1985; 38: 402-8, Pharmacogenetics 1995; 5: 159-164], and CYP2D6*10 (100C>T) has been reported as common allele and present in approximately 40-50% of Asians [Pharmacogenetics 1993; 3: 256-263, Biochem Biophys Res Commun 2002; 293: 969-973]. This allele has been reported to have impaired enzymatic activity, and the homozygote individuals of this allele and the heterozygote individuals with a combination of this allele and other null alleles are defined as IM. Recently, the CYP2D6*36 (100C>T and Gene conversion to CYP2D7P in exon 9) has also been reported as common in Asian population and present in the form of CYP2D6*10-*36 tandem type duplication [Drug Metab Pharmacokinet 2006; 21: 208-216]. Little is known about association between CYP2D6*10-*36 tandem type duplication and its enzymatic activity, though the enzymatic activity of CYP2D6*36 was reported to be negligible [Drug Metab Dispos 2006; 34: 563-569].

Real-Time Quantitative PCR (TaqMan Assays)

Real-time quantitative PCR was carried out using TaqMan assay to estimate the total copy number of CYP2D6 gene. Five TaqMan assays were designed at different sites within and around CYP2D6 gene, with a greatest care in target specific recognition for accurate estimation. Assay locations are indicated in FIG. 7. Primers and TaqMan probes were designed with the Primer Express 2.0 for three assays out of five. The remaining two were reported assay [J Biomed Biotechnol 2005; 005: 48-53] and commercially-available assay (Applied Biosystems), respectively. These TaqMan probes were labeled with FAM at the 5' end and linked by Non Fluorescence Quencher (NFQ) and MGB at the 3' end. For the compensation of the difference in genomic DNA quantity among samples, the RNase P assay labeled with VIC (Applied Biosystems) was used. All Taqman assays were performed according to the previously reported protocols and copy number was calculated by the delta-delta Ct method [J Biomed Biotechnol 2005; 005: 48-53]. The HapMap CEU control samples (NA12753 or NA12707) with two copies of CYP2D6, which we identified in Hum Mutat 2008; 29: 182-189, were used as calibrators. All samples were examined in quadruplicate and the mean copy number values were used in the scatter plot analysis. The primer and probe sequences of all TaqMan assays are listed in Table 2.

Haplotype/Diplotype Estimation And Phenotype Prediction

First, the copy number of each polymorphism was estimated by combining the data of allele ratio and the total gene copy number. After that, haplotype/diplotype estimation for CYP2D6 alleles was performed with the Expectation-Maximization (EM) algorism based analysis software, named "the CNV phaser" (provided by Dr. Kato of Laboratory for Medical Informatics, SNP Research Center, RIKEN) [Kato et al., submitted, also described in JP 2008-048748 and PCT/JP2008/053567], which can estimate haplotype structures in CNV or non-CNV regions in a population and assign a combination of alleles (diplotype) to each individual. Each individual has "diplotype probability value" which means the probability that the individual has one certain diplotype among all possible diplotypes that are consistent with the observed genotyping datasets. A diplotype pattern with the highest diplotype probability in each sample was picked up and allele frequency was calculated. Traditional phenotype prediction and activity scoring were performed as described in Clin Chem 2004; 50: 1623-1633, Ther Drug Monit 2006; 28: 673-677.

Long PCR For Confirmation of CNVs

Long PCR was performed to confirm CNVs containing whole gene deletion (CYP2D6*5) and gene duplications (CYP2D6*1x2, CYP2D6*2x2, CYP2D6*10x2, CYP2D6*36x2 or CYP2D6*10-36) according to the protocols as described in Drug Metab Pharmacokinet 2006; 21: 208-216, Drug Metab Pharmacokinet. 2005; 20: 345-50, Pharmacogenetics 2002; 12: 659-662.

Direct Sequencing

Direct sequencing was performed on the ABI prism 3700 DNA sequencer (Applied Biosystems) to confirm alleles detected in mPCR-RETINAs in JCH samples. The reported primers and self-designed primers were used for this experiment [Drug Metab Pharmacokinet 2004; 19: 313-319]. Whole CYP2D6 gene region was amplified in long PCR and used for the sequence reaction according to the protocol recommended by Applied Biosystems. The sequence data were analyzed with the SeqScape software (Applied Biosystems). The sequences of all the primers for direct sequencing are listed in Table 2.

Results

CYP2D6 Genotyping In JCH Samples By mPCR-RETINAs And Real-Time Quantitative PCR

Figure 8:
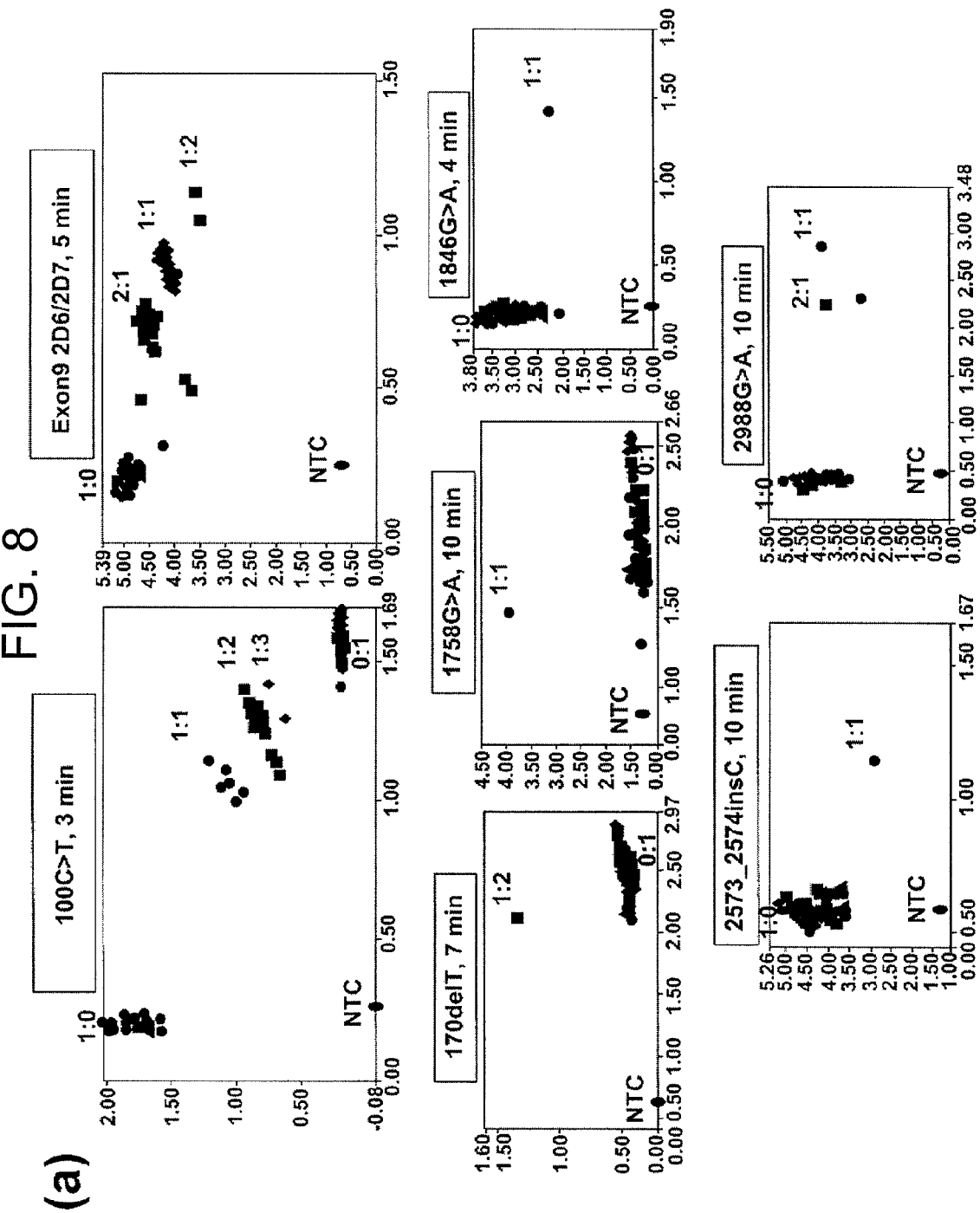
FIG. 8 shows estimation of allele ratio and total gene copy number. (a) Estimation of allele ratios by mPCR-RETINAS using JCH samples. Alphanumeric characters in the boxes indicate polymorphisms and time points of RETINA. The AD plots at the time point shortly before the fluorescence intensities reached the plateau phase are shown. The vertical axis of the AD plots indicates the normalized FAM allele signal, and the horizontal axis indicates the normalized Yakima Yellow allele signal. Total gene copy number obtained by real-time quantitative PCR is indicated. Triangles, circles, squares, and diamonds indicate samples with 1-copy, 2-copy, 3-copy and 4-copy, respectively. Ovals indicate no template control (NTC). The numbers in the AD plot indicate the allele ratio estimated by RETINA. (b) Estimation of total gene copy number by real-time quantitative PCR in JCH samples. All reactions were performed in quadruplicate and mean copy number values are shown in the scatter plots. Total gene copy number is indicated. Diamonds, triangles, squares, and circles indicate 1-copy, 2-copy, 3-copy and 4-copy, respectively.
Figure 8:
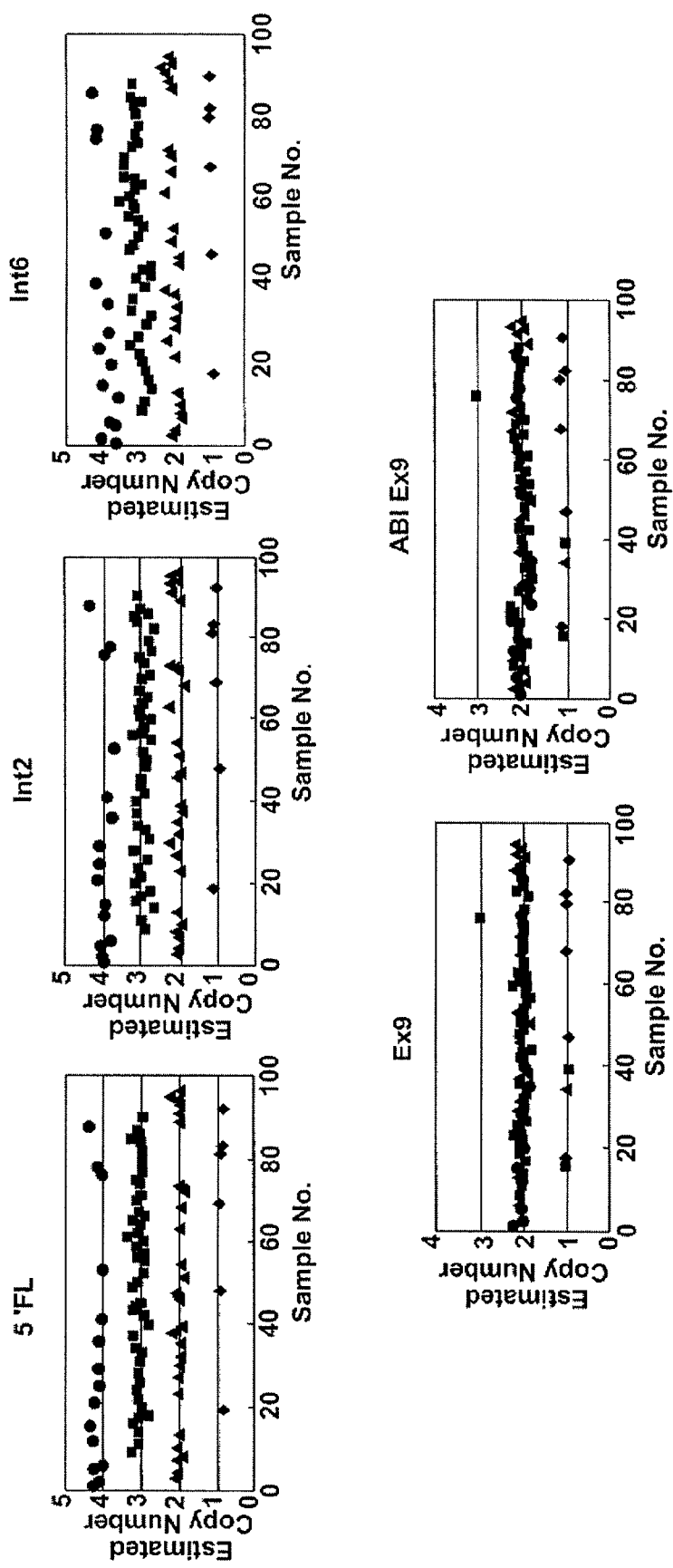

First, 24 polymorphisms with reported functional significance in-vivo or in-vitro were retrieved from CYP allele database. Invader assays were designed and constructed for each polymorphism and triplex-PCR and 24 RETINAs were performed using HapMap JCH samples. Then, allele ratio data was obtained with 100% of assay success rate and variant types were detected in 7 loci. Additionally, clear allelic asymmetries were observed in the heterozygote clusters especially in 100C>T assay and exon 9 CYP2D6/CYP2D7P gene conversion assay, and allele ratio could be estimated in each polymorphism (FIG. 8a). Direct sequencing was performed in all JCH samples and the variant types were confirmed.

At the same time of evaluation of mPCR-RETINAs, five real-time quantitative assays were performed for estimation of total gene copy number. We designed assays at the specific sites over CYP2D6 gene region and investigated whether total copy number values of CYP2D6 in each sample was constant among assays. Having inspected 88 JCH samples, complete concordance was observed between two assays located in exon 9 or among three assays located in other different sites (FIG. 8b). The copy number data between the two assays in exon 9 and the other three assays were clearly different in multiple samples. It is presumed that this difference was caused by existence of the exon 9 CYP2D6/CYP2D7P gene conversion polymorphism, which has widely distributed as CYP2D6*36 in Japanese population [Drug Metab Pharmacokinet 2006; 21: 208-216] and can not be detected by CYP2D6-specific TaqMan assays designed at exon 9 due to 13-base substitution. Complete concordance between the ratio of CYP2D6/CYP2D7P in exon 9 from the difference in real-time quantitative PCR assays and the ratio from a RETINA for this polymorphism was observed, it was confirmed that the copy number data from the three assays were total gene copy number of CYP2D6 gene and the copy number data from the two assays in exon 9 were the copy number of CYP2D6 gene except alleles with exon 9 gene conversion polymorphism.

Data of allele ratios in 24 polymorphisms from mPCR-RETINA and total gene copy number from real-time quantitative PCR assays (not in exon 9) were combined, and clustering separation of heterozygote clusters were inspected in AD plot views in every total gene copy number in all JCH samples. As a result, no discrepancy was observed between allele ratios and total copy numbers and high accuracy of these assays was confirmed. By combining the data from these two techniques, the copy number values of 24 SNPs, Indels and Gene conversion polymorphism could be obtained in all JCH samples.

Haplotype/Diplotype Estimation And Phenotype Prediction

By using the copy number data of each polymorphism in 88 JCH samples, haplotypes (alleles) and diplotypes were estimated with the CNV phaser software. After estimation of haplotypes in the population and diplotypes in each sample, the frequency of each allele was calculated (Table 4). The allele with highest frequency was "Others" which was considered to be mainly CYP2D6*1 and CYP2D6*2 from the recent report [Drug Metab Pharmacokinet 2006; 21: 208-216] and the value was 0.466 in 88 JCH samples. Second highest was CYP2D6*10-*36 tandem type and the value was 0.358. CYP2D6*10 and whole gene deletion CYP2D6*5 was 0.057 and 0.051, respectively, and Others-Others which may be duplication of functional gene like CYP2D6*1x2 or CYP2D6*2x2 was 0.006. Also, the CNV phaser estimated non-reported CYP2D6*10-*36-*36 allele at very low frequencies. When comparing the allele frequency data with the recent reports [Drug Metab Pharmacokinet 2006; 21: 208-216, Drug Metab Pharmacokinet 2004; 19: 313-319], they were quite similar to each other (Table 4).

TABLE 4

| Allele frequencies in 88 JCH samples | | |
|---|---|---|
| Haplotype | 88 JCH | Soyama et al 2004 & 2006 254 Japanese* |
| *3 | 0.000 | 0.000 |
| *4 | 0.006 | 0.000 |
| *5 | 0.051 | 0.051 |
| *6 | 0.006 | 0000 |
| *7 | 0.000 | 0.000 |
| *8 | 0.000 | 0.000 |
| *9 | 0.000 | 0.000 |
| *10 | 0.057 | 0.053 |
| *10-*10 | 0.000 | 0.004 |
| *10-*36 | 0.358 | 0.262 |
| *10-*36-*36 | 0.023 | 0.000 |
| *11 | 0.000 | 0.000 |
| *12 | 0.000 | 0.000 |
| *14A | 0.000 | 0.000 |
| *14B | 0.006 | 0.007 |
| *15 | 0.000 | 0.000 |
| *17 | 0.000 | 0.000 |
| *18 | 0.000 | 0.002 |
| *19 | 0.000 | 0.000 |
| *21 | 0.006 | 0.007 |

TABLE 4-continued

Allele frequencies in 88 JCH samples

| Haplotype | 88 JCH | Soyama et al 2004 & 2006 254 Japanese* |
|---|---|---|
| *41 | 0.017 | —** |
| *42 | 0.000 | 0.000 |
| *44 | 0.000 | 0.002 |
| *56 | 0.000 | 0.000 |
| Others | 0.466 | 0.582 |
| Others-Others | 0.006 | 0.010 |
| Undetermined | 0.000 | 0.020 |

*The frequency data from two reports using same samples were combined. The frequency data of CYP2D6*5, CYP2D6*10, CYP2D6*10-10, CYP2D610-*36 and Others-others (CYP2D6*1x2, CYP2D6*2x2) were extracted from Soyama et al 2006. The data of other alleles were from Soyama et al 2004. CYP2D6*1, CYP2D6*2, CYP2D6*48, CYP2D6*50 and CYP2D6*51 in these reports are included in "Others".

**Detection of CYP2D6*41 in the 254 samples has been reported but specific frequency number was not in these reports For confirmation of estimated whole gene deletion and multiplication, long PCR was conducted according to reported protocols using 88 JCH samples. As a result, good concordance was observed between the result from long PCR and that from the CNV phaser.

Genotype data was converted to predicted phenotype data based on traditional classification and enzyme activity score (Table 5) [Clin Chem 2004; 50: 1623-1633, Pharmacogenomics J 2007; 7: 257-265, Mol Ther 2008; 83: 234-242]. Phenotype prediction showed no PM in 88 JCH samples, whose diplotype was CYP2D6*21-*21/*5 and CYP2D6*14B/*5. Twenty one in JCH (23.9%) samples were grouped as IMs, 66 in JCH (75%) as EMs, and one in JCH (1.1%) as UMs. In activity score analysis, PMs were 0, IMs were classified into 3 groups (0.5, 1 or 1.5) according to the copy number of CYP2D6*10 and CYP2D6*41, and EMs were classified into two groups (1 or 2) and UMs were 3.

TABLE 5

Diplotype and predicted Phenotype in 88 JCH samples

| Diplotype | JCH | Predicted phenotype* | Predicted Activity Score** | Diplotype Probability*** |
|---|---|---|---|---|
| *10-*36-*36/*5 | 2 | IM | 0.5 | 0.739 |
| *10-*36/*5 | 1 | IM | 0.5 | 1.000 |
| *10-*36/*6 | 1 | IM | 0.5 | 1.000 |
| *10-*36/*10-*36 | 12 | IM | 1 | 0.969 |
| *10-*36/*41 | 1 | IM | 1 | 0.994 |
| *10/*10 | 1 | IM | 1 | 0.910 |
| *10/*10-*36 | 2 | IM | 1 | 0.995 |
| *10/*41 | 1 | IM | 1 | 1.000 |
| *14B/Others | 1 | EM | 1 | 1.000 |
| *21/Others | 1 | EM | 1 | 1.000 |
| *4/Others | 1 | EM | 1 | 1.000 |
| Others/*5 | 6 | EM | 1 | 1.000 |
| *10-*36-*36/Others | 2 | EM | 1.5 | 1.000 |
| *10-*36/Others | 34 | EM | 1.5 | 1.000 |
| *10/Others | 5 | EM | 1.5 | 1.000 |
| *41/Others | 1 | EM | 1.5 | 1.000 |
| Others/Others | 15 | EM | 2 | 0.996 |
| Others/Others-Others | 1 | UM | 3 | 1.000 |
| Total | 88 | | | |

*PM: carriers of two inactive haplotypes like CYP2D6*5, *14B, or *21-*21; IM: carries of a combination of impaired activity haplotypes like CYP2D6*10 and *41 or a combination of impaired activity and inactive haplotype. EM: Carriers of one or two copies of fully active haplotypes like "Others"; UM: carriers of multiple active genes caused by multiplication of haplotypes of fully active genes.

**Predicted CYP2D6 activity score: combination of haplotypes were calculated as follows: inactive haplotypes: score 0 (CYP2D6*4, *5, *14B, *21); haplotypes with impaired activity: score 0.5 (CYP2D6*10, *41); haplotypes with full activity or duplication/triplication haplotypes with impaired activity: score 1 (Others, *10-*10, *10-*10-*36); duplication haplotypes with full activity: Score2 (Others-Others)

***diplotype probability means the probability that the individual has one certain diplotype among all possible diplotypes that are consistent with the observed genotyping datasets. This is calculated by the CNV phaser.

The above results demonstrated that the present system can provide accurate genotype and haplotype/diplotype data.

mPCR-RETINA has several advantages over reported methods for detecting genomic multiplication. First, mPCR-RETINA only requires a smaller amount of genomic DNA. In fact, only 10 ng of genomic DNA was used in the mPCR-RETINA. This means that 0.38 ng of genomic DNA is necessary for one SNP analysis. The amount of genomic DNA required per locus is much less than other methods; for example, 0.5-12.5 ng/site for MLPA, 12.5-25 ng/site for MAPH, 10 ng/site for QMPSF, 5-100 ng/site (TaqMan and SYBR) for real-time quantitative PCR, 10 ng/site for melting curve analysis, and 5-10 µg/site for Southern blot analysis.

Second, mPCR-RETINA is highly specific and enables assay even in regions of repeat sequences and gene families. Generally, multiplication regions are often highly similar to other regions in the genome, and are sometimes difficult to detect. Other PCR-based methods are usually subject to limitations concerning amplicon size; it is often difficult to design a primer for a region of specificity. However, mPCR-RETINA is applicable to amplicon sizes 1 kb or more in length, allowing the designing of a PCR primer for a specific region to avoid PCR amplification of homologous regions. Furthermore, the invader assay exhibits higher specificity than the method based on hybridization alone, because of the use of Cleavase VIII enzyme, which recognizes the unique triplet structure in the target SNP site. In fact, PCR-RETINA allowed genotyping in three SNP assays within the Line-1 repeats (rs2220067, rs11517776 and rs11024893, FIG. 6).

Third, PCR-RETINA is an accurate allele-specific quantitative assay capable of estimating the copy number of each allele, and allows calculation of the copy number of each allele when combined with real-time quantitative PCR. This feature is useful in the analysis of the correlation between CNV and phenotypes, and clinical diagnosis.

Other advantages of mPCR-RETINA are protocol simplicity and low cost. mPCR-RETINA is the simple combination of PCR and invader assay, and enables concurrent testing of a large number of samples within 5 minutes. The use of multiplex PCR and the obviation of a locus-specific fluorescent probe will lead to cost reductions.

INDUSTRIAL APPLICABILITY

According to the present invention, copy number variation can be detected quickly, conveniently and inexpensively. In particular, because the present invention can define multiplication breakpoints in a CNV region, it is possible to determine whether a gene in the CNV region has been multiplied in the functional unit thereof. The present invention is also useful in elucidating the correlation between the gene and disease susceptibility or drug responsiveness to realize personalized medicine.

The present application claims priority to JP 2007-086067, filed on Mar. 28, 2007, the entire content of the application is incorporated herein by reference.

The invention claimed is:

1. A method of determining the genotype of a subject in a genomic region comprising an SNP site, comprising a step for performing typing of the SNP site with a DNA-containing sample comprising the genomic region from the subject as the template by an invader assay, wherein fluorescence of the invader assay is measured on a real time basis, and wherein the copy number ratio of both alleles of the SNP is determined using the ratio of fluorescence intensity corresponding to each allele at a time before saturation of fluorescence intensity of the invader assay.

2. The method according to claim 1, wherein the genomic region comprising an SNP site is present in a CNV region.

3. The method according to claim 1, which is for detecting multiplication accompanied by allele asymmetry.

4. The method according to claim 1, further comprising a step for amplifying the genomic region comprising an SNP site prior to the invader step.

5. The method according to claim 4, wherein the genomic region comprises a plurality of SNP sites, and wherein a plurality of regions comprising the plurality of SNP sites are simultaneously amplified in the step of amplification.

6. The method according to claim 4, wherein the copy number of each allele is determined based on the total copy number of both alleles determined using quantitative PCR.

7. The method according to claim 6, wherein the quantitative PCR is performed by the TaqMan method.

8. The method according to claim 5, comprising defining CNV breakpoints by identifying a region in which a plurality of SNP sites, whether continuous or not, exhibit multiplication or deletion accompanied by allele asymmetry.

* * * * *